(12) United States Patent
Fisher et al.

(10) Patent No.: US 6,989,147 B2
(45) Date of Patent: Jan. 24, 2006

(54) TRUNCATED SOLUBLE TUMOR NECROSIS FACTOR TYPE-I AND TYPE-II RECEPTORS

(75) Inventors: Eric F. Fisher, New Braunfels, TX (US); Carl K. Edwards, III, Superior, CO (US); Gary L. Kieft, Boulder, CO (US)

(73) Assignee: Amgen Inc., Thousand Oaks, CA (US)

( * ) Notice: Subject to any disclaimer, the term of this patent is extended or adjusted under 35 U.S.C. 154(b) by 257 days.

(21) Appl. No.: 09/882,735

(22) Filed: Jun. 15, 2001

(65) Prior Publication Data

US 2003/0054439 A1 Mar. 20, 2003

Related U.S. Application Data

(63) Continuation of application No. 09/214,613, filed as application No. PCT/US97/12244 on Jul. 19, 1997, now abandoned.
(60) Provisional application No. 60/039,792, filed on Mar. 4, 1997, provisional application No. 60/037,737, filed on Jan. 23, 1997, provisional application No. 60/032,534, filed on Dec. 6, 1996, provisional application No. 60/621,443, filed on Jul. 9, 1996, and provisional application No. 60/039,314.

(51) Int. Cl.
*A61K 38/17* (2006.01)
*C07K 14/705* (2006.01)

(52) U.S. Cl. ............... 424/185.1; 424/134.1; 424/178.1; 424/192.1; 530/350; 530/402; 530/815; 514/12; 514/23; 536/23.5; 435/320.1; 435/69.1; 435/325; 435/252.3

(58) Field of Classification Search ............ 424/185.1, 424/134.1, 178.1, 192.1; 530/350, 402, 815; 514/12, 23; 536/23.5; 435/320.1, 69.1, 325, 435/252.3
See application file for complete search history.

(56) References Cited

U.S. PATENT DOCUMENTS

| | | | |
|---|---|---|---|
| 4,179,337 A | 12/1979 | Davis et al. | |
| 4,289,690 A | 9/1981 | Pestka et al. | |
| 4,522,750 A | 6/1985 | Ades et al. | |
| 4,560,649 A | 12/1985 | Saxena et al. | |
| 4,578,335 A | 3/1986 | Urdal et al. | |
| 4,609,546 A | 9/1986 | Hiratani | |
| 4,670,417 A | 6/1987 | Iwasaki et al. | |
| 4,670,563 A | 6/1987 | Jansen et al. | |
| 4,675,285 A | 6/1987 | Clark et al. | |
| 4,677,027 A | 6/1987 | Porath et al. | |
| 4,696,980 A | 9/1987 | Porath | |
| 4,760,067 A | 7/1988 | Firestone | |
| 4,766,106 A | 8/1988 | Katre et al. | |
| 4,789,658 A | 12/1988 | Yoshimoto et al. | |
| 4,791,192 A | 12/1988 | Nakagawa et al. | |
| 4,847,325 A | 7/1989 | Shadle et al. | |
| 4,902,502 A | 2/1990 | Nitecki et al. | |
| 4,904,584 A | 2/1990 | Shaw | |
| 4,917,888 A | 4/1990 | Katre et al. | |
| 4,931,544 A | 6/1990 | Katre et al. | |
| 4,935,233 A | 6/1990 | Bell et al. | |
| 4,959,314 A | 9/1990 | Mark et al. | |
| 4,966,888 A | 10/1990 | Saxena et al. | |
| 5,075,222 A | 12/1991 | Hannum et al. | |
| 5,089,261 A | 2/1992 | Nitecki et al. | |
| 5,093,475 A | 3/1992 | Carroll et al. | |
| 5,116,964 A | 5/1992 | Capon et al. | |
| 5,122,614 A | 6/1992 | Zalipsky | |
| 5,136,021 A | 8/1992 | Dembinski et al. | |
| 5,153,265 A | 10/1992 | Shadle et al. | |
| 5,162,430 A | 11/1992 | Rhee et al. | |
| 5,166,322 A | 11/1992 | Shaw et al. | |
| 5,171,264 A | 12/1992 | Merrill | |
| 5,211,945 A | 5/1993 | Wallach et al. | |
| 5,214,131 A | 5/1993 | Sano et al. | |
| 5,252,714 A | 10/1993 | Harris et al. | |
| 5,344,915 A | 9/1994 | LeMaire et al. | |
| 5,350,836 A * | 9/1994 | Kopchick et al. | ........... 530/399 |
| 5,359,032 A | 10/1994 | Dayer et al. | |
| 5,359,037 A | 10/1994 | Wallach et al. | |
| 5,382,657 A | 1/1995 | Karasiewicz et al. | |
| 5,395,760 A | 3/1995 | Smith et al. | |
| 5,446,090 A | 8/1995 | Harris | |
| 5,453,490 A | 9/1995 | Hageman et al. | |
| 5,478,925 A | 12/1995 | Wallach et al. | |
| 5,512,544 A | 4/1996 | Wallach et al. | |
| 5,569,779 A | 10/1996 | Sabahi et al. | |
| 5,605,690 A | 2/1997 | Jacobs et al. | |
| 5,610,279 A | 3/1997 | Brockhaus et al. | |
| 5,633,145 A | 5/1997 | Feldmann et al. | |
| 5,681,566 A | 10/1997 | Stevenson | |
| 5,695,953 A | 12/1997 | Wallach et al. | |
| 5,712,155 A | 1/1998 | Smith et al. | |
| 5,739,208 A | 4/1998 | Harris | |
| 5,747,639 A | 5/1998 | Seely | |
| 5,808,029 A | 9/1998 | Brockhaus et al. | |
| 5,811,261 A | 9/1998 | Wallach et al. | |
| 5,863,786 A | 1/1999 | Feldmann et al. | |
| 5,958,409 A | 9/1999 | Turk et al. | |

FOREIGN PATENT DOCUMENTS

CA   2003743   5/1990

(Continued)

OTHER PUBLICATIONS

US 5,843,791, 12/1998, Hauptmann et al. (withdrawn)
Chen et al., Journal of Biological Chemistry, vol. 270, No. 6, pp. 2874–2878, Feb. 1995.*

(Continued)

*Primary Examiner*—Brenda Brumback
*Assistant Examiner*—Eileen B O'Hara
(74) *Attorney, Agent, or Firm*—McDonnell Boehnen Hulbert & Berghoff

(57) ABSTRACT

Disclosed are novel proteins, referred to as tumor necrosis factor binding proteins, that modulate the activity of tumor necrosis factor. Also disclosed are processes for obtaining the tumor necrosis binding proteins by recombinant genetic engineering techniques.

27 Claims, 13 Drawing Sheets

FOREIGN PATENT DOCUMENTS

| | | |
|---|---|---|
| DE | 39 10 323 A1 | 10/1989 |
| EP | 0 040 506 B1 | 11/1981 |
| EP | 0 092 918 A2 | 11/1983 |
| EP | 0 094 844 A2 | 11/1983 |
| EP | 0 154 316 A2 | 9/1985 |
| EP | 0 169 112 B1 | 1/1986 |
| EP | 0 225 579 A3 | 6/1987 |
| EP | 0 247 860 A2 | 12/1987 |
| EP | 0 259 863 A2 | 3/1988 |
| EP | 0 308 378 A2 | 3/1989 |
| EP | 0 154 316 B1 | 9/1989 |
| EP | 0 334 165 A2 | 9/1989 |
| EP | 0 343 684 B1 | 11/1989 |
| EP | 0 372 752 A2 | 6/1990 |
| EP | 0 386 289 A1 | 9/1990 |
| EP | 0 393 438 A2 | 10/1990 |
| EP | 0 395 853 A1 | 11/1990 |
| EP | 0 398 327 A1 | 11/1990 |
| EP | 0 412 486 A1 | 2/1991 |
| EP | 0 417 563 A2 | 3/1991 |
| EP | 0 418 014 A1 | 3/1991 |
| EP | 0 422 339 A1 | 4/1991 |
| EP | 0 433 900 A1 | 6/1991 |
| EP | 0 512 528 A2 | 11/1992 |
| EP | 0 526 905 A2 | 2/1993 |
| EP | 0 622 394 A1 | 11/1994 |
| GB | 2 218 101 A | 11/1989 |
| GB | 2 246 569 A | 2/1992 |
| IL | 90339 | 5/1989 |
| JP | 02040399 A | 2/1990 |
| JP | 62-185029 A | 8/1997 |
| WO | WO 87/00056 A1 | 1/1987 |
| WO | WO 88/00837 A2 | 2/1988 |
| WO | WO 89/05145 A1 | 6/1989 |
| WO | WO 89/06546 A1 | 7/1989 |
| WO | WO 89/09220 A1 | 10/1989 |
| WO | WO 90/04413 A1 | 5/1990 |
| WO | WO 90/04650 A1 | 5/1990 |
| WO | WO 90/05755 A1 | 5/1990 |
| WO | WO 90/12874 A2 | 11/1990 |
| WO | WO 90/13575 A1 | 11/1990 |
| WO | WO 91/03553 A1 | 3/1991 |
| WO | WO 91/05047 A1 | 4/1991 |
| WO | WO 91/07190 A1 | 5/1991 |
| WO | WO 91/16437 A1 | 10/1991 |
| WO | WO 92/01002 A1 | 1/1992 |
| WO | WO 92/01472 A1 | 2/1992 |
| WO | WO 92/01474 A1 | 2/1992 |
| WO | WO 92/04384 A1 | 3/1992 |
| WO | WO 92/07076 A1 | 4/1992 |
| WO | WO 92/13095 A1 | 8/1992 |
| WO | WO 92/15682 A1 | 9/1992 |
| WO | WO 92/16221 | * 10/1992 |
| WO | WO 92/16221 A1 | 10/1992 |
| WO | WO 92/16555 A1 | 10/1992 |
| WO | WO 93/01498 A1 | 1/1993 |
| WO | WO 94/01483 A1 | 1/1994 |
| WO | WO 94/06476 A1 | 3/1994 |
| WO | WO 94/06058 A1 | 3/1995 |
| WO | WO 95/13312 A1 | 5/1995 |
| WO | WO 95/34326 A1 | 12/1995 |
| WO | WO 96/19459 A1 | 6/1996 |
| WO | WO 97/32607 A2 | 9/1997 |

OTHER PUBLICATIONS

The Cytokine Facts Book, Callard and Gearing, Eds., Academic Press, 1994.*

Abuchowski, et al., "Effect of Covalent Attachment of Polyethylene Glycol on Immunogenicity and Circulating Life of Bovine Liver Catalase," *Journal of Biological Chemistry*, 252 (11): 3582–3586 (1977).

Aggarwal, et al., "Characterization of Receptors for Human Tumour Necrosis Fator and Their Regulation by Γ– Interferon", *Nature*, 318: 665–667 (1985).

Akerblom, et al., "Preparation and Characterization of Conjugates of Monoclonal Antibodies and Staphylococcal Enterotoxin A Using a New Hydrophilic Cross–Linker," *Bioconjugate Chem.*, 4:455–466 (1993).

Anderson, et al., "Quantitative Filter Hybridisation," Nucleic Acid Hybridization: A Practical Approach, Hawes, et al. (ed)., pp. 73–111 (1985).

Ashkenazi, et al., "Protection Against Endotoxic Shock by a Tumor Necrosis Factor Receptor Immunoadhesin," *PNAS* 88: 10535–10539 (1991).

Baglioni, et al., "Binding of Human Tumor Necrosis Factor to High Affinity Receptors on HeLa and Lymphoblastoid Cells Sensitive to Growth Inhibition," *Journal of Biological Chemistry*, 260 (25): 13395–13397 (1985).

Baker, et al., "Inhibition of EAE by TNF–Receptor Fusion Proteins," *J. Neuroimmunology*, 54 (1–2): 151 Abstract P16.01 (1992).

Bakouche, et al., "Plasma Membrane–Associate Tumor Necrosis Factor, A Non–Integral Membrane Protein Possibly Bound to Its Own Receptor", *J. Immunol.* 140: 1142–1147 (1988).

Banner, et al., "Crystal Structure of the Soluble Human 55 kD TNF Receptor–Human TNFβ Complex: Implications for TNF Receptor Activation", *Cell*. 73: 431–445 (1993).

Beutler, et al., "Passive Immunization against Cachectin/Tumor Necrosis Factor Protects Mice from Lethal Effect of Endotoxin", *Science*, 229:869–871 (1985).

Beutler and Cerami, "The Biology of Cachectin/TNF–A Primary Mediator of the Host Response", *Ann. Rev. Immunol.*, 7:625–655 (1989).

Bevilacqua, et al., "Recombinant tumor necrosis factor induces procoagulant activity in cultured human vascular endothelium: Characterization and comparison with the actions of interleukin 1," *Proc. Natl. Acad. Sci. USA*, 83: 4533–4537 (1986).

Binkert, et al., "Cloning, Sequence Analysis and Expression of a cDNA Encoding a Novel Insulin–like Growth Factor Binding Protein (IGFBP–2)," *The EMPO J.* 8 (9):2497–2502 (1989).

Bourdon, et al., "Structure–function Relationships of Hirulog Peptide Interactions with Thrombin," *FEBS* 294:163–166 (1991).

Bowie, et al., "Deciphering the Message in Protein Sequences: Tolerance to Amino Acid Substitutions," *Science*, 247: 1306–1310 (1990).

Brakebusch, et al., "Diverse Functions of the Tumor Necrosis Factor Receptors: Structure–Activity Considerations," *Tumor Necrosis Factor: Molecular and Cellular Biology and Clinical Relevance*, pp. 40–51 (1993).

Brennan, et al., "Inhibitory Effect of the TNFα Antibodies on Synovial Cell Interleukin–1 Production in Rheumatoid Arthritis," Lancet, vol. 2 (8657), pp. 224–247 (1989).

Brockhaus, et al., "Identification of Two Types to Tumor Necrosis Factor Receptors on Human Cell Lines by Monoclonal Antibodies," *Proc. Natl. Acad. Sci. USA*, 87:3127–3131 (1990).

Butler, et al., "TNF Receptor Fusion Proteins are Effective Inhibitors of TNF–Mediated Cytotoxicity on Human KYM–1D4 Rhabdomyosarcoma Cells," *Cytokine*, 6 (6): 616–623 (1994).

Byrn, et al., "Biological Properties of a CD4 Immunoadhesin," *Nature (London)* 344:667–670 (1990).

Capaldi, et al., "Changes in Order of Migration of Polypeptides in Complex III and Cytochrome c Oxidase under Different Conditions of SDS Polyacrylamide Gel Electrophoresis," *Biochem. & Biophys. Res Comm.* 74 (2):425–433 (1977).

Carlino, et al., "Use of a Sensitive Receptor Binding Assay to Discriminate Between Full–Length and Truncated Human Recombinant TNF Proteins," *J. Biol. Chem.* 262 (3):958–961 (1987).

Carrieri, et al., "Cytokines in the Pathogenesis of Multiple Sclerosis," *Acta Neurologica*, 14 (4–6): pp. 333–341 (1992).

Chaudhary, et al., "A Recombinant Immunotoxin consisting of two antibody variable domains fused to Pseudomonas exotoxin," *Nature*, 339:394–397 (1989).

Chen, et al., "Production of Multimeric Forms of CD4 Through a Sugar–based Cross linking Strategy," *J. Biol. Chem.*, 266 (27): 18237–18243 (1991).

Chih–Hsueh Chen P., et al., "Mapping the Domain(s) Critical for the Binding of Human Tumor Necrosis Factor–Alpha to its Two Receptors," *The Journal of Biological Chemistry*, 240 (6): 2874–2878 (Feb. 10, 1995).

Colletti, et al., "The Production of Tumor Necrosis Factor Alpha and the Development of a Pulmonary Capillary Injury Following Hepatic Ischemia/Reperfusion," *Transplantation* 49 (2): 268–272 (1990).

Conforti, et al., "PEG Superoxide Dismutase Derivatives: Anti–inflammatory Activity in Carrageenan Pelurisy in Rats." *Pharmacological Research Communications*, 19 (4): 287–294 (1987).

Corcoran. et al., "Characterization of Ligand Binding by the Human p55 Tumor–Necrosis–Factor Receptor Involvement of Individual Cysteine–Rich Repeats." *Eur. J. Biochem.*, 223:831–840 (1994).

Creasey, et al., "A High Molecular Weight Component of the Human Tumor Necrosis Factor Receptor is Associated with Cytotoxicity," *Proc. Natl. Acad. Sci. USA*, 84: 3293–3297 (1987).

Davis, et al., "Soluble, nonantigenic Polyethylene Glycol–Bound Enzymes," *Biomedical Polymers: Polymeric Materials and Pharmaceuticals for Biomedical Use*, Goldberg, et al. (Ed.). published by Academic Press (NY), pp. 441–452 (1980).

Dayer, et al., "Purification and Characterization of Human Tumor Necrosis Factor α Inhibitor," *Chemical Abstracts*, 113 (38760n): 454 (1990).

Dayer, et al., "Interleukin–1, Tumor Necrosis Factor and Their Specific Inhibitors," *European Cytokine Network*. 5 (6): 563–571.

Delgado, et al., "The Uses and Properties of PEG–Linked Proteins," *Critical Reviews in Therapeutic Drug Carrier Systems*, 9 (3,4): 249–304 (1992).

Dembic, et al., "Two Human TNF Receptors Have Similar Extracellular, But Distinct Intracellular, Domain Sequences," *Cytokine*, 2 (4): 231–237 (1990).

Dohlsten, et al., "Monoclonal Antibody–targeted Superantigens: A Different Class of Anti–tumor Agents," *Proc. Natl. Acad. Sci. USA*, 88: 9287–9291 (1991).

Eisenberg, et al., "Primary Structure and Functional Expression from complementary DNA of a Human Interleukin–1 Receptor Antagonist," *Nature*, 343: 341–346 (1990).

Elliot, et al., "Randomised Double–blind Comparison of Chimeric Monoclonal Antibody to Tumour Necrosis Factor α (cA2) versus Placebo in Rheumatoid Arthritis," *Lancet*, 344: 1105–1110 (1994).

Englemann, et al., "A Tumor Necrosis Factor–Binding Protein Purified to Homogeneity from Human Urine Protects Cells from Tumor Necrosis Factor Toxicity," *J. Biol. Chem.*, 264 (20): 11974–11980 (1989).

Englemann, et al., "Antibodies to a Soluble Form of a Tumor Necrosis Factor (TNF) Receptor have TNF Like Activity," *Journal of Biological Chemistry*, 265 (24): 14497–14504 (1990).

Englemann, et al., "Two Tumor Necrosis Factor–Binding Proteins Purified From Human Urine," *J. Biol. Chem.*, 265 (3): 1531–1536 (1990).

Erez, et al., "Narcotic Antagonistic Potency of Bivalent Ligands Which Contain β–Naltrexamine Evidence for Bridging Between Proximal Recognition Sites," *J. Med. Chem.*, 25: 847–849 (1982).

Espevik, et al., "Characterization of Binding and Biological Effects of Monoclonal Antibodies Against a Human Tumor Necrosis Factor Receptor," *Journal Exp. Med.*, 171: 415–426 (1990).

Evans, Ronald M., "The Steroid and Thyroid Hormone Receptor Superfamily," *Science* 240: 889–895 (1998).

Feldman, et al., "Receptor Activation by Antigens, Cytokines, Hormones, and Growth Factors," *Annals of The New York Academy of Sciences*, 766: 272–278 (1995).

Fisher, et al., "Treatment of Septic Shock with the Tumor Necrosis Factor Recptor: Fc Fusion Protein," *The New England Journal of Medicine*, 334 (26): 1697–1702 (1996).

Frohman, et al., "Rapid production of full–length cDNAs from rare transcripts: Amplification using a single gene–specific oligonucleoide primer," *Proc. Natl. Acad. Sci. USA* 85: 8998–9002 (1988).

Fu Z.–Q.: "Model Complexes of Tumor Necrosis Factor–Alpha with Receptors R1 and R2," *Protein Engineering*, 8 (12): 1233–1241 (1995).

Gatanaga, et al., "Purification and Characterization of an Inhibitor (Soluable Tumor Necrosis Factor Receptor) for Tumor Necrosis Factor and Lymphotoxin Obtained from the Serum Ultrafiltrates of Human Cancer Patients," *Proc National Academy of Science* USA 87: 8781–8784.

Glass, et al., "4–Phenoxy–3, 5–Dinitrobenzoylpolyethyleneglycol: Reversible Attachment of Cysteine–Containing Polypeptides to Polymers in Aqueous Solutions," *Biopolymers*, 18: 383–392 (1979).

Goodson, et al., "Site–Directed Pegylation of Recombinant Interleukin–2 At Its Glycosylation Site," *Bio Technology*, 8: 343–346 (1990).

Goodwin, et al., "Molecular Cloning and Expression of the Type 1 and Type 2 Murine Receptors for Tumor Necrosis Factor," *Molecular and Cell Biology* 11 (6): 3020–3026 (1991).

Gray, et al., "Cloning of Human Tumor Necrosis Factor (TNF) Receptor cDNA and Expression of Recombiant soluble TNF–Binding Protein," *Proc. Natl. Acad. Sci. USA*, 87 (19): 7380–7384 (1990).

Grizzard, et al., "Affinity–Labeled Somatomedin–C Receptors and Binding Proteins From the Human Fetus," *Journal of Clinical Endocrinology and Metabolism*, 58 (3): 535–543 (1984).

Hale, et al., Cytokines and Their Receptors: From Clonal to Clinical Investigation–"Demonstration of in Vitro and in Vivo Efficacy of Two Biologically Active Human Soluble TNF Receptors Expressed in *E. Coli*," *J. Cell. Biochem.*, Suppl. 15F: 113 (1991).

Hannum, et al., "Interleukin–1 Receptor Antagonist Activity of a Human Interleukin–1 Inhibitor," *Nature*, 343 (6256): 336–340 (1990).

Harris Milton, "Laboratory Synthesis of Polyethylene Glycol Derivatives," *Rev. Macromol. Chem. Phys.*, 25 (3): 325–373 (1985).

Harris, et al., "Synthesis and Characterization of Poly (ethylene Glycol) Derivatives," *Journal of Polymer Science: Polymer Chemistry Edition*, 22: 341–352 (1984).

Hass, et al., "Characterization of Specific High Affinity Receptors for Human Tumor Necrosis Factor on Mouse Fibroblasts," *J. Biol. Chem.* 260(22): 12214–12218 (1985).

Hatakeyama, et al., "Interleukin–2 Receptor β Chain Gene: Generation of Three Receptor Forms by Cloned Human α and β Chain cDNA's," *Science* 244: 551–556 (1989).

Hauser, et al., "Cytokine Accumulations in CSF of Multiple Sclerosis Patients: Frequent Detection of Interleukin–1 and Tumor Necrosis Factor but not Interleukin–6," *Neurology* 40: 1735–1739 (1990).

Heller, et al., "Amplified Expression of Tumor Necrosis Factor Receptor in Cells Transfected iwth Espstein–Barr Virus Shuttle Vector cDNA Libraries," *J. Biol. Chem.*, 265 (10): 5708–5717 (1990).

Heller, et al., "Complementary DNA Cloning of a Receptor for Tumor Necrosis Factor and Demonstration of a Shed Form of the Receptor," *Proc. Natl. Acad. Sci. USA*, 87: 6151–6155 (1990).

Himmler, et al., "Molecular Cloning & Expression of Human & Rat Tumor Necrosis Factor Receptor Chain (p 60) and its Soluable Derivative, Tumor Necrosis Factor–Binding Protein," *DNA and Cell Biology*, 9 (10): 705–715 (1990).

Hoes, et al., "Optimization of Macromolecular Prodrugs of the Antitumor Antibiotic Adriamycin," *Journal of Controlled Release*, 2: 205–213 (1985).

Hofman, et al., "Tumor Necrosis Factor Identified in Multiple Sclerosis Brain," *J. Exp. Med.* 170: 607–612 (1989).

Hohmann, et al., "Two Different Cell Types Have Different Major Receptors for Human Necrosis Factor (TNF α)." *Journal of Biol. Chem.* 264: 14927–14934 (1989).

Horner, et al., "Aryl–vinlysulfone–reagentien Zum Shutz Und Nacheweis Von Thiofunkitonen," *Phosphorus and Sulfur* 15: 1–8 (1983).

Israel, et al., "Binding of Human TNF–α to High–Affinity Cell Surface Receptors: Effect of IFN," *Immunol. Lett.* 12: 217–224 (1986).

Jenkins, et al., "Tumor Necrosis Factor Causes an Increase in Axonal Transport of Protein and Demyelination in the Mouse Optic Nerve," *Journal of Neurological Science*, 108: 99–104 (1992).

Jiang, et al., "Defined Chemically Cross–Linked Oligomers of Human C–Reactive Protein: Characterization and Reactivity with the Complement System," *Immunology*, 74: 725–731 (1991).

Johansson, Gote, "Studies on Aqueous Dextran–Poly (Ethylene Glycol) Two–Phase Systems Containing Charged Poly (Ethylene Glycol)," *Giochimica Et Biophysica Acta*, 222: 381–389 (1970).

Kalli, et al., "Mapping of the C3b–binding Site of CR 1 and Construction of a (CR 1)$_2$–F(ab$^1$)$_2$ Chimeric Complement Inhibitor," *J. Exp. Med.* 174: 1451–1460 (1991).

Kasukabe, et al., "Purification of a Novel Growth Inhibitory Factor for Partially Differentiated Myeloid Leukemic Cells," *Journal of Biol. Chem.* 263 (11): 5431–5435 (1988).

Katre, et al., "Chemical Modification of Recombinant Interleukin 2 by polyethylene glycol increases its potency in the murine Meth A Sarcome model," *Proc. Natl. Acad. Sci. USA*, 84:1487–1491 (1987).

Knauf, et al., "Relationship of Effective Molecular Size to Systematic Clearance in Rats of Recombinant Interleukin–2 Chemically Modified with Water–soluble Polymers," *The Journal of Biological Chemistry*, 263 (29): 15064–15070 (1988).

Kogan, Timothy, "The Synthesis of Substituted Methoxy–Poly (EthyleneGlycol) Derivatives Suitable for Selective Protein Modification," *Synthetic Communications*, 22 (16): 2417–2424 (1992).

Kohgo, et al., "Circulating Transferrin Receptor in Human Serum," *British Journal of Haematology*, 64: 277–281 (1986).

Kohno, et al., "A Second Tumor Necrosis Factor Receptor Gene Product Can Shed a Naturally Occurring Tumor Necrosis Factor Inhibitor," *Proc. Natl. Acad. Sci. USA*, 87: 8331–8335 (1990).

Kull, et al., "Cellular Receptor for $^{125}$I–Labeled Tumor Necrosis Factor: Specific Binding, Affinity Labeling, and Relationship to Sensitivity," *Proc. Natl. Acad. Sci. USA*, 82: 5756–5760 (1985).

Kuroki, et al., "Aryl Vinyl Sulfones as Thiol Protective Group," *Tetrahedron Letters*, 25 (2): 197–200 (1984).

Lantz, et al., "Characterization In Vitro of Human Tumor Necrosis Factor–Binding Protein," *J. Clin. Invest.*, 86: 1396–1402 (1990).

Le, et al., "Tumor Necrosis Factor and Interleukin 1: Cytokines with Multiple Overlapping Biological Activities," *Lab Investigation* 56 (3): 234–248 (1987).

Lee, et al., Generation of cDNA Probes Directed by Amino Acid Sequence: Cloning of Urate Oxidase Science 239: 1288–1291 (1988).

Lehmann, et al., "Demonstration of Membrane Receptors for Human Natural Recombinant $^{125}$I–Labeled Tumor Necrosis Factor on HeLa Cell Clones and Their Role in Tumor Cell Sensitivity," *Eur. J. Biochem.* 158: 1–5 (1986).

Leung, et al., "Growth Hormone Receptor and Serum Binding Protein: Purification, Cloning and Expression," *Nature* 330:537–543 (1987).

Liao, et al., "Characterization of a Human Interleukin 1 Inhibitor," *J. Immunol.*, 134 (6): 3882–3886 (1985).

Liao, et al., "Identification of a Specific Interleukin 1 Inhibitor in the Urine of Febrile Patients," *J. Exp. Med.* 159: 126–136 (1984).

Liblau, et al., "Tumor Necrosis Factor–α and Disease Progression in Multiple Sclerosis," *New Engl. J. Med.* 326 (4): 272–273 (1992).

Lindvall, et al., "Modulation of the Constitutive Gene Expression of the 55 KD Tumor Necrosis Factor Receptor in Hematopoietic Cells," *Biochem. & Biophys. Res. Comm.* 172 (2) 557–563 (1990).

Loetscher, et al., "Molecular Cloning Expression of the Human 55kd TNF Necrosis Factor Receptor," *Cell.* 61: 351–359 (1990).

Loetscher, et al., "Recombinant 55–kDa Tumor Necrosis Factor (TNF) Receptor," *J. Biol. Chem.* 266(27): 18324–18329 (1991).

Marangonore, et al., "Design and Characterization of Hirulogs: A Novel Class of Bivalent Peptide Inhibitors of Thrombin," *Biochemistry*, 29: 7095–7101 (1990).

March, et al., "Cloning, Sequence and Expression of Two Distinct Human Interleukin–1 Complementary DNAs," *Nature* 315: 641–647 (1985).

Marsters S.A., et al., "Identification of Cystein–Rich Domains of the Type 1 Tumor Necrosis Factor Receptor Involved in Ligand Binding," The Journal of Biological Chemistry, 267 (9): 5747–5750 (Mar. 25, 1992).

Martin, et al., "Inhibition of Tumor Necrosis Factor is Protective Against Neurologic Dysfunction After Active Immunization of Lewis Rats with Myelin Basic Protein," *Exp. Neurol*, 131: 221–228 (1995).

McFarland, Henry, "Therapeutic Approaches to Multiple Sclerosis," *J. Neurochem.*, 64 (Suppl.): S73 (Abstract C) (1995).

Monastra, et al., "Phosphatidylserine, a Putative Inhibitor of Tumor Necrosis Factor, Prevents Autoimmune Demyelination," *Neurology*, 43: 153–163 (1993).

Murata, et al., "Ingibitory Effect of a Synthetic Polypeptide, poly(Tyr–lle–Gly–Ser–Arg), On the Metastatic Formation of Malignant Tumour Cells," *Int. J. Biol. Macromol.*, 11:97–99 (1989).

Neda, Hiroshi, "Analysis of the Tumor Necrosis Factor (TNF) Receptor of Various Tumor Cells," *Sapporo Medical Journal*, 56 (2): 305–317 (1987).

Nexo, et al., "Lectin–Agarose Immobilization, a New Method for Detecting Soluble Membrane Receptors," *J. Biol. Chem.* 254 (18): 8740–8743 (1979).

Nophar, et al., "Soluble forms of tumor necrosis factor receptors (TNF–Rs). The cDNA for the type I TNF–R, cloned using amino acid sequence data of its soluble form, encodes both the cell surface and a soluble form of the receptor," *The EMBO J.*, 3(10): 3269–3278 (1990).

Novick, et al., "Soluble Cytokine Receptors are Present in Normal Human Urine," *J. Exp. Med.* 170: 1409–1414 (1989).

Novick, et al., "Soluble Cytokine Receptors are Present in Normal Human Urine," *The Physiological and Pathological Effects of Cytokines*, pp. 413–421 (1990).

Novick, et al., "Purification of Soluble Cytokine Receptros from Normal Human Urine by Ligand–Affinity and Immunoaffinity Chromatography," *J. Chromatog.* 510: 331–337 (1990).

Oliff, et al., "Tumors Secreting Human TNF/Cachectin Induce Cachexia In Mice," *Cell,* 50: 555–563 (1987).

Olsson, et al., "Isolation and Characterization of a Tumor Necrosis Factor Binding Protein from Urine," *Eur. J. Haematology*, 42 (3): 270–275 (1989).

Paleolog, et al., "Deactivation of Vascular Endothelium By Monoclonal Anti–Tumor Necrosis Factor α Antibody in Rheumatoid Arthritis," *Arthritis and Rheumatism*, 39:1082–1091 (1996).

Peetre, et al., "A Tumor Necrosis Factor Binding Protein is Present in Human Biological Fluids," *Eur. J. Haematology*, 41: 414–419 (1988).

Pennica, et al., "Biochemical Properties of the 75–kDa Tumor Necrosis Factor Receptor," Journal of Biological Chemistry, 267 (29): 21172–21178 (1992).

Peppel, et al., "A Tumor Necrosis Factor (TNF) Receptor–IgG Heavy Chain Chimeric Protein as a Bivalent Antagonist of TNF Activity," *J. Exp. Med.*, 174: 1483–1489 (1991).

Piguet, et al., "Tumor Necrosis Factor/Cachectin Plays a Key Role in Bleomycin–Induced Pneumophathy and Fibrosis," *J. Exp. Med.*, 170: 655–663 (1989).

Portoghese, et al., "Opioid Agonist and Antagonist bivalent Ligands. The Relationship Between Spacer Length and Selectivity at Multiple Opioid Receptors," *J. Med. Chem.*, 29: 1855–1861 (1986).

Powell, et al., "The Role of Lymphotoxin and TNF in Demyelinating Diseases of CNS," *Tumor Necrosis Factors: The Molecules and Their Emerging Role in Medicine*, ed. By B. Beutler, Raven Press, New York, pp. 355–369 (1992).

Powell, et al., "Lymphotoxin and Tumor Necrosis Factor–Alpha Production by Myelin Basic Protein–Specific T Cell Clones Correlates with Encephalitogenicity," *International Immunology*, 2 (6): 539–544 (1990).

Rankin, et al., "The Therapeutic Effects of an Engineered Human Anti–Tumour Necrosis Factor Alpha Antibody (CDP571) in Rheumatoid Arthritis," *British Journal of Rheumatology*, 34: 334–342 (1995).

Rhein, Reginald., "Another Sepsis Drug Down–Immunex' TNF Receptor," Biotechnology *Newswatch*, pp. 1–3 (Monday, Oct. 4, 1993).

Romani, et al., "Synthesis of unsymmetrical Cystine Peptides: Directed Disulfide Pairing with the Sulfenohydrazide Method," *Chemistry of Peptides and Proteins*, 2: 29–34 (1984).

Rosenstreich, et al., "A Human Urine–Derived Interleukin 1 Inhibitor," *J. Exp. Med.*, 168: 1767–1779 (1988).

Ruddle, et al., "An Antibody to Lympotoxin and Tumor Necrosis Factor Prevents Transfer of Experimental Allergic Encephalomyelitis," *J. Exp. Med.* 172: 1193–1200 (1990).

Scallon, et al., "Functional Comparisons of Different Tumor Necrosis Factor Receptor/IgG Fusion Proteins," *Cytokine*, 7(8): 759–770 (1995).

Schall, et al., "Molecular Cloning and Expression of a Receptor for Human Tumor Necrosis Factor," *Cell*, 61: 361–370 (1990).

Scheurich, et al., "Quantification and Characterization of High–Affinity Membrane Receptors for Tumor Necrosis Factor on Human Leukemic Cell Lines," *Int. J. Cancer* 38 (1): 127–133 (1986).

Seckinger, et al., "A Human Inhibitor of Tumor Necrosis Factor Alpha," *J. Exp. Med.*, 167: 1511–1516 (1988).

Seckinger, et al., "A Urine Inhibitor of Interleukin 1 Activity Affects Both Interleukin 1 α and 1 β But Not Tumor Necrosis Factor α," *J. Immunol.* 139 (5): 1541–1545 (1987).

Seckinger, et al., "Characterization of a Tumor Necrosis Factor α (TNF–α) Inhibitor: Evidence of Immunological Cross–Reactivity with the TNF Receptor," *Proc. Natl. Acad. Sci. USA*, 87: 5188–5192 (1990).

Seckinger, et al., "Purification and Biologic Characterization of a Specific Tumor Necrosis Factor α Inhibitor," *J. Biol. Chem.*, 264 (20): 11966–11973 (1989).

Seckinger, et al., "A Urine Inhibitor of Interleukin 1 Activity That Blocks Ligand Binding," *J. Immunol.*, 139 (5): 1546–1549 (1987).

Seely, et al., "Manufacturing of Recombinant Tumor Necrosis Factor Binding Protein 'Dumbell' Using a 20K PEG BIS Vinylsulfone Linker," 209 Am. Chem. Soc. National Meeting, Anaheim, Cal., Apr. 2–6, 1995, BIOT 68.

Selby, et al., "Endogeneous Tumor Necrosis Factor in Cancer Patients," *Lancet*, 1 (8583): 483 (1988).

Selmaj, et al., "Anti–Tumor Necrosis Factor Therapy Abrogates Autoimmune Demyelination," *Annals of Neurology by Am. Neurol. Assoc.*, 30 (5): 694–700 (1991).

Selmaj, et al., "Prevention of CHR–EAE with Soluble TNF Receptor P55," *J. Neuroimmunology*, 54 (12): 196. Abstract W15.05 (1994).

Selmaj, et al., "Prevention of Chronic Relapsing Experimental Autoimmune encephalomyelitis by Soluble Tumor Necrosis Factor Receptor I," *J. Neuroimmunology*, 56: 135–141 (1995).

Selmaj, et al., "Proliferation of Astrocytes in Vitro in Response to Cytokines: A Primary Role for Tumor Necrosis Factor," *J. Immunol.* 144 (1): 129–135 (1990).

Selmaj, et al., "Tumor Necrosis Factor Mediates Myelin and Oligodendrocyte Damage in Vitro," *Annals of Neurology* 23(4): 339–346 (1998).

Sharief, et al., "Association Between Tumor Necrosis Factor–Alpha and Disease Progression in Patients with Multiple Sclerosis," *New England J of Med.* 325 (7): 467–472 (1991).

Shimohigashi, et al., "Dimeric Tetrapeptide Enkephalins Display Extraordinary Selectivity for the Δ Opiate Receptor," *Nature*, 297: 333–335 (1982).

Smith, Craig, "cDNA Expression: Cloning of the Receptor for Human Tumor Necrosis Factor," Presentation Programme, 29$^{th}$ Midwinter Conference of Immunologists (Jan. 27–30, 1990).

Smith, Craig, "cDNA Expression: Cloning of the Receptor for Human Tumor Necrosis Factor," Presentation at the 29$^{th}$ Midwinter Conference of Immunologists (Jan. 27–30, 1990).

Smith, et al., "A Receptor for Tumor Necrosis Factor Defines as unusual Family of Cellular and Viral Proteins," *Science*, 248: 1019–1023 (1990).

Smith, et al., "A Receptor for Tumor Necrosis Factor Defines as Unusual Family of Cellular and Viral Proteins," Genbank database excerpt released after publication (May 1990).

Smith, et al., "Species Specificity of Human and Murine Tumor Necrosis Factor," *J. Biol. Chem.*, 261 (32): 14871–14874 (1986).

Socher, et al., "Antibodies Against Amino Acids 1–15 of Tumor Necrosis Factor Block Its Binding Cell–Surface Receptor," *Proc. Natl. Acad. Sci.* USA 84: 8829–8833 (1987).

Spinas, et al., "Induction of Plasma Inhibitors of Interleukin 1 and TNF–Alpha Activity by Endotoxin Administration to Normal Humans," *Am. J. Physiol.* 259: R993–R997 (1990).

Starnes, Jr., et al., "Tumor Necrosis Factor and the Acute Metabolic Response to Tissue Injury in Man," 82: 1321–1325 (1988).

Stauber, et al., "Human Tumor Necrosis Factor–α Receptor," *J. Biol. Chem.*, 263 (35): 19098–19104 (1988).

Stauber, et al., "Characterization and Affinity Cross–Linking of Receptors for Human Recombinant Lymphotoxin (Tumor Necrosis Factor–β) on a Human Histiocytic Lymphoma Cell Line U–937," J. Biol. Chem. 264 (6): 3573–3576 (1989).

Suffys, et al., "Involvement of a Serine Protease in Tumour–Necrosis–Factor–Mediated Cytotoxicity," *Eur. J. Biochem.* 178: 257–265 (1988).

Suggs, et al., "Use of Synthetic Oligonucleotides as Hybridization Probes: Isolation of Cloned cDNA Sequences for Human β 2–Microglobulin," *Proc. Natl. Acad. Sci.* U.S.A. 78(11): 6613–6617 (1981).

Suzuki, et al., "Physicochemical and Biological Properties of Poly (Ethylene Glycol)–Coupled Immunoglobulin G," *Biochimica et Biophysica Acta.*, 788: 248–255 (1984).

Tak, et al., "Decrease in Cellularity and Expression of Adhesion Molecules by Anti–tumor Necrosis Factor α Monoclonal Antibody Treatment in Patients with Rheumatoid Arthritis," *Arthritis and Rheumatism*, 39: 1077–1081 (1996).

The Cytokine Factsbook, Callard (ed.), Academic Press, Inc., San Diego, CA., pp. 244–246 (1994).

Tracey, et al., "Anti–Cachectin/TNF Monoclonal Antibodies Prevent Septic Shock During Lethal Bacteraemia," *Nature* 330: 662–664 (1987).

Tracey, et al., "Cachectin/Tumor Necrosis Factor Induces Cachexia, Anemia, and Inflammation," *J. Exp. Med.* 167: 1211–1227 (1988).

Tracey, et al., "Metabolic Effects of Cachectin/Tumor Necrosis Factor Are Modified by Site of Production," *J. Clon Invest.* 86: 2014–2024 (1990).

Tracey, et al., "Physiological Responses to Cachectin," Tumor necrosis factor and related cytotoxins. Wiley, Chichester (*Ciba Foundation Symposium 131*), pp. 88–108 (1987).

Tsujimoto, et al., "Characterization and Affinity Crosslinking of Receptors for Tumor Necrosis Factor on Human Cells," *Archives of Biochem. & Biophys.* 249 (2): 563–568 (1986).

Unglaub, et al., "Downregulation of Tumor Necrosis Factor (TNF) Sensitivity Via Modulation of TNF Binding Capacity by Protein Kinase C Activators," *J. Exp. Med.* 166: 1788–1797 (1987).

Van Zee, et al., "Tumor Necrosis Factor Soluble Receptors Circulate During Experimental and Clinical Inflammation and Can Protect Against Excessive Tumor Necrosis Factor α In Vitro and In Vivo," *Proc. Natl. Acad. Sci. USA*, 89: 4845–4849 (1992).

Vilcek, et al., "Tumor Necrosis Factor: Receptor Binding and Mitogenic Action in Fibroblasts," *Journal of Cellular Physiology Supplement* 5: 57–61 (1987).

Vitt, et al., "Biological and Structural Characterization of the Tumor Necrosis Factor Receptor on Multiple Cell Types: Relationship to Function," Fed. Proc. 78$^{th}$ Annual Meeting of the American Society of Biological Chemists 46 (6): 2117 (Abstract 1118) (1987).

Waage, et al., "Association Between Tumour Necrosis Factor in Serum and Fatal Outcome in Patients with Meningococcal Disease," *Lancet*, 1 (8529): 355–357 (1987).

Wallach, et al., "Cell Surfae and Soluable TNF Receptors," Tumor Necrosis Factor: Structure–Function Relationship and Clinical Application, Osawa T. Bonavida B (eds.), Karger, Basel. 47–57 (1992).

Wallach, et al., "Mechanisms Which Take Part in Regulation of the Response to Tumor Necrosis Factor," *Lymphokine Research* 8 (3): 359–363 (1989).

Wallach, David, "Preparations of Lymphotoxin Induce Resistance to Their Own Cytotoxic Effect," *J. Immunol.* 132 (5): 2464–2469 (1984).

Wallach, et al., "Regulation of the Response to Tumor Necrosis Factor," *Tumor Necrosis Factor/Cachectin and Related Cytokines Int. Conf., Heidelberg 1987*, Tumor Necrosis Factor Related Cytotoxins, Bonavida, Gifford, Kirchner, Old (eds). Karger, Basel, pp. 134–147 (1988).

Walsh, et al., "Isolation and Purification of ILS, an Interleukin 1 Inhibitor Produced by Human Gingival Epithelial Cells," *Clin. Exp. Immunol.* 68: 366–374 (1987).

Weber, et al., "Production of an Epidermal Growth Factor Receptor–Related Protein," *Science* 224: 294–297 (1984).

Weisman, et al., "Soluble Human Complement Receptor Type I: In Vivo Inhibitor of Complement Suppressing Post–Ischemic Myocardial Inflammation and Necrosis," *Science*, 249: 146–151 (1990).

Yoshie, et al., "Binding and Crosslinking of 125I–Labeled Recombianant Human Tumor Necrosis Factor to Cell Surface Receptors," *J. Biochem.* 100: 531–541 (1986).

Zalipsky, Samuel, "Synthesis of an End–Group Functionalized Polyethylene Glycol–Lipid Conjugate for Preparation of Polymer–Grafted Liposomes," *Bioconjugate Chem.*, 4: 296–299 (1993).

Zeigler, Elizabeth, J., "Tumor Necrosis Factor in Humans," *New Engl. J. Med.* 318 (23): 1533–1535 (1988).

* cited by examiner

FIG. 1

```
5'-GATAGTGTGTGTCCCCAAGGAAAATATATCCACCCTCAAAATAATTCGATTTGCTGTACC-
    D  S  V  C  P  Q  G  K  Y  I  H  P  Q  N  N  S  I  C  C  T  -

-AAGTGCCACAAAGGAACCTACTTGTACAATGACTGTCCAGGCCCGGGGCAGGATACGGAC-
    K  C  H  K  G  T  Y  L  Y  N  D  C  P  G  P  G  Q  D  T  D  -

-TGCAGGGAGTGTGAGAGCGGCTCCTTCACCGCTTCAGAAAACCACCTCAGACACTGCCTC-
    C  R  E  C  E  S  G  S  F  T  A  S  E  N  H  L  R  H  C  L  -

-AGCTGCTCCAAATGCCGAAAGGAAATGGGTCAGGTGGAGATCTCTTCTTGCACAGTGGAC-
    S  C  S  K  C  R  K  E  M  G  Q  V  E  I  S  S  C  T  V  D  -

-CGGGACACCGTGTGTGGCTGCAGGAAGAACCAGTACCGGCATTATTGGAGTGAAAACCTT-
    R  D  T  V  C  G  C  R  K  N  Q  Y  R  H  Y  W  S  E  N  L  -

-TTCCACTGCTTCAATTGCAGCCTCTGCCTCAATGGGACCGTGCACCTCTCCTGCCAGGAG-
    F  Q  C  F  N  C  S  L  C  L  N  G  T  V  H  L  S  C  Q  E  -

-AAACAGAACACCGTGTGCACCTGCCATGCAGGTTTCTTTCTAAGAGAAAACGAGTGTGTC-
    K  Q  N  T  V  C  T  C  H  A  G  F  F  L  R  E  N  E  C  V  -

-TCCTGTAGTAACTGTAAGAAAAGCCTGGAGTGCACGAAGTTGTGCCTACCCCAGATTGAG-
    S  C  S  N  C  K  K  S  L  E  C  T  K  L  C  L  P  Q  I  E  -

-AAT-3'
    N  *
```

FIG.2

```
5'-CATATGGACAGCGTTTGCCCCCAAGGAAAATACATCCACCCTCAAAATAATTCGATTTGC-
    +---------+---------+---------+---------+---------+---------
     M  D  S  V  C  P  Q  G  K  Y  I  H  P  Q  N  N  S  I  C

-TGTACCAAGTGCCACAAAGGAACCTACTTGTACAATGACTGTCCAGGCCCGGGGCAGGAT-
    +---------+---------+---------+---------+---------+---------
    C  T  K  C  H  K  G  T  Y  L  Y  N  D  C  P  G  P  G  Q  D

-ACGGACTGCAGGGAGTGTGAGAGCGGCTCCTTCACCGCTTCAGAAAACCACCTCAGACAC-
    +---------+---------+---------+---------+---------+---------
    T  D  C  R  E  C  E  S  G  S  F  T  A  S  E  N  H  L  R  H

-TGCCTCAGCTGCTCCAAATGCCGAAAGGAAATGGGTCAGGTGGAGATCTCTTCTTGCACA-
    +---------+---------+---------+---------+---------+---------
    C  L  S  C  S  K  C  R  K  E  M  G  Q  V  E  I  S  S  C  T

-GTGGACCGGGACACCGTGTGTGGCTGCAGGAAGAACCAGTACCGGCATTATTGGAGTGAA-
    +---------+---------+---------+---------+---------+---------
    V  D  R  D  T  V  C  G  C  R  K  N  Q  Y  R  H  Y  W  S  E

-AACCTTTTCCAGTGCTTCTGCTGATAGGATCC-3'
    +---------+---------+---------+---------+---------+---------
    N  L  F  Q  C  F  C  *
```

FIG. 3

```
5'-CATATGGACA GCGTTTGCCCCCAAGGAAAATATATCCACCCTCAAAATAATTCGATTTGC-
    M  D  S  V  C  P  Q  G  K  Y  I  H  P  Q  N  N  S  I  C  -

-TGTACCAAGTGCCACAAAGGAACCTACTTGTACAATGACTGTCCAGGCCCGGGGCAGGAT-
  C  T  K  C  H  K  G  T  Y  L  Y  N  D  C  P  G  P  G  Q  D  -

-ACGGACTGCAGGGAGTGTGAGAGCGGCTCCTTCACCGCTTCAGAAAACCACCTCAGACAC-
  T  D  C  R  E  C  E  S  G  S  F  T  A  S  E  N  H  L  R  H  -

-TGCCTCAGCTGCTCCAAATGCCGAAAGGAAATGGGTCAGGTGGAGATCTCTTCTTGCACA-
  C  L  S  C  S  K  C  R  K  E  M  G  Q  V  E  I  S  S  C  T  -

-GTGGACCGGGACACCGTGTGTGGCTGCAGGAAGAACCAGTACCGGCATTATTGGAGTGAA-
  V  D  R  D  T  V  C  G  C  R  K  N  Q  Y  R  H  Y  W  S  E  -

-AACCTTTTCCAGTGCTTCAATTGCTCTCTGTAAAAGCTT-3'
  N  L  F  Q  C  F  N  C  S  L  *
```

FIG.4

```
5'-CATATGGACAGCGTTTGCCCCCAAGGAAAATATATCCACCCTCAAAATAATTCGATTTGC-
   +---------+---------+---------+---------+---------+---------
      M  D  S  V  C  P  Q  G  K  Y  I  H  P  Q  N  N  S  I  C  -

-TGTACCAAGTGCCACAAAGGAACCTACTTGTACAATGACTGTCCAGGCCCGGGGCAGGAT-
 +---------+---------+---------+---------+---------+---------
   C  T  K  C  H  K  G  T  Y  L  Y  N  D  C  P  G  P  G  Q  D  -

-ACGGACTGCAGGGAGTGTGAGAGCGGCTCCTTCACCGCTTCAGAAAACCACCTCAGACAC-
 +---------+---------+---------+---------+---------+---------
   T  D  C  R  E  C  E  S  G  S  F  T  A  S  E  N  H  L  R  H  -

-TGCCTCAGCTGCTCCAAATGCCGAAAGGAAATGGGTCAGGTGGAGATCTCTTCTTGCACA-
 +---------+---------+---------+---------+---------+---------
   C  L  S  C  S  K  C  R  K  E  M  G  Q  V  E  I  S  S  C  T  -

-GTGGACCGGGACACCGTGTGTGGTTGCAGGAAGAACCAGTACCGGCATTATTGGAGTGAA-
 +---------+---------+---------+---------+---------+---------
   V  D  R  D  T  V  C  G  C  R  K  N  Q  Y  R  H  Y  W  S  E  -

-AACCTTTTCCAGTGCTTCAATTAATAGGGATCC-3'
 +---------+---------+---------+---------+---------+---------
   N  L  F  Q  C  F  N  *
```

FIG.5

```
5'-CATATGTATATCCACCCTCAAAATAATTCGATTTGCTGTACCAAGTGCCACAAAGGAACC-
   +---------+---------+---------+---------+---------+---------
     M  Y  I  H  P  Q  N  N  S  I  C  C  T  K  C  H  K  G  T  -

-TACTTGTACAATGACTGTCCAGGCCCGGGGCAGGATACGGACTGCAGGGAGTGTGAGAGC-
 +---------+---------+---------+---------+---------+---------
  Y  L  Y  N  D  C  P  G  P  G  Q  D  T  D  C  R  E  C  E  S  -

-GGCTCCTTCACCGCTTCAGAAAACCACCTCAGACACTGCCTCAGCTGCTCCAAATGCCGA-
 +---------+---------+---------+---------+---------+---------
  G  S  F  T  A  S  E  N  H  L  R  H  C  L  S  C  S  K  C  R  -

-AAGGAAATGGGTCAGGTGGAGATCTCTTCTTGCACAGTGGACCGGGACACCGTGTGTGGC-
 +---------+---------+---------+---------+---------+---------
  K  E  M  G  Q  V  E  I  S  S  C  T  V  D  R  D  T  V  C  G  -

-TGCAGGAAGAACCAGTACCGGCATTATTGGAGTGAAAACCTTTTCCAGTGCTTCAATTGC-
 +---------+---------+---------+---------+---------+---------
  C  R  K  N  Q  Y  R  H  Y  W  S  E  N  L  F  Q  C  F  N  C  -

-TCTCTGTAAAAGCTT-3'
 +---------+---------+---------+---------+---------+---------
  S  L  *
```

FIG.6

```
5'-CATATGTGTACCAAGTGCCACAAAGGAACCTACTTGTACAATGACTGTCCAGGCCCGGGG-
    M  C  T  K  C  H  K  G  T  Y  L  Y  N  D  C  P  G  P  G

-CAGGATACGGACTGCAGGGAGTGTGAGAGCGGCTCCTTCACCGCTTCAGAAAACCACCTC
    Q  D  T  D  C  R  E  C  E  S  G  S  F  T  A  S  E  N  H  L

-AGACACTGCCTCAGCTGCTCCAAATGCCGAAAGGAAATGGGTCAGGTGGAGATCTCTTCT-
    R  H  C  L  S  C  S  K  C  R  K  E  M  G  Q  V  E  I  S  S

-TGCACAGTGGACCGGGACACCGTGTGTGGCTGCAGGAAGAACCAGTACCGGCATTATTGG-
    C  T  V  D  R  D  T  V  C  G  C  R  K  N  Q  Y  R  H  Y  W

-AGTGAAAACCTTTTCCAGTGCTTCAATTGCTCTCTGTAAAAGCTT-3'
    S  E  N  L  F  Q  C  F  N  C  S  L  *
```

FIG. 7

```
5'-CATATGTCGATTAGCTGTACCAAGTGCCACAAAGGAACCTACTTGTACAATGACTGTCCA-
   +---------+---------+---------+---------+---------+---------
      M  S  I  S  C  T  K  C  H  K  G  T  Y  L  Y  N  D  C  P  -

-GGCCCGGGGCAGGATACGGACTGCAGGGAGTGTGAGAGCGGCTCCTTCACCGCTTCAGAA-
  +---------+---------+---------+---------+---------+---------
    G  P  G  Q  D  T  D  C  R  E  C  E  S  G  S  F  T  A  S  E  -

-AACCACCTCAGACACTGCCTCAGCTGCTCCAAATGCCGAAAGGAAATGGGTCAGGTGGAG-
  +---------+---------+---------+---------+---------+---------
    N  H  L  R  H  C  L  S  C  S  K  C  R  K  E  M  G  Q  V  E  -

-ATCTCTTCTTGCACAGTGGACCGGGACACCGTCTGTGGCTGCAGGAAGAACCAGTACCGG-
  +---------+---------+---------+---------+---------+---------
    I  S  S  C  T  V  D  R  D  T  V  C  G  C  R  K  N  Q  Y  R  -

-CATTATTGGAGTGAAAACCTTTTCCAGTGCTTCAATTGCTCTCTGTAAAAGCTT-3'
  +---------+---------+---------+---------+---------+---------
    H  Y  W  S  E  N  L  F  Q  C  F  N  C  S  L  *
```

FIG. 8

```
5'-TTGCCCGCCCAGGTGGCATTTACACCCTACGCCCCGGAGCCCGGGAGCACATGCCGGCTC-
   +---------+---------+---------+---------+---------+---------
    L  P  A  Q  V  A  F  T  P  Y  A  P  E  P  G  S  T  C  R  L -

-AGAGAATACTATGACCAGACAGCTCAGATGTGCTGCAGCAAGTGCTCGCCGGGCCAACAT-
  +---------+---------+---------+---------+---------+---------
    R  E  Y  Y  D  Q  T  A  Q  M  C  C  S  K  C  S  P  G  Q  H -

-GCAAAAGTCTTCTGTACCAAGACCTCGGACACCGTGTGTGACTCCTGTGAGGACAGCACA-
  +---------+---------+---------+---------+---------+---------
    A  K  V  F  C  T  K  T  S  D  T  V  C  D  S  C  E  D  S  T -

-TACACCCAGCTCTGGAACTGGGTTCCCGAGTGCTTGAGCTGTGGCTCCCGCTGTAGCTCT-
  +---------+---------+---------+---------+---------+---------
    Y  T  Q  L  W  N  W  V  P  E  C  L  S  C  G  S  R  C  S  S -

-GACCAGGTGGAAACTCAAGCCTGCACTCGGGAACAGAACCGCATCTGCACCTGCAGGCCC-
  +---------+---------+---------+---------+---------+---------
    D  Q  V  E  T  Q  A  C  T  R  E  Q  N  R  I  C  T  C  R  P -

-GGCTGGTACTGCGCGCTGAGCAAGCAGGAGGGGTGCCGGCTGTGCGCGCCGCTGCGCAAG-
  +---------+---------+---------+---------+---------+---------
    G  W  Y  C  A  L  S  K  Q  E  G  C  R  L  C  A  P  L  R  K -

-TGCCGCCCGGGCTTCGGCGTGGCCAGACCAGGAACTGAAACATCAGACGTGGTGTGCAAG-
  +---------+---------+---------+---------+---------+---------
    C  R  P  G  F  G  V  A  R  P  G  T  E  T  S  D  V  V  C  K -

-CCCTGTGCCCCGGGGACGTTCTCCAACACGACTTCATCCACGGATATTTGCAGGCCCCAC-
  +---------+---------+---------+---------+---------+---------
    P  C  A  P  G  T  F  S  N  T  T  S  S  T  D  I  C  R  P  H -

-CAGATCTGTAACGTGGTGGCCATCCCTGGGAATGCAAGCAGGGATGCAGTCTGCACGTCC-
  +---------+---------+---------+---------+---------+---------
    Q  I  C  N  V  V  A  I  P  G  N  A  S  R  D  A  V  C  T  S -

-ACGTCCCCCACCCGGAGTATGGCCCCAGGGGCAGTACACTTACCCCAGCCAGTGTCCACA-
  +---------+---------+---------+---------+---------+---------
    T  S  P  T  R  S  M  A  P  G  A  V  H  L  P  Q  P  V  S  T -

-CGATCCCAACACACGCAGCCAACTCCAGAACCCAGCACTGCTCCAAGCACCTCCTTCCTG-
  +---------+---------+---------+---------+---------+---------
    R  S  Q  H  T  Q  P  T  P  E  P  S  T  A  P  S  T  S  F  L -

-CTCCCAATGGGCCCCAGCCCCCCAGCTGAAGGGAGCACTGGCGAC-3'
  +---------+---------+---------+---------+---------
    L  P  M  G  P  S  P  P  A  E  G  S  T  G  D  *
```

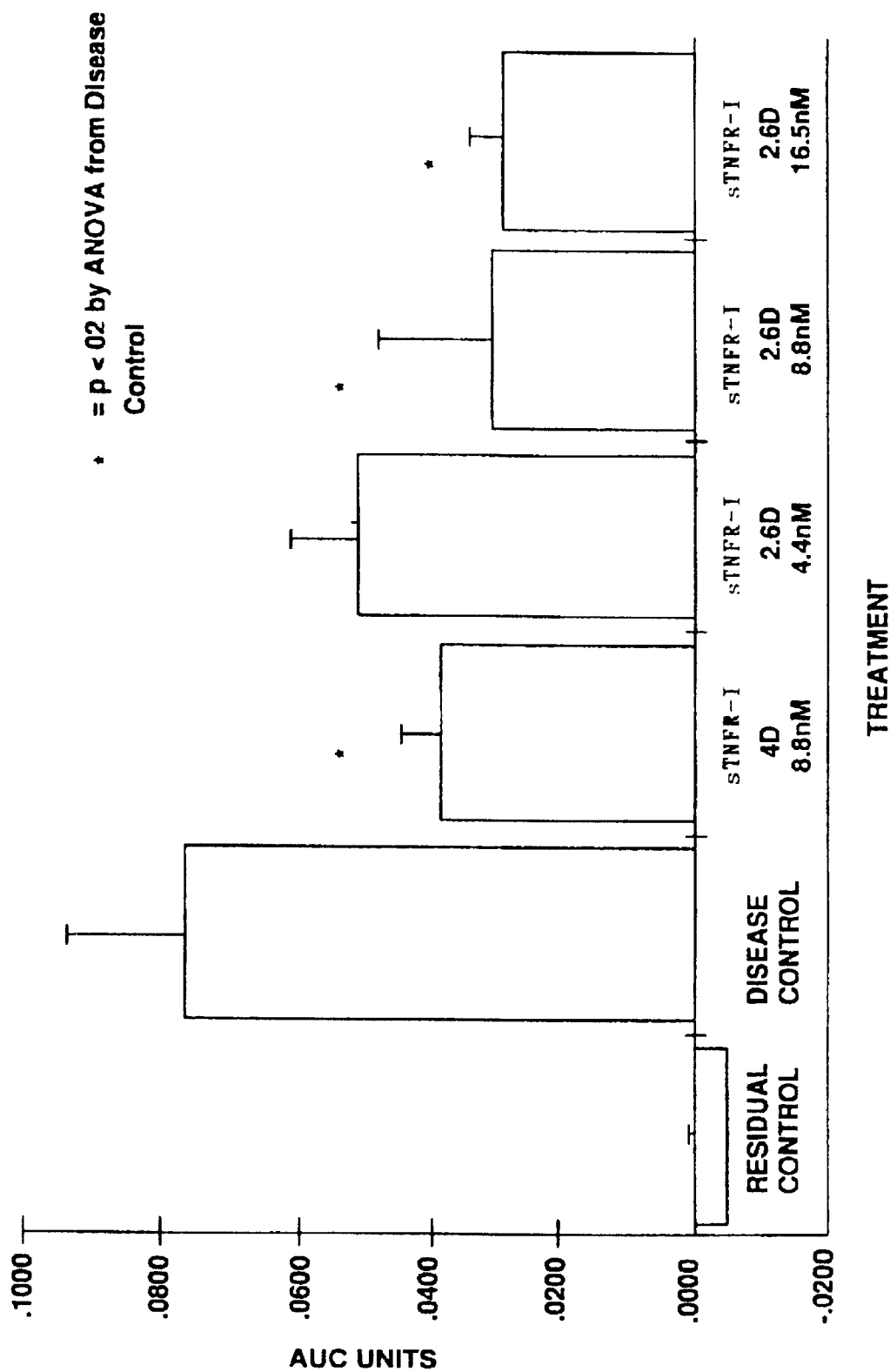

SEQUENCE LISTING

<160> NUMBER OF SEQ ID NOS: 30

<210> SEQ ID NO 1
<211> LENGTH: 483
<212> TYPE: DNA
<213> ORGANISM: Homo sapiens
<220> FEATURE:
<221> NAME/KEY: CDS
<222> LOCATION: (1)..(483)

<400> SEQUENCE: 1

```
gat agt gtg tgt ccc caa gga aaa tat atc cac cct caa aat aat tcg        48
Asp Ser Val Cys Pro Gln Gly Lys Tyr Ile His Pro Gln Asn Asn Ser
  1               5                  10                  15 att tgc tgt acc aag tgc cac aaa gga acc tac ttg tac aat gac tgt        96
Ile Cys Cys Thr Lys Cys His Lys Gly Thr Tyr Leu Tyr Asn Asp Cys
             20                  25                  30 cca ggc ccg ggg cag gat acg gac tgc agg gag tgt gag agc ggc tcc       144
Pro Gly Pro Gly Gln Asp Thr Asp Cys Arg Glu Cys Glu Ser Gly Ser
         35                  40                  45 ttc acc gct tca gaa aac cac ctc aga cac tgc ctc agc tgc tcc aaa       192
Phe Thr Ala Ser Glu Asn His Leu Arg His Cys Leu Ser Cys Ser Lys
 50                  55                  60 tgc cga aag gaa atg ggt cag gtg gag atc tct tct tgc aca gtg gac       240
Cys Arg Lys Glu Met Gly Gln Val Glu Ile Ser Ser Cys Thr Val Asp
 65                  70                  75                  80 cgg gac acc gtg tgt ggc tgc agg aag aac cag tac cgg cat tat tgg       288
Arg Asp Thr Val Cys Gly Cys Arg Lys Asn Gln Tyr Arg His Tyr Trp
                 85                  90                  95 agt gaa aac ctt ttc cag tgc ttc aat tgc agc ctc tgc ctc aat ggg       336
Ser Glu Asn Leu Phe Gln Cys Phe Asn Cys Ser Leu Cys Leu Asn Gly
            100                 105                 110 acc gtg cac ctc tcc tgc cag gag aaa cag aac acc gtg tgc acc tgc       384
Thr Val His Leu Ser Cys Gln Glu Lys Gln Asn Thr Val Cys Thr Cys
        115                 120                 125 cat gca ggt ttc ttt cta aga gaa aac gag tgt gtc tcc tgt agt aac       432
His Ala Gly Phe Phe Leu Arg Glu Asn Glu Cys Val Ser Cys Ser Asn
    130                 135                 140 tgt aag aaa agc ctg gag tgc acg aag ttg tgc cta ccc cag att gag       480
Cys Lys Lys Ser Leu Glu Cys Thr Lys Leu Cys Leu Pro Gln Ile Glu
145                 150                 155                 160 aat                                                                    483
Asn
```

<210> SEQ ID NO 2
<211> LENGTH: 161
<212> TYPE: PRT
<213> ORGANISM: Homo sapiens

<400> SEQUENCE: 2

```
Asp Ser Val Cys Pro Gln Gly Lys Tyr Ile His Pro Gln Asn Asn Ser
  1               5                  10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
         35                  40                  45

Phe Thr Ala Ser Glu Asn His Leu Arg His Cys Leu Ser Cys Ser Lys
 50                  55                  60

Cys Arg Lys Glu Met Gly Gln Val Glu Ile Ser Ser Cys Thr Val Asp
```

```
                65                  70                  75                  80
Arg Asp Thr Val Cys Gly Cys Arg Lys Asn Gln Tyr Arg His Tyr Trp
                            85                  90                  95

Ser Glu Asn Leu Phe Gln Cys Phe Asn Cys Ser Leu Cys Leu Asn Gly
                100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn

<210> SEQ ID NO 3
<211> LENGTH: 332
<212> TYPE: DNA
<213> ORGANISM: Artificial Sequence
<220> FEATURE:
<223> OTHER INFORMATION: Description of Artificial Sequence: sTNFR-I
      2.6D/C105
<220> FEATURE:
<221> NAME/KEY: CDS
<222> LOCATION: (4)..(321)

<400> SEQUENCE: 3 cat atg gac agc gtt tgc ccc caa gga aaa tac atc cac cct caa aat         48
    Met Asp Ser Val Cys Pro Gln Gly Lys Tyr Ile His Pro Gln Asn
    1               5                   10                  15 aat tcg att tgc tgt acc aag tgc cac aaa gga acc tac ttg tac aat         96
Asn Ser Ile Cys Cys Thr Lys Cys His Lys Gly Thr Tyr Leu Tyr Asn
                20                  25                  30 gac tgt cca ggc ccg ggg cag gat acg gac tgc agg gag tgt gag agc        144
Asp Cys Pro Gly Pro Gly Gln Asp Thr Asp Cys Arg Glu Cys Glu Ser
            35                  40                  45 ggc tcc ttc acc gct tca gaa aac cac ctc aga cac tgc ctc agc tgc        192
Gly Ser Phe Thr Ala Ser Glu Asn His Leu Arg His Cys Leu Ser Cys
        50                  55                  60 tcc aaa tgc cga aag gaa atg ggt cag gtg gag atc tct tct tgc aca        240
Ser Lys Cys Arg Lys Glu Met Gly Gln Val Glu Ile Ser Ser Cys Thr
    65                  70                  75 gtg gac cgg gac acc gtg tgt ggc tgc agg aag aac cag tac cgg cat        288
Val Asp Arg Asp Thr Val Cys Gly Cys Arg Lys Asn Gln Tyr Arg His
80                  85                  90                  95 tat tgg agt gaa aac ctt ttc cag tgc ttc tgc tgataggatc c               332
Tyr Trp Ser Glu Asn Leu Phe Gln Cys Phe Cys
                100                 105

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: sTNFR-I
      2.6D/C105

<400> SEQUENCE: 4

Met Asp Ser Val Cys Pro Gln Gly Lys Tyr Ile His Pro Gln Asn Asn
1               5                   10                  15

Ser Ile Cys Cys Thr Lys Cys His Lys Gly Thr Tyr Leu Tyr Asn Asp
            20                  25                  30

Cys Pro Gly Pro Gly Gln Asp Thr Asp Cys Arg Glu Cys Glu Ser Gly
```

```
                    35                  40                  45
Ser Phe Thr Ala Ser Glu Asn His Leu Arg His Cys Leu Ser Cys Ser
        50                  55                  60

Lys Cys Arg Lys Glu Met Gly Gln Val Glu Ile Ser Ser Cys Thr Val
 65                  70                  75                  80

Asp Arg Asp Thr Val Cys Gly Cys Arg Lys Asn Gln Tyr Arg His Tyr
                85                  90                  95

Trp Ser Glu Asn Leu Phe Gln Cys Phe Cys
            100                 105

<210> SEQ ID NO 5
<211> LENGTH: 339
<212> TYPE: DNA
<213> ORGANISM: Artificial Sequence
<220> FEATURE:
<223> OTHER INFORMATION: Description of Artificial Sequence: sTNFR-I
      2.6D/C106
<220> FEATURE:
<221> NAME/KEY: CDS
<222> LOCATION: (4)..(330)

<400> SEQUENCE: 5 cat atg gac agc gtt tgc ccc caa gga aaa tat atc cac cct caa aat      48
    Met Asp Ser Val Cys Pro Gln Gly Lys Tyr Ile His Pro Gln Asn
     1               5                  10                  15 aat tcg att tgc tgt acc aag tgc cac aaa gga acc tac ttg tac aat      96
Asn Ser Ile Cys Cys Thr Lys Cys His Lys Gly Thr Tyr Leu Tyr Asn
                20                  25                  30 gac tgt cca ggc ccg ggg cag gat acg gac tgc agg gag tgt gag agc     144
Asp Cys Pro Gly Pro Gly Gln Asp Thr Asp Cys Arg Glu Cys Glu Ser
             35                  40                  45 ggc tcc ttc acc gct tca gaa aac cac ctc aga cac tgc ctc agc tgc     192
Gly Ser Phe Thr Ala Ser Glu Asn His Leu Arg His Cys Leu Ser Cys
         50                  55                  60 tcc aaa tgc cga aag gaa atg ggt cag gtg gag atc tct tct tgc aca     240
Ser Lys Cys Arg Lys Glu Met Gly Gln Val Glu Ile Ser Ser Cys Thr
 65                  70                  75 gtg gac cgg gac acc gtg tgt ggc tgc agg aag aac cag tac cgg cat     288
Val Asp Arg Asp Thr Val Cys Gly Cys Arg Lys Asn Gln Tyr Arg His
 80                  85                  90                  95 tat tgg agt gaa aac ctt ttc cag tgc ttc aat tgc tct ctg taaaagctt   339
Tyr Trp Ser Glu Asn Leu Phe Gln Cys Phe Asn Cys Ser Leu
                100                 105

<210> SEQ ID NO 6
<211> LENGTH: 109
<212> TYPE: PRT
<213> ORGANISM: Artificial Sequence
<220> FEATURE:
<223> OTHER INFORMATION: Description of Artificial Sequence: sTNFR-I
      2.6D/C106

<400> SEQUENCE: 6

Met Asp Ser Val Cys Pro Gln Gly Lys Tyr Ile His Pro Gln Asn Asn
 1               5                  10                  15

Ser Ile Cys Cys Thr Lys Cys His Lys Gly Thr Tyr Leu Tyr Asn Asp
                20                  25                  30

Cys Pro Gly Pro Gly Gln Asp Thr Asp Cys Arg Glu Cys Glu Ser Gly
             35                  40                  45

Ser Phe Thr Ala Ser Glu Asn His Leu Arg His Cys Leu Ser Cys Ser
         50                  55                  60
```

```
Lys Cys Arg Lys Glu Met Gly Gln Val Glu Ile Ser Ser Cys Thr Val
 65                  70                  75                  80

Asp Arg Asp Thr Val Cys Gly Cys Arg Lys Asn Gln Tyr Arg His Tyr
                 85                  90                  95

Trp Ser Glu Asn Leu Phe Gln Cys Phe Asn Cys Ser Leu
            100                 105

<210> SEQ ID NO 7
<211> LENGTH: 333
<212> TYPE: DNA
<213> ORGANISM: Artificial Sequence
<220> FEATURE:
<223> OTHER INFORMATION: Description of Artificial Sequence: sTNFR-I
      2.6D/N105
<220> FEATURE:
<221> NAME/KEY: CDS
<222> LOCATION: (4)..(321)

<400> SEQUENCE: 7 cat atg gac agc gtt tgc ccc caa gga aaa tat atc cac cct caa aat      48
    Met Asp Ser Val Cys Pro Gln Gly Lys Tyr Ile His Pro Gln Asn
    1               5                  10                  15 aat tcg att tgc tgt acc aag tgc cac aaa gga acc tac ttg tac aat      96
Asn Ser Ile Cys Cys Thr Lys Cys His Lys Gly Thr Tyr Leu Tyr Asn
             20                  25                  30 gac tgt cca ggc ccg ggg cag gat acg gac tgc agg gag tgt gag agc     144
Asp Cys Pro Gly Pro Gly Gln Asp Thr Asp Cys Arg Glu Cys Glu Ser
         35                  40                  45 ggc tcc ttc acc gct tca gaa aac cac ctc aga cac tgc ctc agc tgc     192
Gly Ser Phe Thr Ala Ser Glu Asn His Leu Arg His Cys Leu Ser Cys
     50                  55                  60 tcc aaa tgc cga aag gaa atg ggt cag gtg gag atc tct tct tgc aca     240
Ser Lys Cys Arg Lys Glu Met Gly Gln Val Glu Ile Ser Ser Cys Thr
 65                  70                  75 gtg gac cgg gac acc gtg tgt ggt tgc agg aag aac cag tac cgg cat     288
Val Asp Arg Asp Thr Val Cys Gly Cys Arg Lys Asn Gln Tyr Arg His
 80                  85                  90                  95 tat tgg agt gaa aac ctt ttc cag tgc ttc aat taataggga tcc           333
Tyr Trp Ser Glu Asn Leu Phe Gln Cys Phe Asn
                100                 105

<210> SEQ ID NO 8
<211> LENGTH: 106
<212> TYPE: PRT
<213> ORGANISM: Artificial Sequence
<220> FEATURE:
<223> OTHER INFORMATION: Description of Artificial Sequence: sTNFR-I
      2.6D/N105

<400> SEQUENCE: 8

Met Asp Ser Val Cys Pro Gln Gly Lys Tyr Ile His Pro Gln Asn Asn
1               5                  10                  15

Ser Ile Cys Cys Thr Lys Cys His Lys Gly Thr Tyr Leu Tyr Asn Asp
             20                  25                  30

Cys Pro Gly Pro Gly Gln Asp Thr Asp Cys Arg Glu Cys Glu Ser Gly
         35                  40                  45

Ser Phe Thr Ala Ser Glu Asn His Leu Arg His Cys Leu Ser Cys Ser
     50                  55                  60

Lys Cys Arg Lys Glu Met Gly Gln Val Glu Ile Ser Ser Cys Thr Val
 65                  70                  75                  80

Asp Arg Asp Thr Val Cys Gly Cys Arg Lys Asn Gln Tyr Arg His Tyr
                 85                  90                  95
```

<210> SEQ ID NO 9
<211> LENGTH: 285
<212> TYPE: DNA
<213> ORGANISM: Artificial Sequence
<220> FEATURE:
<223> OTHER INFORMATION: Description of Artificial Sequence: sTNFR-I
      2.3D/d18
<220> FEATURE:
<221> NAME/KEY: CDS
<222> LOCATION: (4)..(276)

<400> SEQUENCE: 9

```
cat atg tgt acc aag tgc cac aaa gga acc tac ttg tac aat gac tgt      48
    Met Cys Thr Lys Cys His Lys Gly Thr Tyr Leu Tyr Asn Asp Cys
    1               5                  10                  15 cca ggc ccg ggg cag gat acg gac tgc agg gag tgt gag agc ggc tcc      96
Pro Gly Pro Gly Gln Asp Thr Asp Cys Arg Glu Cys Glu Ser Gly Ser
                20                  25                  30 ttc acc gct tca gaa aac cac ctc aga cac tgc ctc agc tgc tcc aaa     144
Phe Thr Ala Ser Glu Asn His Leu Arg His Cys Leu Ser Cys Ser Lys
            35                  40                  45 tgc cga aag gaa atg ggt cag gtg gag atc tct tct tgc aca gtg gac     192
Cys Arg Lys Glu Met Gly Gln Val Glu Ile Ser Ser Cys Thr Val Asp
        50                  55                  60 cgg gac acc gtg tgt ggc tgc agg aag aac cag tac cgg cat tat tgg     240
Arg Asp Thr Val Cys Gly Cys Arg Lys Asn Gln Tyr Arg His Tyr Trp
    65                  70                  75 agt gaa aac ctt ttc cag tgc ttc aat tgc tct ctg taaaagctt           285
Ser Glu Asn Leu Phe Gln Cys Phe Asn Cys Ser Leu
80                  85                  90
```

<210> SEQ ID NO 10
<211> LENGTH: 91
<212> TYPE: PRT
<213> ORGANISM: Artificial Sequence
<220> FEATURE:
<223> OTHER INFORMATION: Description of Artificial Sequence: sTNFR-I
      2.3D/d18

<400> SEQUENCE: 10

```
Met Cys Thr Lys Cys His Lys Gly Thr Tyr Leu Tyr Asn Asp Cys Pro
1               5                  10                  15

Gly Pro Gly Gln Asp Thr Asp Cys Arg Glu Cys Glu Ser Gly Ser Phe
            20                  25                  30

Thr Ala Ser Glu Asn His Leu Arg His Cys Leu Ser Cys Ser Lys Cys
        35                  40                  45

Arg Lys Glu Met Gly Gln Val Glu Ile Ser Ser Cys Thr Val Asp Arg
    50                  55                  60

Asp Thr Val Cys Gly Cys Arg Lys Asn Gln Tyr Arg His Tyr Trp Ser
65                  70                  75                  80

Glu Asn Leu Phe Gln Cys Phe Asn Cys Ser Leu
                85                  90
```

<210> SEQ ID NO 11
<211> LENGTH: 315
<212> TYPE: DNA
<213> ORGANISM: Artificial Sequence
<220> FEATURE:
<223> OTHER INFORMATION: Description of Artificial Sequence: sTNFR-I
      2.3D/d8

<220> FEATURE:
<221> NAME/KEY: CDS
<222> LOCATION: (4)..(306)

<400> SEQUENCE: 11

| cat | atg<br>Met<br>1 | tat<br>Tyr | atc<br>Ile | cac<br>His | cct<br>Pro<br>5 | caa<br>Gln | aat<br>Asn | aat<br>Asn | tcg<br>Ser | att<br>Ile<br>10 | tgc<br>Cys | tgt<br>Cys | acc<br>Thr | aag<br>Lys | tgc<br>Cys<br>15 | 48 |
|---|---|---|---|---|---|---|---|---|---|---|---|---|---|---|---|---|
| cac<br>His | aaa<br>Lys | gga<br>Gly | acc<br>Thr | tac<br>Tyr<br>20 | ttg<br>Leu | tac<br>Tyr | aat<br>Asn | gac<br>Asp | tgt<br>Cys<br>25 | cca<br>Pro | ggc<br>Gly | ccg<br>Pro | ggg<br>Gly | cag<br>Gln<br>30 | gat<br>Asp | 96 |
| acg<br>Thr | gac<br>Asp | tgc<br>Cys | agg<br>Arg<br>35 | gag<br>Glu | tgt<br>Cys | gag<br>Glu | agc<br>Ser | ggc<br>Gly<br>40 | tcc<br>Ser | ttc<br>Phe | acc<br>Thr | gct<br>Ala | tca<br>Ser<br>45 | gaa<br>Glu | aac<br>Asn | 144 |
| cac<br>His | ctc<br>Leu | aga<br>Arg<br>50 | cac<br>His | tgc<br>Cys | ctc<br>Leu | agc<br>Ser | tgc<br>Cys<br>55 | tcc<br>Ser | aaa<br>Lys | tgc<br>Cys | cga<br>Arg | aag<br>Lys<br>60 | gaa<br>Glu | atg<br>Met | ggt<br>Gly | 192 |
| cag<br>Gln | gtg<br>Val<br>65 | gag<br>Glu | atc<br>Ile | tct<br>Ser | tct<br>Ser<br>70 | tgc<br>Cys | aca<br>Thr | gtg<br>Val | gac<br>Asp | cgg<br>Arg<br>75 | gac<br>Asp | acc<br>Thr | gtg<br>Val | tgt<br>Cys | ggc<br>Gly | 240 |
| tgc<br>Cys<br>80 | agg<br>Arg | aag<br>Lys | aac<br>Asn | cag<br>Gln | tac<br>Tyr<br>85 | cgg<br>Arg | cat<br>His | tat<br>Tyr | tgg<br>Trp | agt<br>Ser<br>90 | gaa<br>Glu | aac<br>Asn | ctt<br>Leu | ttc<br>Phe | cag<br>Gln<br>95 | 288 |
| tgc<br>Cys | ttc<br>Phe | aat<br>Asn | tgc<br>Cys | tct<br>Ser | ctg<br>Leu<br>100 | taaaagctt | | | | | | | | | | 315 |

<210> SEQ ID NO 12
<211> LENGTH: 101
<212> TYPE: PRT
<213> ORGANISM: Artificial Sequence
<220> FEATURE:
<223> OTHER INFORMATION: Description of Artificial Sequence: sTNFR-I
      2.3D/d8

<400> SEQUENCE: 12

Met Tyr Ile His Pro Gln Asn Asn Ser Ile Cys Cys Thr Lys Cys His
 1               5                  10                  15

Lys Gly Thr Tyr Leu Tyr Asn Asp Cys Pro Gly Pro Gly Gln Asp Thr
            20                  25                  30

Asp Cys Arg Glu Cys Glu Ser Gly Ser Phe Thr Ala Ser Glu Asn His
        35                  40                  45

Leu Arg His Cys Leu Ser Cys Ser Lys Cys Arg Lys Glu Met Gly Gln
    50                  55                  60

Val Glu Ile Ser Ser Cys Thr Val Asp Arg Asp Thr Val Cys Gly Cys
65                  70                  75                  80

Arg Lys Asn Gln Tyr Arg His Tyr Trp Ser Glu Asn Leu Phe Gln Cys
                85                  90                  95

Phe Asn Cys Ser Leu
            100

<210> SEQ ID NO 13
<211> LENGTH: 294
<212> TYPE: DNA
<213> ORGANISM: Artificial Sequence
<220> FEATURE:
<223> OTHER INFORMATION: Description of Artificial Sequence: sTNFR-I
      2.3D/d15
<220> FEATURE:
<221> NAME/KEY: CDS
<222> LOCATION: (4)..(285)

<400> SEQUENCE: 13

```
cat atg tcg att agc tgt acc aag tgc cac aaa gga acc tac ttg tac      48
    Met Ser Ile Ser Cys Thr Lys Cys His Lys Gly Thr Tyr Leu Tyr
    1               5                  10                  15 aat gac tgt cca ggc ccg ggg cag gat acg gac tgc agg gag tgt gag      96
Asn Asp Cys Pro Gly Pro Gly Gln Asp Thr Asp Cys Arg Glu Cys Glu
                20                  25                  30 agc ggc tcc ttc acc gct tca gaa aac cac ctc aga cac tgc ctc agc     144
Ser Gly Ser Phe Thr Ala Ser Glu Asn His Leu Arg His Cys Leu Ser
            35                  40                  45 tgc tcc aaa tgc cga aag gaa atg ggt cag gtg gag atc tct tct tgc     192
Cys Ser Lys Cys Arg Lys Glu Met Gly Gln Val Glu Ile Ser Ser Cys
        50                  55                  60 aca gtg gac cgg gac acc gtg tgt ggc tgc agg aag aac cag tac cgg     240
Thr Val Asp Arg Asp Thr Val Cys Gly Cys Arg Lys Asn Gln Tyr Arg
    65                  70                  75 cat tat tgg agt gaa aac ctt ttc cag tgc ttc aat tgc tct ctg         285
His Tyr Trp Ser Glu Asn Leu Phe Gln Cys Phe Asn Cys Ser Leu
80                  85                  90 taaaagctt                                                           294

<210> SEQ ID NO 14
<211> LENGTH: 94
<212> TYPE: PRT
<213> ORGANISM: Artificial Sequence
<220> FEATURE:
<223> OTHER INFORMATION: Description of Artificial Sequence: sTNFR-I
      2.3D/d15

<400> SEQUENCE: 14

Met Ser Ile Ser Cys Thr Lys Cys His Lys Gly Thr Tyr Leu Tyr Asn
1               5                   10                  15

Asp Cys Pro Gly Pro Gly Gln Asp Thr Asp Cys Arg Glu Cys Glu Ser
            20                  25                  30

Gly Ser Phe Thr Ala Ser Glu Asn His Leu Arg His Cys Leu Ser Cys
        35                  40                  45

Ser Lys Cys Arg Lys Glu Met Gly Gln Val Glu Ile Ser Ser Cys Thr
    50                  55                  60

Val Asp Arg Asp Thr Val Cys Gly Cys Arg Lys Asn Gln Tyr Arg His
65                  70                  75                  80

Tyr Trp Ser Glu Asn Leu Phe Gln Cys Phe Asn Cys Ser Leu
                85                  90

<210> SEQ ID NO 15
<211> LENGTH: 705
<212> TYPE: DNA
<213> ORGANISM: Homo sapiens
<220> FEATURE:
<221> NAME/KEY: CDS
<222> LOCATION: (1)..(705)

<400> SEQUENCE: 15 ttg ccc gcc cag gtg gca ttt aca ccc tac gcc ccg gag ccc ggg agc      48
Leu Pro Ala Gln Val Ala Phe Thr Pro Tyr Ala Pro Glu Pro Gly Ser
1               5                   10                  15 aca tgc cgg ctc aga gaa tac tat gac cag aca gct cag atg tgc tgc      96
Thr Cys Arg Leu Arg Glu Tyr Tyr Asp Gln Thr Ala Gln Met Cys Cys
            20                  25                  30 agc aag tgc tcg ccg ggc caa cat gca aaa gtc ttc tgt acc aag acc     144
Ser Lys Cys Ser Pro Gly Gln His Ala Lys Val Phe Cys Thr Lys Thr
        35                  40                  45
```

| | | |
|---|---|---|
| tcg gac acc gtg tgt gac tcc tgt gag gac agc aca tac acc cag ctc<br>Ser Asp Thr Val Cys Asp Ser Cys Glu Asp Ser Thr Tyr Thr Gln Leu<br>    50                    55                  60 | | 192 |
| tgg aac tgg gtt ccc gag tgc ttg agc tgt ggc tcc cgc tgt agc tct<br>Trp Asn Trp Val Pro Glu Cys Leu Ser Cys Gly Ser Arg Cys Ser Ser<br> 65                   70                   75                80 | | 240 |
| gac cag gtg gaa act caa gcc tgc act cgg gaa cag aac cgc atc tgc<br>Asp Gln Val Glu Thr Gln Ala Cys Thr Arg Glu Gln Asn Arg Ile Cys<br>                        85                  90                95 | | 288 |
| acc tgc agg ccc ggc tgg tac tgc gcg ctg agc aag cag gag ggg tgc<br>Thr Cys Arg Pro Gly Trp Tyr Cys Ala Leu Ser Lys Gln Glu Gly Cys<br>              100                 105              110 | | 336 |
| cgg ctg tgc gcg ccg ctg cgc aag tgc cgc ccg ggc ttc ggc gtg gcc<br>Arg Leu Cys Ala Pro Leu Arg Lys Cys Arg Pro Gly Phe Gly Val Ala<br>        115                   120                125 | | 384 |
| aga cca gga act gaa aca tca gac gtg gtg tgc aag ccc tgt gcc ccg<br>Arg Pro Gly Thr Glu Thr Ser Asp Val Val Cys Lys Pro Cys Ala Pro<br>130                 135                140 | | 432 |
| ggg acg ttc tcc aac acg act tca tcc acg gat att tgc agg ccc cac<br>Gly Thr Phe Ser Asn Thr Thr Ser Ser Thr Asp Ile Cys Arg Pro His<br>145                 150                155              160 | | 480 |
| cag atc tgt aac gtg gtg gcc atc cct ggg aat gca agc agg gat gca<br>Gln Ile Cys Asn Val Val Ala Ile Pro Gly Asn Ala Ser Arg Asp Ala<br>                     165                170              175 | | 528 |
| gtc tgc acg tcc acg tcc ccc acc cgg agt atg gcc cca ggg gca gta<br>Val Cys Thr Ser Thr Ser Pro Thr Arg Ser Met Ala Pro Gly Ala Val<br>        180                   185                190 | | 576 |
| cac tta ccc cag cca gtg tcc aca cga tcc caa cac acg cag cca act<br>His Leu Pro Gln Pro Val Ser Thr Arg Ser Gln His Thr Gln Pro Thr<br>               195                200              205 | | 624 |
| cca gaa ccc agc act gct cca agc acc tcc ttc ctg ctc cca atg ggc<br>Pro Glu Pro Ser Thr Ala Pro Ser Thr Ser Phe Leu Leu Pro Met Gly<br>210                 215                220 | | 672 |
| ccc agc ccc cca gct gaa ggg agc act ggc gac<br>Pro Ser Pro Pro Ala Glu Gly Ser Thr Gly Asp<br>225               230                235 | | 705 |

<210> SEQ ID NO 16
<211> LENGTH: 235
<212> TYPE: PRT
<213> ORGANISM: Homo sapiens

<400> SEQUENCE: 16

Leu Pro Ala Gln Val Ala Phe Thr Pro Tyr Ala Pro Glu Pro Gly Ser
 1               5                  10                  15

Thr Cys Arg Leu Arg Glu Tyr Tyr Asp Gln Thr Ala Gln Met Cys Cys
                20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
        50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

```
Arg Pro Gly Thr Glu Thr Ser Asp Val Val Cys Lys Pro Cys Ala Pro
    130                 135                 140
Gly Thr Phe Ser Asn Thr Thr Ser Ser Thr Asp Ile Cys Arg Pro His
145                 150                 155                 160
Gln Ile Cys Asn Val Val Ala Ile Pro Gly Asn Ala Ser Arg Asp Ala
                165                 170                 175
Val Cys Thr Ser Thr Ser Pro Thr Arg Ser Met Ala Pro Gly Ala Val
            180                 185                 190
His Leu Pro Gln Pro Val Ser Thr Arg Ser Gln His Thr Gln Pro Thr
        195                 200                 205
Pro Glu Pro Ser Thr Ala Pro Ser Thr Ser Phe Leu Leu Pro Met Gly
    210                 215                 220
Pro Ser Pro Pro Ala Glu Gly Ser Thr Gly Asp
225                 230                 235
```

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: PCR primer;
      Oligo#1

<400> SEQUENCE: 17
ggttagccat atggacagcg tttgccccca a                               31

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: PCR primer;
      Oligo#2

<400> SEQUENCE: 18
cccaagcttt tacagagagc aattgaagca ctg                             33

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: PCR primer;
      Oligo#3

<400> SEQUENCE: 19
actcgaggat ccgcggataa ataagtaacg atccggtcca                      40

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: PCR primer;
      Oligo#4

<400> SEQUENCE: 20
caggtcggat cctatcagca gaagcactgg aaaaggtttt c                    41

<210> SEQ ID NO 21
<211> LENGTH: 31
<212> TYPE: DNA
<213> ORGANISM: Artificial Sequence

```
<220> FEATURE:
<223> OTHER INFORMATION: Description of Artificial Sequence: PCR primer;
      Oligo#5

<400> SEQUENCE: 21
ggttagccat atggacagcg tttgccccca a                                    31

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: PCR primer;
      Oligo#6

<400> SEQUENCE: 22
cgcggatccc tattaattga agcactggaa aagg                                 34

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: PCR primer;
      Oligo#7

<400> SEQUENCE: 23
ccccatatgt atatccaccc tcaaaataat                                      30

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: PCR primer;
      Oligo#8

<400> SEQUENCE: 24
cccaagcttt tacagagagc aattgaagca ctg                                  33

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: PCR primer;
      Oligo#9

<400> SEQUENCE: 25
ccccatatgt cgattagctg taccaagtgc cacaaagg                             38

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: PCR primer;
      Oligo#10

<400> SEQUENCE: 26
cccaagcttt tacagagagc aattgaagca ctg                                  33

<210> SEQ ID NO 27
<211> LENGTH: 30
<212> TYPE: DNA
<213> ORGANISM: Artificial Sequence
<220> FEATURE:
```

-continued

```
<223> OTHER INFORMATION: Description of Artificial Sequence: PCR primer;
      Oligo#11

<400> SEQUENCE: 27
ccccatatgt gtaccaagtg ccacaaagga                                      30

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: PCR primer;
      Oligo#12

<400> SEQUENCE: 28
cccaagcttt tacagagagc aattgaagca ctg                                  33

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: PCR primer;
      Oligo#13

<400> SEQUENCE: 29
ggttagccat atggacagcg tttgccccca a                                    31

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: PCR primer;
      Oligo#14

<400> SEQUENCE: 30
cccaagcttt taggtgcaca cggtgttctg ttt                                  33
```

TRUNCATED SOLUBLE TUMOR NECROSIS FACTOR TYPE-I AND TYPE-II RECEPTORS

This application is a continuation of U.S. application Ser. No. 09/214,613, filed Jul. 9, 1999, now abandoned; which claims the benefit of priority of International Application No. PCT/US97/12244, filed Jul. 9, 1997, which was published under PCT Article 21(2) in English; which claims the benefit of priority of U.S. Provisional Application Nos. 60/039,792, filed Mar. 4, 1997; 60/039,314, filed Feb. 7, 1997; 60/037,737, filed Jan. 23, 1997; 60/032,534, filed Dec. 6, 1996; and 60/021,443, filed Jul. 9, 1996; the disclosure of each of which is explicitly incorporated by reference herein.

FIELD OF THE INVENTION

The present invention relates to the field of inflammation. More specifically, the present invention relates to truncated tumor necrosis factor receptors (sTNFRs).

BACKGROUND OF THE INVENTION

Inflammation is the body's defense reaction to injuries such as those caused by mechanical damage, infection or antigenic stimulation. An inflammatory reaction may be expressed pathologically when inflammation is induced by an inappropriate stimulus such as an autoantigen, is expressed in an exaggerated manner or persists well after the removal of the injurious agents. Such inflammatory reaction may include the production of certain cytokines.

While the etiology of inflammation is poorly understood, considerable information has recently been gained regarding the molecular aspects of inflammation. This research has led to identification of certain cytokines which are believed to figure prominently in the mediation of inflammation. Cytokines are extracellular proteins that modify the behavior of cells, particularly those cells that are in the immediate area of cytokine synthesis and release. Tumor necrosis factors (TNFs) are a class of cytokines produced by numerous cell types, including monocytes and macrophages.

At least two TNFs have been previously described, specifically TNF alpha (TNF-α) and TNF beta (TNF-β or lymphotoxin), and each is active as a trimeric molecule and is believed to initiate cellular signaling by crosslinking receptors (Engelmann et al. (1990), *J. Biol. Chem.*, 265:14497–14504).

Several lines of evidence implicate TNF-α and TNF-β as major inflammatory cytokines. These known TNFs have important physiological effects on a number of different target cells which are involved in inflammatory responses to a variety of stimuli such as infection and injury. The proteins cause both fibroblasts and synovial cells to secrete latent collagenase and prostaglandin $E_2$ and cause osteocyte cells to stimulate bone resorption. These proteins increase the surface adhesive properties of endothelial cells for neutrophils. They also cause endothelial cells to secrete coagulant activity and reduce their ability to lyse clots. In addition they redirect the activity of adipocytes away from the storage of lipids by inhibiting expression of the enzyme lipoprotein lipase. TNFs also cause hepatocytes to synthesize a class of proteins known as "acute phase reactants," which act on the hypothalamus as pyrogens (Selby et al. (1988), *Lancet*, 1(8583):483; Starnes, Jr. et al. (1988), *J. Clin. Invest.*, 82:1321; Oliff et al. (1987), *Cell*, 50:555; and Waage et al. (1987), *Lancet*, 1(8529):355). Additionally, preclinical results with various predictive animal models of inflammation, including rheumatoid arthritis, have suggested that inhibition of TNF can have a major impact on disease progression and severity (Dayer et al. (1994), *European Cytokine Network*, 5(6):563–571 and Feldmann et al. (1995), *Annals Of The New York Academy Of Sciences*, 66:272–278). Moreover, recent preliminary human clinical trials in rheumatoid arthritis with inhibitors of TNF have shown promising results (Rankin et al. (1995), *British Journal Of Rheumatology*, 3(4):4334–4342; Elliott et al. (1995), *Lancet*, 344:1105–1110; Tak et al. (1996), *Arthritis and Rheumatism*, 39:1077–1081; and Paleolog et al. (1996), *Arthritis and Rheumatism*, 39:1082–1091).

Protein inhibitors of TNF are disclosed in the art. EP 308 378 reports that a protein derived from the urine of fever patients has a TNF inhibiting activity. The effect of this protein is presumably due to a competitive mechanism at the level of the receptors. EP 308 378 discloses a protein sufficiently pure to be characterized by its N-terminus. The reference, however, does not teach any DNA sequence or a recombinantly-produced TNF inhibitor.

Recombinantly-produced TNF inhibitors have also been taught in the art. For example, EP 393 438 and EP 422 339 teach the amino acid and nucleic acid sequences of a mature, recombinant human "30 kDa TNF inhibitor" (also known as a p55 receptor and as sTNFR-I) and a mature, recombinant human "40 kDa inhibitor" (also known as a p75 receptor and as sTNFR-II) as well as modified forms thereof, e.g., fragments, functional derivatives and variants. EP 393 438 and EP 422 339 also disclose methods for isolating the genes responsible for coding the inhibitors, cloning the gene in suitable vectors and cell types, and expressing the gene to produce the inhibitors. Mature recombinant human 30 kDa TNF inhibitor and mature recombinant human 40 kDa TNF inhibitor have been demonstrated to be capable of inhibiting TNF (EP 393 438, EP 422 339, PCT Publication No. WO 92/16221 and PCT Publication No. WO 95/34326).

sTNFR-I and sTNFR-II are members of the nerve growth factor/TNF receptor superfamily of receptors which includes the nerve growth factor receptor (NGF), the B cell antigen CD40, 4-1BB, the rat T-cell antigen MRC OX40, the Fas antigen, and the CD27 and CD30 antigens (Smith et al. (1990), *Science*, 248:1019–1023). The most conserved feature amongst this group of cell surface receptors is the cysteine-rich extracellular ligand binding domain, which can be divided into four repeating motifs of about forty amino acids and which contains 4–6 cysteine residues at positions which are well conserved (Smith et al. (1990), supra).

EP 393 438 further teaches a 40 kDa TNF inhibitor Δ51 and a 40 kDa TNF inhibitor Δ53, which are truncated versions of the full-length recombinant 40 kDa TNF inhibitor protein wherein 51 or 53 amino acid residues, respectively, at the carboxyl terminus of the mature protein are removed. Accordingly, a skilled artisan would appreciate that the fourth domain of each of the 30 kDa TNF inhibitor and the 40 kDa inhibitor is not necessary for TNF inhibition. In fact various groups have confirmed this understanding. Domain-deletion derivatives of the 30 kDa and 40 kDa TNF inhibitors have been generated, and those derivatives without the fourth domain retain full TNF binding activity while those derivatives without the first, second or third domain, respectively, do not retain TNF binding activity (Corcoran et al. (1994), *Eur. J. Biochem.*, 223:831–840; Chih-Hsueh et al. (1995), *The Journal of Biological Chemistry*, 270(6): 2874–2878; and Scallon et al. (1995), *Cytokine*, 7(8): 759–770).

Due to the relatively low inhibition of cytotoxicity exhibited by the 30 kDa TNF inhibitor and 40 kDa TNF inhibitor (Butler et al. (1994), *Cytokine*, 6(6):616–623), various groups have generated dimers of TNF inhibitor proteins (Butler et al. (1994), supra; and Martin et al. (1995), *Exp. Neurol.*, 131:221–228). However, the dimers may generate an antibody response (Martin et al. (1995), supra; and Fisher et al. (1996), *The New England Journal of Medicine*, 334 (26):1697–1702).

It is an object of the present invention to provide functionally active truncated sTNFRs. This and other objects of the present invention will become apparent from the description hereinafter.

SUMMARY OF THE INVENTION

The present invention is directed to functionally active truncated forms of sTNFR-I and sTNFR-II, respectively, and are referred to herein as "truncated sTNFR(s)". The truncated sTNFRs are modified forms of sTNFR-I and sTNFR-II which do not contain the fourth domain (amino acid residues $Thr^{127}$-$Asn^{161}$ of sTNFR-I and amino acid residues $Pro^{141}$-$Thr^{179}$ of sTNFR-II); a portion of the third domain (amino acid residues $Asn^{111}$-$Cys^{126}$ of sTNFR-I and amino acid residues $Pro^{123}$-$Lys^{140}$ of sTNFR-II); and, optionally, which do not contain a portion of the first domain (amino acid residues $Asp^1$-$Cys^{19}$ of sTNFR-I and amino acid residues $Leu^1$-$Cys^{32}$ of sTNFR-II). These new inhibitors of TNF (e.g., TNF-α and/or TNF-β) have general applicability.

The truncated sTNFRs of the present invention include the proteins represented by the formula $R_1$-$[Cys^{19}$–$Cys^{103}]$-$R_2$ and $R_4$-$[Cys^{32}$–$Cys^{115}]$-$R_5$. These proteins are truncated forms of sTNFR-I and sTNFR-II, respectively.

By "$R_1$-$[Cys^{19}$–$Cys^{103}]$-$R_2$" is meant one or more proteins wherein $[Cys^{19}$–$Cys^{103}]$ represents residues 19 through 103 of sTNFR-I, the amino acid residue numbering scheme of which is provided in FIG. 1 (SEQ ID NO:2) to facilitate the comparison; wherein $R_1$ represents a methionylated or nonmethionylated amine group of $Cys^{19}$ or of amino-terminus amino acid residue(s) selected from the group:

| | |
|---|---|
| C | |
| IC | |
| SIC | |
| NSIC | (SEQ ID NO:15) |
| NNSIC | (SEQ ID NO:16) |
| QNNSIC | (SEQ ID NO:17) |
| PQNNSIC | (SEQ ID NO:18) |
| HPQNNSIC | (SEQ ID NO:19) |
| IHPQNNSIC | (SEQ ID NO:20) |
| YIHPQNNSIC | (SEQ ID NO:21) |
| KYIHPQNNSIC | (SEQ ID NO:22) |
| GKYIHPQNNSIC | (SEQ ID NO:23) |
| QGKYIHPQNNSIC | (SEQ ID NO:24) |
| PQGKYIHPQNNSIC | (SEQ ID NO:25) |
| CPQGKYIHPQNNSIC | (SEQ ID NO:26) |
| VCPQGKYIHPQNNSIC | (SEQ ID NO:27) |
| SVCPQGKYIHPQNNSIC | (SEQ ID NO:28) |
| DSVCPQGKYIHPQNNSIC | (SEQ ID NO:29); | and wherein $R_2$ represents a carboxy group of $Cys^{103}$ or of carboxy-terminal amino acid residues selected from the group:

| | |
|---|---|
| F | |
| FC | |
| FCC | |
| FCCS | (SEQ ID NO:30) |
| FCCSL | (SEQ ID NO:31) |
| FCCSLC | (SEQ ID NO:32) |
| FCCSLCL | (SEQ ID NO:33); | and variants thereof, provided however, when $R_1$ represents a methionylated or nonmethionylated amine group of amino acid sequence VCPQGKYIHPQNNSIC or an N-terminal truncation thereof of from 1 to 15 residues, then the $R_1$-$[Cys^{19}$–$Cys^{103}]$-$R_2$ protein is not an addition variant having the formula $R_1$-$[Cys^{19}$–$Cys^{103}]$-FCCSLCL-$R_3$, wherein $R_3$ represents a carboxyl group of amino acid sequence $Asn^{111}$–$Asn^{161}$ of FIG. 1 or a carboxy-terminal truncation thereof.

Exemplary truncated sTNFR-I of the present invention include the following molecules: $NH_2$-MDSVCPQGKYIHPQNNSIC-$[Cys^{19}$–$Cys^{103}]$-FC—COOH (also referred to as sTNFR-I 2.6D/C105); $NH_2$-MDSVCPQGKYIHPQNNSIC-$[Cys^{19}$–$Cys^{103}]$-FNCSL-COOH (also referred to as sTNFR-I 2.6D/C106); $NH_2$-MDSVCPQGKYIHPQNNSIC-$[Cys^{19}$–$Cys^{103}]$-FN—COOH (also referred to as sTNFR-I 2.6D/N105); $NH_2$-MYIHPQNNSIC-$[Cys^{19}$–$Cys^{103}]$—FNCSL-COOH (also referred to as sTNFR-I 2.3D/d8); $NH_2$-M-$[Cys^{19}$–$Cys^{103}]$-FNCSL-COOH (also referred to as sTNFR-I 2.3D/d18); and $NH_2$-MSIS-$[Cys^{19}$–$Cys^{103}]$-FNCSL-COOH (also referred to as sTNFR-I 2.3D/d15), either methionylated or nonmethionylated, and variants and derivatives thereof.

By "$R_4$-$[Cys^{32}$–$Cys^{115}]$-$R_5$" is meant one or more proteins wherein $[Cys^{32}$–$Cys^{115}]$ represents residues $Cys^{32}$ through $Cys^{115}$ of sTNFR-I, the amino acid residue numbering scheme of which is provided in FIG. 8 (SEQ ID NO:35) to facilitate the comparison; wherein $R_4$ represents a methionylated or nonmethionylated amine group of $Cys^{32}$ or of amino-terminus amino acid residue(s) selected from the group:

| | |
|---|---|
| C | |
| MC | |
| QMC | |
| AQMC | (SEQ ID NO:36) |
| TAQMC | (SEQ ID NO:37) |
| QTAQMC | (SEQ ID NO:38) |
| DQTAQMC | (SEQ ID NO:39) |
| YDQTAQMC | (SEQ ID NO:40) |

-continued

| | |
|---|---|
| YYDQTAQMC | (SEQ ID NO:41) |
| EYYDQTAQMC | (SEQ ID NO:42) |
| REYYDQTAQMC | (SEQ ID NO:43) |
| LREYYDQTAQMC | (SEQ ID NO:44) |
| RLREYYDQTAQMC | (SEQ ID NO:45) |
| CRLREYYDQTAQMC | (SEQ ID NO:46) |
| TCRLREYYDQTAQMC | (SEQ ID NO:47) |
| STCRLREYYDQTAQMC | (SEQ ID NO:48) |
| GSTCRLREYYDQTAQMC | (SEQ ID NO:49) |
| PGSTCRLREYYDQTAQMC | (SEQ ID NO:50) |
| EPGSTCRLREYYDQTAQMC | (SEQ ID NO:51) |
| PEPGSTCRLREYYDQTAQMC | (SEQ ID NO:52) |
| APEPGSTCRLREYYDQTAQMC | (SEQ ID NO:53) |
| YAPEPGSTCRLREYYDQTAQMC | (SEQ ID NO:54) |
| PYAPEPGSTCRLREYYDQTAQMC | (SEQ ID NO:55) |
| TPYAPEPGSTCRLREYYDQTAQMC | (SEQ ID NO:56) |
| FTPYAPEPGSTCRLREYYDQTAQMC | (SEQ ID NO:57) |
| AFTPYAPEPGSTCRLREYYDQTAQMC | (SEQ ID NO:58) |
| VAFTPYAPEPGSTCRLREYYDQTAQMC | (SEQ ID NO:59) |
| QVAFTPYAPEPGSTCRLREYYDQTAQMC | (SEQ ID NO:60) |
| AQVAFTPYAPEPGSTCRLREYYDQTAQMC | (SEQ ID NO:61) |
| PAQVAFTPYAPEPGSTCRLREYYDQTAQMC | (SEQ ID NO:62) |
| LPAQVAFTPYAPEPGSTCRLREYYDQTAQMC | (SEQ ID NO:63); | and wherein $R_5$ represents a carboxy group of $Cys^{115}$ or of carboxy-terminal amino acid residues selected from the group:

| | |
|---|---|
| A | |
| AP | |
| APL | |
| APLR | (SEQ ID NO:64) |
| APLRK | (SEQ ID NO:65) |
| APLPKC | (SEQ ID NO:66) |
| APLRKCR | (SEQ ID NO:67) | and variants thereof, provided however, when $R_4$ represents a methionylated or nonmethionylated amine group of amino acid sequence TCRLREYYDQTAQMC or an N-terminal truncation thereof of from 1 to 15 residues, then $R_4$-[$Cys^{32}$–$Cys^{115}$]-$R_5$ is not an addition variant having the formula $R_4$-[$Cys^{32}$–$Cys^{115}$]-APLRKCR-$R_6$, wherein $R_6$ represents a carboxyl group of amino acid sequence $Pro^{123}$-$Thr^{179}$ of FIG. 8 or a carboxy-terminal truncation thereof.

In one aspect of the present invention, the truncated sTNFRs may be made in glycosylated or non-glycosylated forms. Truncated sTNFRs are produced by recombinant genetic engineering techniques. In an alternative embodiment, truncated sTNFRs are synthesized by chemical techniques or a combination of the recombinant and chemical techniques.

In another aspect of the present invention, truncated sTNFRs may be derivatized by attaching the truncated sTNFRs to a water soluble polymer. For example, the truncated sTNFRs may be conjugated to one or more polyethylene glycol molecules in order to improve pharmacokinetic performance by increasing the molecule's apparent molecular weight.

Yet another aspect of the present invention includes the various polynucleotides encoding truncated sTNFRs. Suitable nucleic acid sequences include, for example, those specifically depicted in the Figures as well as degenerate sequences and naturally occurring allelic variations thereof. Such nucleic acid sequences may be used in the expression of truncated sTNFRs in eukaryotic or prokaryotic host cells, wherein the expression products or derivatives thereof are characterized by the ability to modulate the activity of TNF.

A further aspect of the present invention involves vectors containing the polynucleotides encoding truncated sTNFRs operatively linked to amplification and/or expression control sequences. Both prokaryotic and eukaryotic host cells may be stably transformed or transfected with such vectors to express the truncated sTNFRs. The present invention further includes the recombinant production of truncated sTNFRs wherein host cells containing such polynucleotides are grown in a suitable nutrient medium and the truncated sTNFRs expressed by the cells are, optionally, isolated from the host cells and/or the nutrient medium.

Another aspect of the present invention includes pharmaceutical compositions containing truncated sTNFRs or derivatives thereof. Typically, the truncated sTNFRs or derivatives thereof may be formulated in association with pharmaceutically acceptable vehicles. A variety of other formulation materials may be used to facilitate manufacture, storage, handling, delivery and/or efficacy of the truncated sTNFRs or derivatives thereof.

Another aspect of the present invention relates to methods of modulating the activity of TNF. Specifically, TNF-mediated diseases (e.g., diseases mediated by TNF-α and/or TNF-β) may be treated by administering to a patient therapeutically effective amounts of truncated sTNFRs or derivatives thereof.

The polynucleotides encoding truncated sTNFRs may also be used in cell therapy or gene therapy applications.

The truncated sTNFRs of the present invention are particularly suited for production of large-scale quantities of protein. For example, sTNFR-I has a deamidation site within the amino acid sequence 111 to 126 (amino acids $Asn^{111}$-$Gly^{126}$). The absence of this site is expected to enhance biochemical stability of the purified protein, decreasing possible degradation products and resulting in more storage-stable proteins. Truncated sTNFRs have fewer disulfide bridges than do other previously disclosed TNF inhibitor proteins. For example, sTNFR-I has two disulfide bridges within the amino acid sequence 111 to 126 and three disulfide bridges within the amino acid sequence 127 to 161; and sTNFR-II has a disulfide bridge between $Cys^{121}$ and $Cys^{139}$, $Cys^{142}$ and $Cys^{157}$, and $Cys^{163}$ and $Cys^{178}$. The reduced number of disulfide bridges is important in that greater numbers of these linkages can complicate the protein refolding process. Surprisingly, truncated sTNFRs have fewer sites for antigenic epitopes than do other previously disclosed TNF inhibitor proteins (e.g., a shortened form of sTNFR-I having the first three domains has neo-epitopes caused by exposing certain residues, see Example III), resulting in comparatively reduced antigenicity and having no significant reduction in clearance rate with repeated administration. The reduced immunogenicity of truncated sTNFRs is expected to be suitable for treatment of TNF-mediated diseases, particularly including chronic inflammatory diseases.

Additional aspects and advantages of the invention will be apparent to those skilled in the art upon consideration of the following description, which details the practice of the present invention.

BRIEF DESCRIPTION OF THE FIGURES

Numerous aspects and advantages of the present invention will become apparent upon review of the figures, wherein:

FIG. 1 depicts a nucleic acid sequence (SEQ ID NO:1) encoding $Asp^1$–$Asn^{161}$, full length recombinant human sTNFR-I. Also depicted is the amino acid sequence (SEQ ID NO:2) of $Asp^1$–$Asn^{161}$.

FIG. 2 depicts a nucleic acid sequence (SEQ ID NO:3) encoding $NH_2$-MDSVCPQGKYIHPQNNSIC-[$Cys^{19}$–$Cys^{103}$]-FC—COOH (also referred to as sTNFR-I 2.6D/C105). Also depicted is the amino acid sequence (SEQ ID NO:4) of $NH_2$-MDSVCPQGKYIHPQNNSIC-[$Cys^{19}$–$Cys^{103}$]-FC—COOH.

FIG. 3 depicts a nucleic acid sequence (SEQ ID NO:5) encoding $NH_2$-MDSVCPQGKYIHPQNNSIC-[$Cys^{19}$–$Cys^{103}$]-FNCSL-COOH (also referred to as sTNFR-I 2.6D/C106). Also depicted is the amino acid sequence (SEQ ID NO:6) of $NH_2$-MDSVCPQGKYIHPQNNSIC-[$Cys^{19}$–$Cys^{103}$]-FNCSL-COOH.

FIG. 4 depicts a nucleic acid sequence (SEQ ID NO:7) encoding $NH_2$-MDSVCPQGKYIHPQNNSIC-[$Cys^{19}$–$Cys^{103}$]-FN—COOH (also referred to as sTNFR-I 2.6D/N105). Also depicted is the amino acid sequence (SEQ ID NO:8) of $NH_2$-MDSVCPQGKYIHPQNNSIC-[$Cys^{19}$–$Cys^{103}$]-FN—COOH.

FIG. 5 depicts a nucleic acid sequence (SEQ ID NO:11) encoding $NH_2$-MYIHPQNNSIC-[$Cys^{19}$–$Cys^{103}$]-FNCSL-COOH (also referred to as sTNFR-I 2.3D/d8). Also depicted is the amino acid sequence (SEQ ID NO:12) of $NH_2$-MDSVCPQGKYIHPQNNSIC-[$Cys^{19}$–$Cys^{103}$]-FNCSL-COOH.

FIG. 6 depicts a nucleic acid sequence (SEQ ID NO:9) encoding $NH_2$-M-[$Cys^{19}$–$Cys^{103}$]-FNCSL-COOH (also referred to as sTNFR-I 2.3D/d18). Also depicted is the amino acid sequence (SEQ ID NO:10) of $NH_2$-M-[$Cys^{19}$–$Cys^{103}$]-FNCSL-COOH.

FIG. 7 depicts a nucleic acid sequence (SEQ ID NO:13) encoding $NH_2$-MSIS-[$Cys^{19}$–$Cys^{103}$]-FNCSL-COOH (also referred to as sTNFR-I 2.3D/d15). Also depicted is the amino acid sequence (SEQ ID NO:14) of $NH_2$-MSIS-[$Cys^{19}$–$Cys^{103}$]-FNCSL-COOH.

FIG. 8 depicts a nucleic acid sequence (SEQ ID NO:34) encoding $Leu^1$-$Thr^{179}$, mature recombinant human sTNFR-II. Also depicted is the amino acid sequence (SEQ ID NO:35) of $Leu^1$-$Thr^{179}$.

FIG. 9 depicts the amount of swelling induced in a Streptococcal cell wall-induced reactivation model, as described in Example II.

DETAILED DESCRIPTION OF THE INVENTION

Figure 10:
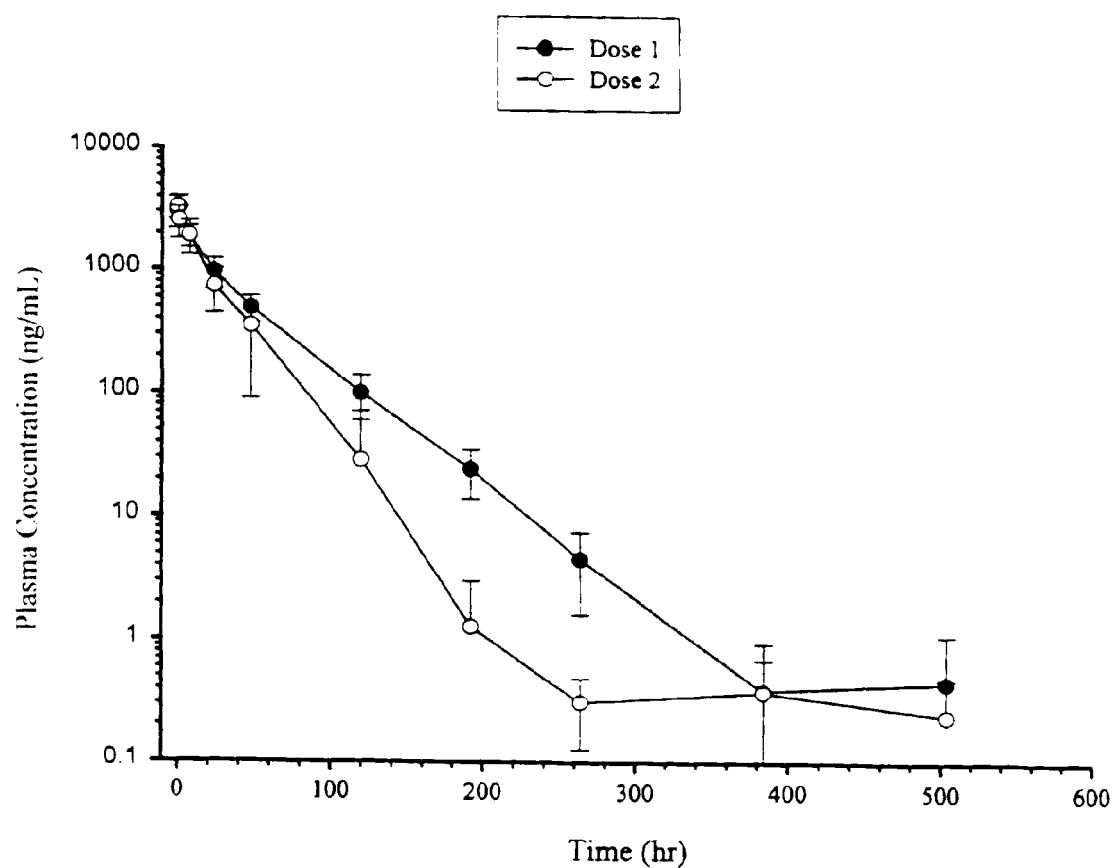
FIG. 10 depicts the plasma profiles of sTNFR-I 4D/C105 db in healthy baboons following two minute intravenous infusion of 0.2 mg/kg, as described in Example III.

The present invention is based on the unexpected discovery that sTNFR-I and sTNFR-II may each be reduced in size to exclude not only the fourth domain but a portion of the third domain and, optionally, a portion of the first domain, and yet retain biological activity and have reduced antigenicity. For at least the following reasons, it is considered advantageous to produce these biologically active truncated sTNFRs or derivatives thereof. First, these molecules may have one less potentially destabilizing deamidation site. Second, these molecules have fewer disulfide bridges, potentially making refolding and purifying easier. Third, these molecules have reduced sites for potential antigenic epitopes.

As used herein, the term "truncated sTNFR(s)" includes one or more biologically active synthetic or recombinant molecules of the formula $R_1$-[$Cys^{19}$–$Cys^{103}$]-$R_2$ or $R_4$-[$Cys^{32}$–$Cys^{115}$]-$R_5$, and variants (including insertion, substitution and deletion variants) thereof, as described below.

The term "biologically active" as used herein means that a truncated sTNFR demonstrates similar TNF inhibiting properties, but not necessarily all of the same properties and not necessarily to the same degree as sTNFR-I and/or sTNFR-II. In general, truncated sTNFRs and derivatives thereof have the ability to inhibit TNF. Bioassays of truncated sTNFRs are further described in Example II below. The selection of the particular TNF-inhibiting properties of interest depends upon the desired use of a truncated sTNFR.

In one aspect of the present invention, truncated sTNFRs may advantageously be produced via recombinant techniques in bacterial, mammalian or insect cell systems and may be either a glycosylated or non-glycosylated forms of the protein. Alternatively, truncated sTNFRs may be chemically synthesized. Currently preferred production methods are described in greater detail below.

Truncated sTNFRs each may typically be isolated and purified to be substantially free from the presence of other proteinaceous materials (i.e., non-truncated sTNFRs). Preferably, a truncated sTNFR is about 80% free of other proteins which may be present due to the production technique used in the manufacture of the truncated sTNFR. More preferably a truncated sTNFR is about 90% free of other proteins, particularly preferably about 95% free of other proteins, and most preferably about >98% free of other proteins. It will be appreciated, however, that the desired protein may be combined with other active ingredients, chemical compositions and/or suitable pharmaceutical formulation materials prior to administration, as described in further detail below.

Truncated sTNFRs

In one basic embodiment, truncated sTNFRs of the present invention may be one or more proteins represented by the following formula:

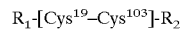

wherein [$Cys^{19}$–$Cys^{103}$] represents residues 19 through 103 of sTNFR-I, the amino acid residue numbering scheme of which is provided in FIG. 1 (SEQ ID NO:2) to facilitate the comparison; wherein $R_1$ represents a methionylated or nonmethionylated amine group of $Cys^{19}$ or of amino-terminus amino acid residue(s) selected from the group:

```
                C
               IC
              SIC
             NSIC       (SEQ ID NO:15)
            NNSIC       (SEQ ID NO:16)
           QNNSIC       (SEQ ID NO:17)
          PQNNSIC       (SEQ ID NO:18)
         HPQNNSIC       (SEQ ID NO:19)
        IHPQNNSIC       (SEQ ID NO:20)
       YIHPQNNSIC       (SEQ ID NO:21)
      KYIHPQNNSIC       (SEQ ID NO:22)
     GKYIHPQNNSIC       (SEQ ID NO:23)
    QGKYIHPQNNSIC       (SEQ ID NO:24)
   PQGKYIHPQNNSIC       (SEQ ID NO:25)
  CPQGKYIHPQNNSIC       (SEQ ID NO:26)
 VCPQGKYIHPQNNSIC       (SEQ ID NO:27)
SVCPQGKYIHPQNNSIC       (SEQ ID NO:28)
DSVCPQGKYIHPQNNSIC      (SEQ ID NO:29);
``` and wherein $R_2$ represents a carboxy group of $Cys^{103}$ or of carboxy-terminal amino acid residues selected from the group:

```
       F
      FC
     FCC
    FCCS        (SEQ ID NO:30)
   FCCSL        (SEQ ID NO:31)
  FCCSLC        (SEQ ID NO:32)
 FCCSLCL        (SEQ ID NO:33);
``` and variants thereof, provided however, when $R_1$ represents a methionylated or nonmethionylated amine group of amino acid sequence VCPQGKYIHPQNNSIC or an N-terminal truncation thereof of from 1 to 15 residues, then $R_1$-$[Cys^{19}-Cys^{103}]$-$R_2$ is not an addition variant having the formula $R_1$-$[Cys^{19}-Cys^{103}]$-FCCSLCL-$R_3$, wherein $R_3$ represents a carboxyl group of amino acid sequence $Asn^{111}$–$Asn^{161}$ of FIG. 1 or a carboxy-terminal truncation thereof.

In another basic embodiment, truncated sTNFRs of the present invention may be one or more proteins represented by the following formula:

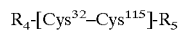

wherein $[Cys^{32}-Cys^{115}]$ represents residues $Cys^{32}$ through $Cys^{115}$ of sTNFR-II, the amino acid residue numbering scheme of which is provided in FIG. 8 (SEQ ID NO:35) to facilitate the comparison; wherein $R_4$ represents a methionylated or nonmethionylated amine group of $Cys^{32}$ or of amino-terminus amino acid residue(s) selected from the group:

```
                 C
                MC
               QMC
              AQMC       (SEQ ID NO:36)
             TAQMC       (SEQ ID NO:37)
            QTAQMC       (SEQ ID NO:38)
           DQTAQMC       (SEQ ID NO:39)
          YDQTAQMC       (SEQ ID NO:40)
         YYDQTAQMC       (SEQ ID NO:41)
        EYYDQTAQMC       (SEQ ID NO:42)
       REYYDQTAQMC       (SEQ ID NO:43)
      LREYYDQTAQMC       (SEQ ID NO:44)
     RLREYYDQTAQMC       (SEQ ID NO:45)
    CRLREYYDQTAQMC       (SEQ ID NO:46)
   TCRLREYYDQTAQMC       (SEQ ID NO:47)
  STCRLREYYDQTAQMC       (SEQ ID NO:48)
 GSTCRLREYYDQTAQMC       (SEQ ID NO:49)
PGSTCRLREYYDQTAQMC       (SEQ ID NO:50)
EPGSTCRLREYYDQTAQMC      (SEQ ID NO:51)
PEPGSTCRLREYYDQTAQMC     (SEQ ID NO:52)
APEPGSTCRLREYYDQTAQMC    (SEQ ID NO:53)
YAPEPGSTCRLREYYDQTAQMC   (SEQ ID NO:54)
PYAPEPGSTCRLREYYDQTAQMC  (SEQ ID NO:55)
TPYAPEPGSTCRLREYYDQTAQMC (SEQ ID NO:56)
FTPYAPEPGSTCRLREYYDQTAQMC (SEQ ID NO:57)
AFTPYAPEPGSTCBLREYYDQTAQMC (SEQ ID NO:58)
VAFTPYAPEPGSTCRLREYYDQTAQMC (SEQ ID NO:59)
QVAFTPYAPEPGSTCRLREYYDQTAQMC (SEQ ID NO:60)
AQVAFTPYAPEPGSTCRLREYYDQTAQMC (SEQ ID NO:61)
PAQVAFTPYAPEPGSTCRLREYYDQTAQMC (SEQ ID NO:62)
LPAQVAFTPYAPEPGSTCRLREYYDQTAQMC (SEQ ID NO:63);
``` and wherein $R_5$ represents a carboxy group of $Cys^{115}$ or of carboxy-terminal amino acid residues selected from the group:

```
   A
  AP
 APL
```

-continued

| APLR | (SEQ ID NO:64) |
|---|---|
| APLRK | (SEQ ID NO:65) |
| APLRKC | (SEQ ID NO:66) |
| APLRKCR | (SEQ ID NO:67) | and variants thereof, provided however, when $R_4$ represents a methionylated or nonmethionylated amine group of amino acid sequence TCRLREYYDQTAQMC or an N-terminal truncation thereof of from 1 to 15 residues, then $R_4$-[$Cys^{32}$–$Cys^{115}$]-$R_5$ is not an addition variant having the formula $R_4$-[$Cys^{32}$–$Cys^{115}$]-APLRKCR-$R_6$, wherein $R_6$ represents a carboxyl group of amino acid residues $Pro^{123}$-$Thr^{179}$ of FIG. 8 or a carboxy-terminal truncation thereof.

Another aspect of the present invention includes one or more variants of $R_1$-[$Cys^{19}$–$Cys^{103}$]-$R_2$ and $R_4$-[$Cys^{32}$–$Cys^{115}$]-$R_5$, either methionylated or nonmethionylated. The term "truncated sTNFR(s)" thus includes one or more naturally-occurring allelic variants of $R_1$-[$Cys^{19}$–$Cys^{103}$]-$R_2$ and $R_4$-[$Cys^{32}$–$Cys^{115}$]-$R_5$, and one or more other variant proteins in which amino acids have been deleted from ("deletion variants"), inserted into ("addition variants"), or substituted for ("substitution variants") residues within the amino acid sequences of $R_1$-[$Cys^{19}$–$Cys^{103}$]-$R_2$ or $R_4$-[$Cys^{32}$–$Cys^{115}$]-$R_5$.

Amino acid sequence deletions typically range from about 20 amino acid residues, more typically from about 1 to 10 residues, and most typically from about 1 to 5 residues, so as not to disrupt protein folding. N-terminal, C-terminal and internal intrasequence deletions are contemplated. The number of total deletions and/or consecutive deletions will be selected so as to preserve the tertiary structure of the protein in the affected domain, e.g., cysteine crosslinking.

Deletions within the $R_1$-[$Cys^{19}$–$Cys^{103}$]-$R_2$ amino acid sequence and within the $R_4$-[$Cys^{32}$–$Cys^{115}$]-$R_5$ amino acid sequence may be made in regions of low homology with the sequences of other members of the NGF/TNF receptor family in the group of cell surface membrane proteins. Deletions within the $R_1$-[$Cys^{19}$–$Cys^{103}$]-$R_2$ amino acid sequence and within the $R_4$-[$Cys^{32}$–$Cys^{115}$]-$R_5$ amino acid sequence may be made in areas of substantial homology with the sequences of other members of the NGF/TNF receptor family and will be more likely to significantly modify the biological activity. Specifically, the sequence similarity among NGF/TNF receptor family members is particularly high in the region corresponding to the first two disulfide loops of domain 1, the whole of domain 2, and the first disulfide loop of domain 3 (Banner et al. (1993), Cell, 73:431–445). For example, two exemplary deletion variants of $R_1$-[$Cys^{19}$–$Cys^{103}$]-$R_2$ are $R_1$-[$Cys^{19}$($\Delta Thr^{20}$)-$Cys^{103}$]-$R_2$ and $R_1$-[$Cys^{19}$($\Delta Cys^{19}$-$Lys^{21}$)-$Cys^{103}$]-$R_2$, wherein $R_1$ and $R_2$ are as defined above. For example, three exemplary deletion variants of $R_4$-[$Cys^{32}$–$Cys^{115}$]-$R_5$ are $R_4$-[$Cys^{32}$-($\Delta Cys^{115}$)$Cys^{115}$]-$R_5$; $R_1$-[$Cys^{19}$($\Delta Cys^{115}$-$Lys^{115}$)-$Cys^{103}$]-$R_2$ and $R_4$-[$Cys^{32}$-($\Delta Cys^{115}$-$Arg^{113}$)$Cys^{115}$]-$R_5$, wherein $R_1$ and $R_2$ are as defined above.

Amino acid sequence additions may include amino- and/or carboxyl-terminal fusions ranging in length from one residue to one hundred or more residues, as well as internal intrasequence insertions of single or multiple amino acid residues. Internal additions may range typically from about 1 to 10 amino acid residues, more typically from about 1 to 5 amino acid residues and most typically from about 1 to 3 amino acid residues.

Amino-terminus addition variants include the addition of a methionine (for example, as an artifact of the direct expression of the protein in bacterial recombinant cell culture) or an additional amino acid residue or sequence. A further example of an amino-terminal insertion includes the fusion of a signal sequence, as well as or with other pre-pro sequences, to facilitate the secretion of protein from recombinant host cells. For prokaryotic host cells that do not recognize and process the native sTNFR-I or sTNFR-II signal sequences, the signal sequence may be substituted by a prokaryotic signal sequence selected, for example, from the group of the alkaline phosphatase, penicillinase or heat-stable enterotoxin II leaders. For yeast cells, the signal sequence may be selected, for example, from the group of the yeast invertase, alpha factor or acid phosphatase leader sequences. In mammalian cell expression the native signal sequences of sTNFR-I or of sTNFR-II (EP 393 438 and EP 422 339) are satisfactory, although other mammalian signal sequences may be suitable (e.g., sequences derived from other NGF/TNF receptor family members).

Carboxy-terminus addition variants do not involve the addition of one or more amino acid residues that would result in the reconstruction of the sTNFR-I or of sTNFR-II, respectively. It will be appreciated that a carboxy-terminus addition variant will not include the addition of one or more carboxy acid residues that would result in the reconstruction of the third domain or fourth domain of sTNFR-I or sTNFR-II. An example of carboxy-terminus addition variants includes chimeric proteins comprising the fusion of $R_1$-[$Cys^{19}$–$Cys^{103}$]-$R_2$ or $R_4$-[$Cys^{32}$–$Cys^{115}$]-$R_5$ with all or part of a constant domain of a heavy or light chain of human immunoglobulin. Such chimeric proteins are preferred wherein the immunoglobulin portion of each comprises all domains except the first domain of the constant region of the heavy chain of human immunoglobulin, such as IgG, IgA, IgM or IgE, especially IgG, e.g., IgG1 or IgG3. A skilled artisan will appreciate that any amino acid of each immunoglobulin portion can be deleted or substituted with one or more amino acids, or one or more amino acids can be added as long as the TNF binding portion still binds TNF and the immunoglobulin portion shows one or more of its characteristic properties.

Another group of variants are amino acid substitution variants. These variants each have at least one amino acid residue in $R_1$-[$Cys^{19}$–$Cys^{103}$]-$R_2$ or $R_4$-[$Cys^{32}$–$Cys^{115}$]-$R_5$ removed and a different residue inserted in its place. Substitution variants include allelic variants, which are characterized by naturally-occurring nucleotide sequence changes in the species population that may or may not result in an amino acid change. One skilled in the art can use any information known about the binding or active site of the polypeptide in the selection of possible mutation sites.

One method for identifying amino acid residues or regions for mutagenesis of a protein is called "alanine scanning mutagenesis" (Cunningham and Wells (1989), Science, 244:1081–1085, the disclosure of which is hereby incorporated by reference). In this method, an amino acid residue or group of target residues of a protein is identified (e.g., charged residues such as Arg, Asp, His, Lys and Glu) and replaced by a neutral or negatively-charged amino acid (most preferably alanine or polyalanine) to effect the interaction of the amino acids with the surrounding aqueous environment in or outside the cell. Those residues demonstrating functional sensitivity to the substitutions are then refined by introducing additional or alternate residues at the sites of substitution. Thus, the site for introducing an amino acid sequence modification is predetermined and, to optimize the performance of a mutation at a given site, alanine scanning or random mutagenesis may be conducted and the resulting variant polypeptide screened for the optimal combination of desired activity and degree of activity.

Sites of interest for substitutional mutagenesis include sites where the amino acids found in $R_1$-[$Cys^{19}$–$Cys^{103}$]-$R_2$ or $R_4$-[$Cys^{32}$–$Cys^{115}$]-$R_5$ are substantially different in terms of side-chain bulk, charge and/or hydrophobicity from sTNFR-like proteins such as sTNFRs of other various species or of other members of the NGF/TNF receptor family.

Other sites of interest include those in which particular residues are similar or identical with those of such sTNFR-I-like proteins and sTNFR-II-like proteins. Such positions are generally important for the biological activity of a protein. For example, a skilled artisan would have understood that prior to the present invention, the effects of truncating sTNFR-I and sTNFR-II on the their respective three-dimensional structures would not have been predictable. However, given the results disclosed herein, a skilled artisan would appreciate the first principles of developing a strategy for making variants could rely in part on the information previously elucidated for the full length sTNFR-I and sTNFR-II. Accordingly, the following information has been elucidated concerning sTNFR-I (Banner et al. (1993), supra, and Fu et al. (1995), *Protein Engineering*, 8(12):1233–1241). Residues $Tyr^9$, $Thr^{39}$, $His^{55}$ in Domain 1, residues $Phe^{49}$, $Ser^{63}$, $Asp^{82}$ in Domain 2 and residues $Tyr^{92}$ and $Ser^{107}$ in Domain 3 have been identified as being potentially important for the stabilization of the structure of Domains 1, 2 and 3, respectively. Residues $Pro^{12}$ and $His^{55}$ have been identified as potentially interacting with $Ser^{86}$–$Tyr^{87}$ on subunit C of TNFα. Residues $Glu^{45}$-$Phe^{49}$ have been identified as being in a loop which potentially interacts with residues $Leu^{29}$-$Arg^{32}$ of TNFα subunit A. Residues $Gly^{48}$ has been identified as potentially interacting with $Asn^{19}$-$Pro^{20}$ on subunit A of TNFα. Residue $His^{58}$-$Leu^{60}$ have been identified as being in an extended strand conformation and side chain interactions with residues $Arg^{31}$-$Ala^{33}$ on subunit A of TNFα have been potentially identified with residue $His^{58}$ of sTNFR-I specifically interacting with residue $Arg^{31}$. Residues $Lys^{64}$-$Arg^{66}$ have been identified as being in an extended strand conformation and have been identified as having side chain and main chain interactions with residues $Ala^{145}$–$Glu^{146}$ and residue $Glu^{46}$ on subunit A of TNFα. Residue $Met^{69}$ has been identified as potentially interacting with residue $Tyr^{115}$ on subunit A of TNFα. Residues $His^{94}$-$Phe^{101}$ have been identified as forming a loop which interacts with residues $Thr^{72}$-$Leu^{75}$ and $Asn^{137}$ of subunit C of TNFα, with residue $Trp^{96}$ of sTNFR-I specifically interacting with residues $Ser^{71}$-$Thr^{72}$ on subunit C of TNFα, $Leu^{100}$ of sTNFR-I being in close proximity with residue $Asn^{137}$ on subunit C of TNFα and residue $Gln^{102}$ of sTNFR-I specifically interacting with residue $Pro^{113}$ on subunit A of TNFα. Accordingly, a skilled artisan would appreciate that initially these sites should be modified by substitution in a relatively conservative manner.

Such conservative substitutions are shown in Table 1 under the heading of "Preferred Substitutions". If such substitutions result in a change in biological activity, then more substantial changes (Exemplary Substitutions) may be introduced and/or other additions/deletions may be made and the resulting products screened.

TABLE 1

Amino Acid Substitutions

| Original Residue | Preferred Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Lys; Arg |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Arg | Asn; Gln; Lys; Arg |
| Ile (I) | Leu | Leu; Val; Met; Ala; Phe; norleucine |
| Leu (L) | Ile | norleucine; Ile; Val; Met; Ala; Phe |
| Lys (K) | Arg | Arg; Gln; Asn |
| Met (M) | Leu | Leu; Phe; Ile |
| Phe (F) | Leu | Leu; Val; Ile; Ala |
| Pro (P) | Gly | Gly |
| Ser (S) | Thr | Thr |
| Thr (T) | Ser | Ser |
| Trp (W) | Tyr | Tyr |
| Tyr (Y) | Phe | Trp; Phe; Thr; Ser |
| Val (V) | Leu | Ile; Leu; Met; Phe; Ala; norleucine |

In making such changes of an equivalent nature, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle (1982), *J. Mol. Biol.*, 157:105–131, the disclosure of which are incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case.

U.S. Pat. No. 4,554,101, the disclosure of which are incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

U.S. Pat. No. 4,554,101 also teaches the identification and preparation of epitopes from primary amino acid sequences on the basis of hydrophilicity. Through the methods disclosed in U.S. Pat. No. 4,554,101 one of skill in the art would be able to identify epitopes from within an amino acid sequence such as the sTNFRs sequences disclosed herein. These regions are also referred to as "epitopic core regions".

Numerous scientific publications have been devoted to the prediction of secondary structure, and to the identification of epitopes, from analyses of amino acid sequences (Chou and Fasman (1974), *Biochemistry,* 13(2):222–245; Chou and Fasman, *Biochemistry,* 113(2):211–222; Chou and Fasman (1978), *Adv. Enzymol. Relat. Areas Mol. Biol.,* 47:45–148; Chou and Fasman, *Ann. Rev. Biochem.,* 47:251–276 and Chou and Fasman (1979), *Biophys. J.,* 26:367–384, the disclosures of which are incorporated herein by reference). Moreover, computer programs are currently available to assist with predicting antigenic portions and epitopic core regions of proteins. Examples include those programs based upon the Jameson-Wolf analysis (Jameson and Wolf (1998), *Comput. Appl. Biosci.,* 4(1):181–186 and Wolf et al. (1988), *Comput. Appl. Biosci.,* 4(1):187–191, the disclosures of which are incorporated herein by reference), the program PepPlot® (Brutlag et al. (1990) *CABS,* 6:237–245 and Weinberger et al. (1985), *Science,* 228:740–742, the disclosures of which are incorporated herein by reference), and other new programs for protein tertiary structure prediction (Fetrow and Bryant (1993), *BIOTECHNOLOGY,* 11:479–483, the disclosure of which are incorporated herein by reference).

Conservative modifications to the amino acid sequences (and the corresponding modifications to the encoding nucleic acid sequences) of $R_1$-[$Cys^{19}$–$Cys^{103}$]-$R_2$ and $R^4$-[$Cys^{32}$–$Cys^{115}$]-$R_5$ are expected to produce proteins having similar functional and chemical characteristics to the modified protein.

In contrast, substantial modifications in the functional and/or chemical characteristics of $R_1$-[$Cys^{19}$–$Cys^{103}$]-$R_2$ and $R_4$-[$Cys^{32}$–$Cys^{115}$]-$R_5$ may be accomplished by selecting substitutions that differ significantly in their effect on maintaining (a) the structure of the polypeptide backbone in the area of the substitution, for example, as a sheet or helical conformation, (b) the charge or hydrophobicity of the protein at the target site or (c) the bulk of the side chain. Naturally-occurring residues are divided into groups based on common side chain properties:

1) hydrophobic: norleucine, Met, Ala, Val, Leu, Ile;

2) neutral hydrophilic: Cys, Ser, Thr;

3) acidic: Asp, Glu;

4) basic: Asn, Gln, His, Lys, Arg;

5) residues that influence chain orientation: Gly, Pro; and 6) aromatic: Trp, Tyr, Phe.

Non-conservative substitutions may involve the exchange of a member of one of these groups for another. Such substituted residues may be introduced into regions of $R_1$-[$Cys^{19}$–$Cys^{103}$]-$R_2$ and $R_4$-[$Cys^{32}$–$Cys^{115}$]-$R_5$ that are homologous or non-homologous with other NGF/TNF receptor family members.

Specific mutations of the sequences of $R_1$-[$Cys^{19}$–$Cys^{103}$]-$R_2$ and $R_4$-[$Cys^{32}$–$Cys^{115}$]-$R_5$ may involve substitution of a non-native amino acid at the N-terminus, C-terminus or at any site of the protein that is modified by the addition of an N-linked or O-linked carbohydrate. Such modifications may be of particular utility, such as in the addition of an amino acid (e.g., cysteine), which is advantageous for the linking of a water soluble polymer to form a derivative, as described below. See, for example, FIG. 5 wherein naturally-occurring $Asn^{105}$ of the sTNFR-I is changed to Cys to facilitate the attachment of a polyethylene glycol molecule (Example I).

Further, the sequences of $R_1$-[$Cys^{19}$–$Cys^{103}$]-$R_2$ and $R_4$-[$Cys^{32}$–$Cys^{115}$]-$R_5$ may be modified to add glycosylation sites or to delete N-linked or O-linked glycosylation sites. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. Proven or predicted asparagine residues of sTNFR-I exist at positions 14, 105 and 111. Proven or predicted asparagine residues of sTNFR-II exist at positions 149 and 171. A variety of amino acid substitutions or deletions may be made to modify or add N-linked or O-linked glycosylation sites, resulting in a protein with altered glycosylation.

In a specific embodiment, the variants are substantially homologous to the amino acid of $R_1$-[$Cys^{19}$–$Cys^{103}$]-$R_2$ or $R_4$-[$Cys^{32}$–$Cys^{115}$]-$R_5$. The term "substantially homologous" as used herein means a degree of homology that is preferably in excess of 70%, more preferably in excess of 80%, even more preferably in excess of 90% or most preferably even 95%. The percentage of homology as described herein is calculated as the percentage of amino acid residues found in the smaller of the two sequences which align with identical amino acid residues in the sequence being compared when four gaps in a length of 100 amino acids may be introduced to assist in that alignment, as set forth by Dayhoff (1972), in *Atlas of Protein Sequence and Structure,* 5:124, National Biochemical Research Foundation, Washington, D.C., the disclosure of which is hereby incorporated by reference. Also included as substantially homologous are truncated sTNFRs which may be isolated by virtue of cross-reactivity with antibodies to the amino acid sequences of SEQ ID NO:2 and SEQ ID NO:35, respectively, or whose genes may be isolated through hybridization with the DNA of SEQ ID NO:1 or SEQ ID NO:34 or with segments thereof.

Exemplary sTNFRs of the present invention include the following molecules: NH$_2$-MDSVCPQGKYIHPQNNSIC-[$Cys^{119}$–$Cys^{103}$]-FC—COOH (also referred to as sTNFR-I 2.6D/C105); NH$_2$-MDSVCPQGKYIHPQNNSIC-[$Cys^{19}$–$Cys^{103}$]-FNCSL-COOH (also referred to as sTNFR-I 2.6D/C106); NH$_2$-MDSVCPQGKYIHPQNNSIC-[$Cys^{19}$–$Cys^{103}$]-FN—COOH (also referred to as sTNFR-I 2.6D/N105); NH$_2$-MYIHPQNNSIC-[$Cys^{19}$–$Cys^{103}$]-FNCSL-COOH (also referred to as sTNFR-I 2.3D/d8); NH$_2$-M-[$Cys^{19}$–$Cys^{103}$]-FNCSL-COOH (also referred to as sTNFR-I 2.3D/d18); and NH$_2$-MSIS-[$Cys^{19}$–$Cys^{103}$]-FNCSL-COOH (also referred to as sTNFR-I 2.3D/d15), either methionylated or nonmethionylated, and variants and derivatives thereof.

The production of variant truncated sTNFRs is described in further detail below. Such variants may be prepared by introducing appropriate nucleotide changes into the DNA encoding the truncated sTNFRs or by in vitro chemical synthesis of the desired truncated sTNFRs. It will be appreciated by those skilled in the art that many combinations of deletions, insertions and substitutions can be made, provided that the final truncated sTNFRs are biologically active.

Mutagenesis techniques for the replacement, insertion or deletion of one or more selected amino acid residues are well known to one skilled in the art (e.g., U.S. Pat. No. 4,518,584, the disclosure of which is hereby incorporated by reference). There are two principal variables in the construction of each amino acid sequence variant, the location of the mutation site and the nature of the mutation. In designing each variant, the location of each mutation site and the nature of the mutation will depend on the biochemical characteristic(s) to be modified. Each mutation site can be modified individually or in series, e.g., by (1) substituting first with conservative amino acid choices and then with more radical selections, depending upon the results achieved, (2) deleting the target amino acid residue or (3) inserting amino acid residues adjacent to the located site.

Chemically modified derivatives of truncated sTNFRs may be prepared by one skilled in the art, given the disclosures herein. Conjugates may be prepared using glycosylated, non-glycosylated or de-glycosylated truncated sTNFRs. Typically, non-glycosylated truncated sTNFRs will be used. Suitable chemical moieties for derivatization of truncated sTNFRs include water soluble polymers.

Water soluble polymers are desirable because the protein to which each is attached will not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically and, if so, the desired dosage, circulation time and resistance to proteolysis.

Suitable, clinically acceptable, water soluble polymers include, but are not limited to, polyethylene glycol (PEG), polyethylene glycol propionaldehyde, copolymers of ethylene glycol/propylene glycol, monomethoxy-polyethylene glycol, carboxymethylcellulose, dextran, polyvinyl alcohol (PVA), polyvinyl pyrrolidone, poly-1,3-dioxolane, poly-1,3, 6-trioxane, ethylene/maleic anhydride copolymer, poly (β-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, polyoxyethylated polyols (POG) (e.g., glycerol) and other polyoxyethylated polyols, polyoxyethylated sorbitol, or polyoxyethylated glucose, colonic acids or other carbohydrate polymers, Ficoll or dextran and mixtures thereof.

As used herein, polyethylene glycol is meant to encompass any of the forms that have been used to derivatize other proteins, such as mono-(C1–C10) alkoxy- or aryloxy-polyethylene glycol. Polyethylene glycol propionaldehyde may have advantages in manufacturing due to its stability in water.

The water soluble polymers each may be of any molecular weight and may be branched or unbranched. The water soluble polymers each typically have an average molecular weight of between about 2 kDa to about 100 kDa (the term "about" indicating that in preparations of a water soluble polymer, some molecules will weigh more, some less, than the stated molecular weight). The average molecular weight of each water soluble polymer preferably is between about 5 kDa and about 50 kDa, more preferably between about 12 kDa and about 40 kDa and most preferably between about 20 kDa and about 35 kDa.

Generally, the higher the molecular weight or the more branches, the higher the polymer:protein ratio. Other sizes may be used, depending on the desired therapeutic profile (e.g., the duration of sustained release; the effects, if any, on biological activity; the ease in handling; the degree or lack of antigenicity and other known effects of a water soluble polymer on a therapeutic protein).

The water soluble polymers each should be attached to the protein with consideration of effects on functional or antigenic domains of the protein. In general, chemical derivatization may be performed under any suitable condition used to react a protein with an activated polymer molecule. Activating groups which can be used to link the water soluble polymer to one or more proteins include the following: sulfone, maleimide, sulfhydryl, thiol, triflate, tresylate, azidirine, oxirane and 5-pyridyl.

The water soluble polymers each are generally attached to the protein at the α- or ε-amino groups of amino acids or a reactive thiol group, but it is also contemplated that a water soluble group could be attached to any reactive group of the protein which is sufficiently reactive to become attached to a water soluble group under suitable reaction conditions. Thus, a water soluble polymer may be covalently bound to a protein via a reactive group, such as a free amino or carboxyl group. The amino acid residues having a free amino group may include lysine residues and the N-terminal amino acid residue. Those having a free carboxyl group may include aspartic acid residues, glutamic acid residues and the C-terminal amino acid residue. Those having a reactive thiol group include cysteine residues.

Methods for preparing proteins conjugated with water soluble polymers will each generally comprise the steps of (a) reacting a protein with a water soluble polymer under conditions whereby the protein becomes attached to one or more water soluble polymers and (b) obtaining the reaction product. Reaction conditions for each conjugation may be selected from any of those known in the art or those subsequently developed, but should be selected to avoid or limit exposure to reaction conditions such as temperatures, solvents and pH levels that would inactivate the protein to be modified. In general, the optimal reaction conditions for the reactions will be determined case-by-case based on known parameters and the desired result. For example, the larger the ratio of water soluble polymer:protein conjugate, the greater the percentage of conjugated product. The optimum ratio (in terms of efficiency of reaction in that there is no excess unreacted protein or polymer) may be determined by factors such as the desired degree of derivatization (e.g., mono-, di-, tri-, etc.), the molecular weight of the polymer selected, whether the polymer is branched or unbranched and the reaction conditions used. The ratio of water soluble polymer (e.g., PEG) to protein will generally range from 1:1 to 100:1. One or more purified conjugates may be prepared from each mixture by standard purification techniques, including among others, dialysis, salting-out, ultrafiltration, ion-exchange chromatography, gel filtration chromatography and electrophoresis.

One may specifically desire an N-terminal chemically modified protein. One may select a water soluble polymer by molecular weight, branching, etc., the proportion of water soluble polymers to protein (or peptide) molecules in the reaction mix, the type of reaction to be performed, and the method of obtaining the selected N-terminal chemically modified protein. The method of obtaining the N-terminal chemically modified protein preparation (i.e., separating this moiety from other monoderivatized moieties if necessary) may be by purification of the N-terminal chemically modified protein material from a population of chemically modified protein molecules. Selective N-terminal chemical modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved. For example, one may selectively attach a water soluble polymer to the N-terminus of the protein by performing the reaction at a pH which allows one to take advantage of the pKa differences between the ε-amino group of the lysine residues and that of the α-amino group of the N-terminal residue of the protein. By such selective derivatization, attachment of a water soluble polymer to a protein is controlled: the conjugation with the polymer takes place predominantly at the N-terminus of the protein and no significant modification of other reactive groups, such as the lysine side chain amino groups, occurs. Using reductive alkylation, the water soluble polymer may be of the type described above and should have a single reactive aldehyde for coupling to the protein. Polyethylene glycol propionaldehyde, containing a single reactive aldehyde, may be used.

The present invention specifically contemplates the chemically derivatized protein to include mono- or poly- (e.g., 2–4) PEG moieties. Pegylation may be carried out by any of the pegylation reactions known in the art. Methods for preparing a pegylated protein product will generally comprise the steps of (a) reacting a protein product with polyethylene glycol (such as a reactive ester or aldehyde derivative of PEG) under conditions whereby the protein becomes attached to one or more PEG groups and (b) obtaining the reaction product(s). In general, the optimal reaction conditions for the reactions will be determined case-by-case based on known parameters and the desired result.

There are a number of attachment methods available to those skilled in the art. See, for example, EP 0 401 384, the disclosure of which is hereby incorporated by reference; see also, Malik et al. (1992), *Exp. Hematol.*, 20:1028–1035; Francis (1992), *Focus on Growth Factors*, 3(2):4–10, (published by Mediscript, Mountain Court, Friern Barnet Lane, London N20 OLD, UK); EP 0 154 316; EP 0 401 384; WO 92/16221; WO 95/34326; and the other publications cited herein that relate to pegylation, the disclosures of which are hereby incorporated by reference.

The pegylation specifically may be carried out via an acylation reaction or an alkylation reaction with a reactive polyethylene glycol molecule. Thus, protein products according to the present invention include pegylated proteins wherein the PEG group(s) is (are) attached via acyl or alkyl groups. Such products may be mono-pegylated or poly-pegylated (e.g., containing 2–6, and preferably 2–5, PEG groups). The PEG groups are generally attached to the protein at the α- or ε-amino groups of amino acids, but it is also contemplated that the PEG groups could be attached to any amino group attached to the protein which is sufficiently reactive to become attached to a PEG group under suitable reaction conditions.

Pegylation by acylation generally involves reacting an active ester derivative of polyethylene glycol (PEG) with the protein. For the acylation reactions, the polymer(s) selected should have a single reactive ester group. Any known or subsequently discovered reactive PEG molecule may be used to carry out the pegylation reaction. A preferred activated PEG ester is PEG esterified to N-hydroxysuccinimide (NHS). As used herein, "acylation" is contemplated to include, without limitation, the following types of linkages between the therapeutic protein and a water soluble polymer such as PEG: amide, carbamate, urethane, and the like (see Chamow (1994), *Bioconjugate Chem.*, 5(2):133–140, the disclosure of which are incorporated herein by reference). Reaction conditions may be selected from any of those known in the pegylation art or those subsequently developed, but should avoid conditions such as temperature, solvent and pH that would inactivate the protein to be modified.

Pegylation by acylation will generally result in a poly-pegylated protein. Preferably, the connecting linkage will be an amide. Also preferably, the resulting product will be substantially only (e.g., >95%) mono, di- or tri-pegylated. However, some species with higher degrees of pegylation may be formed in amounts depending on the specific reaction conditions used. If desired, more purified pegylated species may be separated from the mixture (particularly unreacted species) by standard purification techniques, including among others, dialysis, salting-out, ultrafiltration, ion-exchange chromatography, gel filtration chromatography and electrophoresis.

Pegylation by alkylation generally involves reacting a terminal aldehyde derivative of PEG with the protein in the presence of a reducing agent. For the reductive alkylation reaction, the polymer(s) selected should have a single reactive aldehyde group. An exemplary reactive PEG aldehyde is polyethylene glycol propionaldehyde, which is water stable, or mono C1–C10 alkoxy or aryloxy derivatives thereof (see, U.S. Pat. No. 5,252,714, the disclosure of which are incorporated herein by reference).

Pegylation by alkylation can also result in poly-pegylated protein. In addition, one can manipulate the reaction conditions to substantially favor pegylation only at the α-amino group of the N-terminus of the protein (i.e., a mono-pegylated protein). In either case of monopegylation or polypegylation, the PEG groups are preferably attached to the protein via a —CH$_2$—NH— group. With particular reference to the —CH$_2$— group, this type of linkage is referred to herein as an "alkyl" linkage.

Reductive alkylation to produce a substantially homogeneous population of mono-polymer/protein product will generally comprise the steps of: (a) reacting a protein with a reactive PEG molecule under reductive alkylation conditions, at a pH suitable to permit selective modification of the α-amino group at the amino terminus of said protein and (b) obtaining the reaction product(s). Derivatization via reductive alkylation to produce a monopegylated product exploits pKa differences between the lysine amino groups and the α-amino group at the N-terminus (the pKa being the pH at which 50% of the amino groups are protonated and 50% are not).

The reaction is performed at a pH which allows one to take advantage of the pKa differences between the ε-amino groups of the lysine residues and that of the α amino group of the N-terminal residue of the protein. In general, if the pH is lower, a larger excess of polymer to protein will be desired (i.e., the less reactive the N-terminal α-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3–9, preferably 3–6. For the reductive alkylation, the reducing agent should be stable in aqueous solution and preferably be able to reduce only the Schiff base formed in the initial process of reductive alkylation. Suitable reducing agents may be selected from sodium borohydride, sodium cyanoborohydride, dimethylamine borane, trimethylamine borane and pyridine borane. A particularly suitable reducing agent is sodium cyanoborohydride. Other reaction parameters such as solvent, reaction times, temperatures and means of purification of products can be determined case-by-case, based on the published information relating to derivatization of proteins with water soluble polymers.

By such selective derivatization, attachment of a water soluble polymer (that contains a reactive group such as an aldehyde) to a protein is controlled: the conjugation with the polymer takes place predominantly at the N-terminus of the protein and no significant modification of other reactive groups, such as the lysine side chain amino groups, occurs. The preparation will typically be greater than 90% monopolymer/protein conjugate, and more typically greater than 95% monopolymer/protein conjugate, with the remainder of observable molecules being unreacted (i.e., protein lacking the polymer moiety).

A specific embodiment of the present invention is an unbranched monomethoxy-polyethylene glycol aldehyde molecule having an average molecular weight of either about 20 kDa or about 33 kDa (e.g., between 30 kDa and 35 kDa), or a tertiary-butyl polyethylene glycol aldehyde having an average molecular weight of about 33 kDa (e.g., between 30 kDa and 35 kDa) conjugated via reductive alkylation to sTNFR-I 2.6D/N105.

The pegylation also may specifically be carried out via water soluble polymers having at least one reactive hydroxy group (e.g. polyethylene glycol) can be reacted with a reagent having a reactive carbonyl, nitrile or sulfone group to convert the hydroxyl group into a reactive Michael acceptor, thereby forming an "activated linker" useful in modifying various proteins to provide improved biologically-active conjugates. "Reactive carbonyl, nitrile or sulfone" means a carbonyl, nitrile or sulfone group to which a two carbon group is bonded having a reactive site for thiol-specific coupling on the second carbon from the carbonyl, nitrile or sulfone group (WO 92/16221).

The activated linkers can be monofunctional, bifunctional, or multifunctional. Useful reagents having a reactive sulfone group that can be used in the methods include, without limitation, chlorosulfone, vinylsulfone and divinylsulfone.

In a specific embodiment, the water soluble polymer is activated with a Michael acceptor. WO 95/13312 describes, inter alia, water soluble sulfone-activated PEGs which are highly selective for coupling with thiol moieties instead of amino moieties on molecules and on surfaces. These PEG derivatives are stable against hydrolysis for extended periods in aqueous environments at pHs of about 11 or less, and can form linkages with molecules to form conjugates which are also hydrolytically stable. The linkage by which the PEGs and the biologically active molecule are coupled includes a sulfone moiety coupled to a thiol moiety and has the structure PEG-$SO_2$—$CH_2$—$CH_2$—S-W, where W represents the biologically active molecule, and wherein the sulfone moiety is vinyl sulfone or an active ethyl sulfone. Two particularly useful homobifunctional derivatives are PEG-bis-chlorosulfone and PEG-bis-vinylsulfone.

PCT International Application No. US96/19459, the disclosure of which is hereby incorporated by reference, teaches methods of making sulfone-activated linkers by obtaining a compound having a reactive hydroxyl group and converting the hydroxyl group to a reactive Michael acceptor to form an activated linker, with the use of tetrahydrofuran (THF) as the solvent for the conversion. PCT International Application No. US96/19459, the disclosure of which is hereby incorporated by reference, teaches a process for purifying the activated linkers which utilizes hydrophobic interaction chromatography to separate the linkers based on size and end-group functionality.

Specifically, the present invention contemplates the following prokaryote-expressed molecules chemically derivatized to include mono- or poly- (e.g., 2–4) PEG moieties: sTNFR-I 2.6D/C105, sTNFR-I 2.6D/C106, sTNFR-I 2.6D/N105, sTNFR-I 2.3D/d8, sTNFR-I 2.3D/d18 and sTNFR-I 2.3D/d15, either methionylated or nonmethionylated, and variants and derivatives thereof.

Polyvalent Form(s)

Polyvalent form(s), i.e., molecules comprising more than one active moiety, may be constructed. In one embodiment, the molecule may possess multiple tumor necrosis factor binding sites for the TNF ligand (e.g., a combination of a truncated sTNFR product). Additionally, the molecule may possess at least one tumor necrosis factor binding site and, depending upon the desired characteristic of polyvalent form, at least one binding site of another molecule (e.g., a combination of at least one truncated sTNFR product and at least one interleukin-1 receptor antagonist ("IL-1ra"), as described below).

In one embodiment, the polyvalent form may be constructed, for example, by chemically coupling at least one truncated sTNFR product and another moiety, preferably another truncated sTNFR product, with any clinically acceptable linker (e.g., water-soluble polymer, as described above). In principle the linker should not impart new immunogenicity nor, by virtue of the new amino acid residues, alter the hydrophobicity and charge balance of the structure to deleteriously affect its biodistribution and clearance.

Such polymers when used as linkers can be homopolymers, random or block copolymers and terpolymers based on the monomers listed above, straight chain or branched, substituted or unsubstituted. The polymer can be of any length or molecular weight, but these characteristics can affect the biological properties. Polymer average molecular weights particularly useful for decreasing clearance rates in pharmaceutical applications are in the range of 2,000 to 35,000 daltons. In addition, the length of the polymer can be varied to optimize or confer the desired biological activity.

Activating groups which can be used to link the water soluble polymer to two or more proteins include the following: sulfone, maleimide, sulfhydryl, thiol, triflate, tresylate, azidirine, oxirane and 5-pyridyl.

In a specific embodiment, a bifunctional or multifunctional activated linker having at least one reactive Michael acceptor may be prepared in accordance with U.S. patent application Ser. No. 08/473,809 and purified in accordance with U.S. patent application Ser. No. 08/611,918.

The active moieties may be linked using conventional coupling techniques (see PCT Publication No. WO 92/16221 and PCT Publication No. WO 95/34326, the disclosures of which are hereby incorporated by reference). Furthermore, PCT Publication No. WO 92/16221 describes the preparation of various dimerized sTNFR-I inhibitor molecules, e.g., dimerized c105 sTNFR-I. An exemplary polyvalent tumor necrosis factor binding proteins having the formula (sTNFR-I 2.6D/C106)$_2$-(20 kDa PEG), is disclosed in Example I.

Alternatively, a bivalent molecule may consist of two tandem repeats of truncated sTNFR products separated by a polypeptide linker region. The design of the polypeptide linkers is similar in design to the insertion of short loop sequences between domains in the de novo design of proteins (Mutter (1988), *TIBS,* 13:260–265 and Regan and DeGrado (1988), *Science,* 241:976–978, the disclosures of which are hereby incorporated by reference). It has been shown that a linker suitable for single chain antibodies is effective to produce a dimeric form of the recombinant human sTNFR-II (Neve et al. (1996), *Cytokine,* 8(5):365–370, the disclosure of which is hereby incorporated by reference). Several different linker constructs have been assembled and shown to be useful for antibodies; the most functional linkers vary in size from 12 to 25 amino acids (amino acids having unreactive side groups, e.g., alanine, serine and glycine) which together constitute a hydrophilic sequence, have a few oppositely charged residues to enhance solubility and are flexible (Whitlow and Filpula (1991), *Methods: A Companion to Methods in Enzymology,* 2:97–105 and Brigido et al. (1993), *J. Immunol.,* 150:469–479, the disclosures of which are hereby incorporated by reference).

In another embodiment, truncated sTNFRs may be chemically coupled to biotin, and the biotin/truncated sTNFRs which are conjugated are then allowed to bind to avidin, resulting in tetravalent avidin/biotin/truncated sTNFR molecules. Truncated sTNFRs may also be covalently coupled to dinitrophenol (DNP) or trinitrophenol (TNP) and the resulting conjugates precipitated with anti-DNP or anti-TNP-IgM to form decameric conjugates with a valency of 10 for TNF binding sites.

In yet another embodiment, recombinant fusion proteins may also be produced having a truncated sTNFR wherein each recombinant chimeric molecule has a sTNFR sequence, as described above, substituted for the variable domains of either or both of the immunoglobulin molecule heavy and light chains and having all or parts of the constant domains, but at least one constant domain, of the heavy or light chain of human immunoglobulin. For example, each such chimeric truncated sTNFR/IgG1 fusion protein may be produced from two chimeric genes: a truncated sTNFR/human kappa light chain chimera (truncated sTNFR/Ck) and a truncated sTNFR/human gamma-1 heavy chain chimera (truncated sTNFR/Cg-1). Following transcription and translation of the two chimeric genes, as described below, the gene products may be assembled into a single chimeric molecule having a truncated sTNFR displayed bivalently. Additional details relating to the construction of such chimeric molecules are disclosed in U.S. Pat. No. 5,116,964, PCT Publication No. WO 89/09622, PCT Publication No. WO 91/16437 and EP 315062, the disclosures of which are hereby incorporated by reference.

In yet a still further embodiment, recombinant fusion proteins may also be produced having a truncated sTNFR wherein each recombinant chimeric molecule has a sTNFR sequence, as described above, and at least a portion of the region 186–401 of osteoprotegerin (OPG), as described in European Patent Application No. 96309363.8.

Polynucleotides

The present invention further provides polynucleotides which encode truncated sTNFRs. Based upon the present description and using the universal codon table, one of ordinary skill in the art can readily determine all of the nucleic acid sequences which encode the amino acid sequences of truncated sTNFRs. Presently preferred nucleic acid sequences include those polynucleotides encoding sTNFR-I 2.6D/C105, sTNFR-I 2.6D/C106, sTNFR-I 2.6D/N105, sTNFR-I 2.3D/d8, sTNFR-I 2.3D/d18 and sTNFR-I 2.3D/d15. Examples of a variety of polynucleotides are depicted in FIGS. 2, 3, 4, 5, 6 and 7.

Recombinant expression techniques conducted in accordance with the descriptions set forth below may be followed to produce these polynucleotides and to express the encoded proteins. For example, by inserting a nucleic acid sequence which encodes a truncated sTNFR into an appropriate vector, one skilled in the art can readily produce large quantities of the desired nucleotide sequence. The sequences can then be used to generate detection probes or amplification primers. Alternatively, a polynucleotide encoding a truncated sTNFR can be inserted into an expression vector. By introducing the expression vector into an appropriate host, the desired truncated sTNFR may be produced in large amounts.

As further described herein, there are numerous host/vector systems available for the propagation of desired nucleic acid sequences and/or the production of truncated sTNFRs. These include but are not limited to plasmid, viral and insertional vectors, and prokaryotic and eukaryotic hosts. One skilled in the art can adapt a host/vector system which is capable of propagating or expressing heterologous DNA to produce or express the sequences of the present invention.

Furthermore, it will be appreciated by those skilled in the art that, in view of the present disclosure, the novel nucleic acid sequences include degenerate nucleic acid sequences encoding truncated sTNFRs having the sequences set forth in the Figures, and those nucleic acid sequences which hybridize (preferably under stringent hybridization conditions) to complements of these nucleic acid sequences (Maniatis et al. (1982), *Molecular Cloning* (A Laboratory Manual), Cold Spring Harbor Laboratory, pages 387 to 389). Exemplary stringent hybridization conditions are hybridization in 4×SSC at 62–67° C., followed by washing in 0.1×SSC at 62–67° C. for approximately an hour. Alternatively, exemplary stringent hybridization conditions are hybridization in 45–55% formamide, 4×SSC at 40–45° C. Also included are DNA sequences which hybridize to the nucleic acid sequences set forth in FIGS. 1 and 9 under relaxed hybridization conditions and which encode truncated sTNFRs. Examples of such relaxed stringency hybridization conditions are 4×SSC at 45–55° C. or hybridization with 30–40% formamide at 40–45° C.

Also provided by the present invention are recombinant DNA constructs involving vector DNA together with the DNA sequences encoding truncated sTNFRs. In each such DNA construct, the nucleic acid sequence encoding a truncated sTNFR (with or without signal peptides) is in operative association with a suitable expression control or regulatory sequence capable of directing the replication and/or expression of the truncated sTNFR in a selected host.

Recombinant Expression

Preparation of Polynucleotides

Nucleic acid sequences encoding truncated sTNFRs can readily be obtained in a variety of ways including, without limitation, chemical synthesis, cDNA or genomic library screening, expression library screening and/or PCR amplification of cDNA. These methods and others which are useful for isolating such nucleic acid sequences are set forth in Sambrook et al., *Molecular Cloning: A Laboratory Manual,* Cold Spring Harbor Laboratory Press, Cold Spring Harbor, N.Y., (1989); by Ausubel et al., eds *Current Protocols in Molecular Biology,* Current Protocols Press, (1994); and by Berger and Kimmel, *Methods in Enzymology: Guide* to *Molecular Cloning Techniques*, Vol. 152, Academic Press, Inc., San Diego, Calif., (1987), the disclosures of which are hereby incorporated by reference.

Chemical synthesis of nucleic acid sequences which encode truncated sTNFRs can be accomplished using methods well known in the art, such as those set forth by Engels et al. (1989), *Angew. Chem. Intl. Ed.,* 28:716–734 and Wells et al. (1985), *Gene,* 34:315, the disclosures of which are hereby incorporated by reference. These methods include, inter alia, the phosphotriester, phosphoramidite and H-phosphonate methods of nucleic acid sequence synthesis. Large nucleic acid sequences, for example those larger than about 100 nucleotides in length, can be synthesized as several fragments. The fragments can then be ligated together to form nucleic acid sequences encoding truncated sTNFRs. A preferred method is polymer-supported synthesis using standard phosphoramidite chemistry.

Alternatively, a suitable nucleic acid sequence may be obtained by screening an appropriate cDNA library (i.e., a library prepared from one or more tissue source believed to express the protein) or a genomic library (a library prepared from total genomic DNA). The source of the cDNA library is typically a tissue from any species that is believed to express a desired protein in reasonable quantities. The source of the genomic library may be any tissue or tissues from any mammalian or other species believed to harbor a gene encoding a truncated sTNFR.

Hybridization mediums can be screened for the presence of a DNA encoding a truncated sTNFR using one or more nucleic acid probes (oligonucleotides, cDNA or genomic DNA fragments that possess an acceptable level of homology to the cDNA or gene to be cloned) that will hybridize selectively with cDNA(s) or gene(s) present in the library. The probes typically used for such screening encode a small region of DNA sequence from the same or a similar species as the species from which the library is prepared. Alternatively, the probes may be degenerate, as discussed herein.

Hybridization is typically accomplished by annealing the oligonucleotide probe or cDNA to the clones under conditions of stringency that prevent non-specific binding but permit binding of those clones that have a significant level of homology with the probe or primer. Typical hybridization and washing stringency conditions depend in part on the size (i.e., number of nucleotides in length) of the cDNA or oligonucleotide probe and whether the probe is degenerate. The probability of identifying a clone is also considered in designing the hybridization medium (e.g., whether a cDNA or genomic library is being screened).

Where a DNA fragment (such as cDNA) is used as a probe, typical hybridization conditions include those as set forth in Ausubel et al. (1994), eds., supra. After hybridization, the hybridization medium is washed at a suitable stringency depending on several factors such as probe size, expected homology of probe to clone, the hybridization medium being screened, the number of clones being screened and the like. Examples of stringent washing solutions, which are usually low in ionic strength and are used at relatively high temperatures, are as follows: one such stringent wash is 0.015 M NaCl, 0.005 M NaCitrate and 0.1% SDS at 55–65° C.; another such stringent wash is 1 mM $Na_2EDTA$, 40 mM $NaHPO_4$, pH 7.2, and 1% SDS at about 40–50° C.; and one other stringent wash is 0.2×SSC and 0.1% SDS at about 50–65° C.

There are also exemplary protocols for stringent washing conditions where oligonucleotide probes are used to screen hybridization mediums. For example, a first protocol uses 6×SSC with 0.05 percent sodium pyrophosphate at a temperature of between about 35° C. and 63° C., depending on the length of the probe. For example, 14 base probes are washed at 35–40° C., 17 base probes at 45–50° C., 20 base probes at 52–57° C., and 23 base probes at 57–63° C. The temperature can be increased 2–3° C. where the background non-specific binding appears high. A second protocol uses tetramethylammonium chloride (TMAC) for washing. One such stringent washing solution is 3 M TMAC, 50 mM Tris-HCl, pH 8.0 and 0.2% SDS.

Another suitable method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA (oligonucleotides) encoding a truncated sTNFR, are then added to the cDNA along with a polymerase such as Taq polymerase, and the polymerase amplifies the cDNA region between the two primers.

The oligonucleotide sequences selected as probes or primers should be of adequate length and sufficiently unambiguous so as to minimize the amount of non-specific binding that may occur during screening or PCR amplification. The actual sequence of the probes or primers is usually based on conserved or highly homologous sequences or regions. Optionally, the probes or primers can be fully or partially degenerate, i.e., can contain a mixture of probes/primers, all encoding the same amino acid sequence but using different codons to do so. An alternative to preparing degenerate probes is to place an inosine in some or all of those codon positions that vary by species. The oligonucleotide probes or primers may be prepared by chemical synthesis methods for DNA, as described above.

As described above, a variant sequence is a natural (e.g., an allelic variation) or synthetic sequence that contains one or more nucleotide substitutions, deletions, and/or insertions as compared to the sequence of FIGS. 2, 3, 4, 5, 6 and 7 and that results in the expression of amino acid sequence variations as compared to the wild type amino acid sequence. Preparation of synthetic variant sequences is also well known in the art, and is described, for example, in Sambrook et al. (1989), supra and Wells et al. (1985), *Gene,* 34:315, the disclosure of which is hereby incorporated by reference.

Vectors

DNA encoding truncated sTNFRs may be inserted into vectors for further cloning (amplification of the DNA) or for expression. Suitable vectors are commercially available, or the vector may be specifically constructed. The selection or construction of an appropriate vector will depend on (1) whether it is to be used for DNA amplification or for DNA expression, (2) the size of the DNA to be inserted into the vector, and (3) the intended host cell to be transformed with the vector.

The vectors each involve a nucleic acid sequence which encodes a desired protein operatively linked to one or more of the following expression control or regulatory sequences capable of directing, controlling or otherwise effecting the expression of a desired protein by a selected host cell. Each vector contains various components, depending on its function (amplification of DNA or expression of DNA) and its compatibility with the intended host cell. The vector components generally include but are not limited to one or more of the following: a signal sequence, an origin of replication, one or more selection or marker genes, promoters, enhancer elements, a transcription termination sequence and the like. These components may be obtained from natural sources or be synthesized by known procedures.

Examples of suitable prokaryotic cloning vectors include bacteriophages such as lambda derivatives, or plasmids from *E. coli* (e.g. pBR322, col E1, pUC, the F-factor and Bluescript® plasmid derivatives (Stratagene, LaJolla, Calif.)). Other appropriate expression vectors, of which numerous types are known in the art for the host cells described below, can also be used for this purpose.

Signal Sequence

The nucleic acid encoding a signal sequence may be inserted 5' of the sequence encoding a truncated sTNFR, e.g., it may be a component of a vector, or it may be a part of a nucleic acid encoding a truncated sTNFR. The nucleic acid encoding the native signal sequences of sTNFR-I and sTNFR-II are known (EP 393 438 and EP 422 339).

Origin of Replication

Expression and cloning vectors each generally include a nucleic acid sequence that enables the vector to replicate in one or more selected host cells. In a cloning vector, this sequence is typically one that enables the vector to replicate independently of the host chromosomal DNA, and includes origins of replication or autonomously replicating sequences. Such sequences are well known. The origin of replication from the plasmid pBR322 is suitable for most Gram-negative bacteria, and various origins (e.g., SV40, polyoma, adenovirus, VSV or BPV) are useful for cloning vectors in mammalian cells. Generally, the origin of replication is not needed for mammalian expression vectors (for example, the SV40 origin is often used only because it contains the early promoter).

Selection Gene

The expression and cloning vectors each typically contain a selection gene. This gene encodes a "marker" protein necessary for the survival or growth of the transformed host cells when grown in a selective culture medium. Host cells that are not transformed with the vector will not contain the selection gene and, therefore, they will not survive in the culture medium. Typical selection genes encode proteins that (a) confer resistance to antibiotics or other toxins, e.g., ampicillin, neomycin, methotrexate or tetracycline; (b) complement auxotrophic deficiencies or (c) supply critical nutrients not available from the culture medium.

Other selection genes may be used to amplify the genes to be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The cell transformants are placed under selection pressure which only the transformants are uniquely adapted to survive by virtue of the markers present in the vector. Selection pressure is imposed by culturing the transformed cells under conditions in which the concentration of selection agent in the medium is successively changed, thereby leading to amplification of both the selection genes and the DNA that encodes truncated sTNFRs. As a result, increased quantities of truncated sTNFRs are synthesized from the amplified DNA.

For example, cells transformed with the DHFR selection gene are first identified by culturing all of the transformants in a culture medium that contains methotrexate, a competitive antagonist of DHFR. An appropriate host cell when wild-type DHFR is used is the Chinese hamster ovary cell line deficient in DHFR activity (Urlaub and Chasin (1980), *Proc. Natl. Acad. Sci., USA*, 77(7):4216–4220, the disclosure of which is hereby incorporated by reference). The transformed cells are then exposed to increased levels of methotrexate. This leads to the synthesis of multiple copies of the DHFR gene and, concomitantly, multiple copies of other DNA present in the expression vector, such as the DNA encoding a truncated sTNFR.

Promoter

Expression and cloning vectors each will typically contain a promoter that is recognized by the host organism and is operably linked to a nucleic acid sequence encoding a truncated sTNFR. A promoter is an untranslated sequence located upstream (5') to the start codon of a structural gene (generally within about 100 to 1000 bp) that controls the transcription and translation of a particular nucleic acid sequence, such as that encoding a truncated sTNFR. A promoter may be conventionally grouped into one of two classes, inducible promoters and constitutive promoters. An inducible promoter initiates increased levels of transcription from DNA under its control in response to some change in culture conditions, such as the presence or absence of a nutrient or a change in temperature. A large number of promoters, recognized by a variety of potential host cells, are well known. A promoter may be operably linked to DNA encoding a truncated sTNFR by removing the promoter from the source DNA by restriction enzyme digestion and inserting the desired promoter sequence. The native sTNFR-I promoter sequence or sTNFR-II promoter sequence may be used to direct amplification and/or expression of DNA encoding a truncated sTNFR. A heterologous promoter is preferred, however, if it permits greater transcription and higher yields of the expressed protein as compared to the native promoter and if it is compatible with the host cell system that has been selected for use. For example, any one of the native promoter sequences of other NGF/TNF family members may be used to direct amplification and/or expression of the DNA encoding a truncated sTNFR.

Promoters suitable for use with prokaryotic hosts include the beta-lactamase and lactose promoter systems; alkaline phosphatase, a tryptophan (trp) promoter system; a bacterial luminescence (luxR) gene system and hybrid promoters such as the tac promoter. Other known bacterial promoters are also suitable. Their nucleotide sequences have been published, thereby enabling one skilled in the art to ligate them to the desired DNA sequence(s) using linkers or adaptors as needed to supply any required restriction sites.

Suitable promoting sequences for use with yeast hosts are also well known in the art. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and, most preferably, Simian Virus 40 (SV40). Other suitable mammalian promoters include heterologous mammalian promoters, e.g., heat-shock promoters and the actin promoter.

Enhancer Element

The expression and cloning vectors each will typically contain an enhancer sequence to increase the transcription by higher eukaryotes of a DNA sequence encoding a truncated sTNFR. Enhancers are cis-acting elements of DNA, usually from about 10–300 bp in length, that act on the promoter to increase its transcription. Enhancers are relatively orientation and position independent. They have been found 5' and 3' to the transcription unit. Yeast enhancers are advantageously used with yeast promoters. Several enhancer sequences available from mammalian genes are known (e.g., globin, elastase, albumin, alpha-feto-protein and insulin).

Additionally, viral enhancers such as the SV40 enhancer, the cytomegalovirus early promoter enhancer, the polyoma enhancer and adenovirus enhancers are exemplary enhancing elements for the activation of eukaryotic promoters. While an enhancer may be spliced into a vector at a position 5' or 3' to a DNA encoding truncated sTNFR, it is typically located at a site 5' from the promoter.

Transcription Termination

Expression vectors used in eukaryotic host cells each will typically contain a sequence necessary for the termination of transcription and for stabilizing the mRNA. Such sequences are commonly available from the 5' and occasionally 3' untranslated regions of eukaryotic DNAs or cDNAs. These regions contain nucleotide segments transcribed as polyadenylated fragments in the untranslated portion of the mRNA encoding a truncated sTNFR.

Vector Construction

The construction of a suitable vector containing one or more of the above-listed components (together with the coding sequence encoding a truncated sTNFR) is accomplished by standard ligation techniques. Isolated plasmids or DNA fragments are cleaved, tailored and religated in the desired order to generate the vector required. To confirm that the correct sequence has been constructed, the ligation mixture may be used to transform E. coli, and successful transformants may be selected by known techniques as described above. Quantities of the vector from the transformants are then prepared, analyzed by restriction endonuclease digestion and/or sequenced to confirm the presence of the desired construct.

A vector that provides for the transient expression of DNA encoding a truncated sTNFR in mammalian cells may also be used. In general, transient expression involves the use of an expression vector that is able to replicate efficiently in a host cell, such that the host cell accumulates many copies of the expression vector and, in turn, synthesizes high levels of the desired protein encoded by the expression vector. Each transient expression system, comprising a suitable expression vector and a host cell, allows for the convenient positive identification of proteins encoded by cloned DNAs, as well as for the rapid screening of such proteins for desired biological or physiological properties, i.e., identifying a biologically-active truncated sTNFR.

Host Cells

Any of a variety of recombinant host cells, each of which contains a nucleic acid sequence for use in expressing a desired protein, is also provided by the present invention. Exemplary prokaryotic and eukaryotic host cells include bacterial, mammalian, fungal, insect, yeast or plant cells.

Prokaryotic host cells include but are not limited to eubacteria such as Gram-negative or Gram-positive organisms (e.g., *E. coli* (HB101, DH5a, DH10 and MC1061); *Bacilli* such as *B. subtilis; Pseudomonas* species, such as *P. aeruginosa; Streptomyces* spp.; *Salmonella typhimurium*; or *Serratia marcescans*. As a specific embodiment, a desired protein may be expressed in *E. coli.*

In addition to prokaryotic host cells, eukaryotic microbes such as filamentous fungi or yeast may be suitable hosts for the expression of truncated sTNFRs. *Saccharomyces cerevisiae*, or common baker's yeast, is the most commonly used among lower eukaryotic host microorganisms, but a number of other genera, species and strains are well known and commonly available.

A truncated sTNFR may be expressed in glycosylated form by any one of a number of suitable host cells derived from multicellular organisms. Such host cells are capable of complex processing and glycosylation activities. In principle, any higher eukaryotic cell culture might be used, whether such culture involves vertebrate or invertebrate cells, including plant and insect cells. As a specific embodiment, a desired protein may be expressed in baculovirus cells.

Vertebrate cells may be used, as the propagation of vertebrate cells in culture (tissue culture) is a well-known procedure. Examples of useful mammalian host cell lines include but are not limited to monkey kidney CV1 line transformed by SV40 (COS-7), human embryonic kidney line (293 cells or 293 cells subcloned for growth in suspension culture), baby hamster kidney cells and Chinese hamster ovary cells. Other suitable mammalian cell lines include but are not limited to HeLa, mouse L-929 cells, 3T3 lines derived from Swiss, Balb-c or NIH mice, and BHK or HaK hamster cell lines. As a specific embodiment, a desired protein may be expressed in COS cells.

A host cell may be transfected and preferably transformed with a desired nucleic acid under appropriate conditions permitting expression of the nucleic acid. The selection of suitable host cells and methods for transformation, culture, amplification, screening and product production and purification are well known in the art (Gething and Sambrook (1981), *Nature,* 293:620–625 or, alternatively, Kaufman et al. (1985), *Mol. Cell. Biol.,* 5(7):1750–1759, or U.S. Pat. No. 4,419,446, the disclosures of which are hereby incorporated by reference). For example, for mammalian cells without cell walls, the calcium phosphate precipitation method may be used. Electroporation, micro injection and other known techniques may also be used.

It is also possible that truncated sTNFRs may be produced by homologous recombination or with recombinant production methods utilizing control elements introduced into cells already containing DNA encoding truncated sTNFRs. Homologous recombination is a technique originally developed for targeting genes to induce or correct mutations in transcriptionally-active genes (Kucherlapati (1989), *Prog. in Nucl. Acid Res. and Mol. Biol.,* 36:301, the disclosure of which is hereby incorporated by reference). The basic technique was developed as a method for introducing specific mutations into specific regions of the mammalian genome (Thomas et al. (1986), *Cell,* 44:419–428; Thomas and Capecchi (1987), *Cell,* 51:503–512 and Doetschman et al. (1988), *Proc. Natl. Acad. Sci.,* 85:8583–8587, the disclosures of which are hereby incorporated by reference) or to correct specific mutations within defective genes (Doetschman et al. (1987), *Nature,* 330:576–578, the disclosure of which is hereby incorporated by reference). Exemplary techniques are described in U.S. Pat. No. 5,272,071; WO 92/01069; WO 93/03183; WO 94/12650 and WO 94/31560, the disclosures of which are hereby incorporated by reference.

Through homologous recombination, the DNA sequence to be inserted into the genome can be directed to a specific region of the gene of interest by attaching it to targeting DNA. The targeting DNA is DNA that is complementary (homologous) to a region of the genomic DNA. Small pieces of targeting DNA that are complementary to a specific region of the genome are put in contact with the parental strand during the DNA replication process. A general property of DNA that has been inserted into a cell is to hybridize and therefore recombine with other pieces of endogenous DNA through shared homologous regions. If this complementary strand is attached to an oligonucleotide that contains a mutation or a different sequence of DNA, it too is incorporated into the newly synthesized strand as a result of the recombination. As a result of the proofreading function, it is possible for the new sequence of DNA to serve as the template. Thus, the transferred DNA is incorporated into the genome.

If the sequence of a particular gene is known, such as the nucleic acid sequence of a truncated sTNFR, the expression control sequence (a piece of DNA that is complementary to a selected region of the gene) can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA.

Attached to these pieces of targeting DNA are regions of DNA which may interact with the expression of a truncated sTNFR. For example, a promoter/enhancer element, a suppresser or an exogenous transcription modulatory element is inserted into the genome of the intended host cell in proximity and orientation sufficient to influence the transcription of DNA encoding the desired truncated sTNFR. The control element does not encode the truncated sTNFR, but instead controls a portion of the DNA present in the host cell genome. Thus, the expression of a truncated sTNFR may be achieved not by transfection of DNA that encodes a truncated sTNFR, but rather by the use of targeting DNA (containing regions of homology with the endogenous gene of interest) coupled with DNA regulatory segments that provide the endogenous gene sequence with recognizable signals for transcription of a truncated sTNFR.

Culturing the Host Cells

The method for culturing each of the one or more recombinant host cells for production of a desired protein will vary depending upon many factors and considerations; the optimum production procedure for a given situation will be apparent to those skilled in the art through minimal experimentation. Such recombinant host cells are cultured in suitable medium and the expressed truncated sTNFR is then optionally recovered, isolated and purified from the culture medium (or from the cell, if expressed intracellularly) by appropriate means known to those skilled in the art.

Specifically, each of the recombinant cells used to produce a desired truncated sTNFR may be cultured in media suitable for inducing promoters, selecting suitable recombinant host cells or amplifying the gene encoding the desired truncated sTNFR. The media may be supplemented as necessary with hormones and/or other growth factors (such as insulin, transferrin or epidermal growth factor), salts (such as sodium chloride, calcium, magnesium and phosphate), buffers (such as HEPES), nucleosides (such as adenosine and thymidine), antibiotics (such as gentamicin), trace elements (defined as inorganic compounds usually present at final concentrations in the micromolar range), and glucose or another energy source. Other supplements may also be included, at appropriate concentrations, as will be appreciated by those skilled in the art. Suitable culture conditions, such as temperature, pH and the like, are also well known to those skilled in the art for use with the selected host cells.

The resulting expression product may then be purified to near homogeneity using procedures known in the art. Exemplary purification techniques are taught in EP 393 438 and EP 422 339, the disclosures of which are incorporated herein by reference.

Pharmaceutical Compositions

Pharmaceutical compositions each will generally include a therapeutically effective amount of truncated sTNFRs and chemically-modified derivatives of truncated sTNFRs (collectively, "truncated sTNFR product(s)") in admixture with a vehicle. The vehicle preferably includes one or more pharmaceutically and physiologically acceptable formulation materials in admixture with the truncated sTNFR product(s) and controlled release material.

The primary solvent in a vehicle may be either aqueous or non-aqueous in nature. In addition, the vehicle may contain other pharmaceutically acceptable excipients for modifying or maintaining the pH preferably between 5–6.5, and more preferably between 5.5–6.0 (e.g., buffers such as citrates, phosphates and amino acids such glycine); bulking agents for lyophilized formulation (e.g., mannitol and glycine); osmolarity (e.g., mannitol and sodium chloride); surfactants (e.g., polysorbate 20, polysorbate 80, triton, and pluronics); viscosity; clarity; color; sterility; stability (e.g., sucrose and sorbitol); antioxidants (e.g., sodium sulfite and sodium hydrogen-sulfite); preservatives (e.g., benzoic acid and salicylic acid); odor of the formulation; flavoring and diluting agents; rate of dissolution (e.g., solubilizers or solubilizing agents such as alcohols, polyethylene glycols and sodium chloride); rate of release; emulsifying agents; suspending agents; solvents; fillers; delivery vehicles; diluents; excipients and/or pharmaceutical adjuvants. Other effective administration forms such as parenteral slow-release formulations, inhalant mists, orally-active formulations, or suppositories are also envisioned. The composition may also involve particulate preparations of polymeric compounds such as bulk erosion polymers (e.g., poly(lactic-co-glycolic acid) (PLGA) copolymers, PLGA polymer blends, block copolymers of PEG, and lactic and glycolic acid, poly (cyanoacrylates)); surface erosion polymers (e.g., poly (anhydrides) and poly(ortho esters)); hydrogel esters (e.g., pluronic polyols, poly(vinyl alcohol), poly (vinylpyrrolidone), maleic anhydride-alkyl vinyl ether copolymers, cellulose, hyaluronic acid derivatives, alginate, collagen, gelatin, albumin, and starches and dextrans) and composition systems thereof; or preparations of liposomes or microspheres. Such compositions may influence the physical state, stability, rate of in vivo release, and rate of in vivo clearance of the present proteins and derivatives. The optimal pharmaceutical formulation for a desired protein will be determined by one skilled in the art depending upon the route of administration and desired dosage. Exemplary pharmaceutical compositions are disclosed in *Remington's Pharmaceutical Sciences,* 18th Ed. (1990), Mack Publishing Co., Easton, Pa. 18042, pages 1435–1712; Gombotz and Pettit (1995), *Bioconjugate Chem.,* 6:332–351; Leone-Bay, et al. (1995), *Journal of Medicinal Chemistry,* 38:4263–4269; Haas, et al. (1995), *Clinical Immunology and Immunopathology,* 76(1):93; WO 94/06457; WO 94/21275; FR 2706772 and WO 94/21235, the disclosures of which are incorporated herein by reference.

Specific sustained release compositions are available from the following suppliers: Depotech (Depofoam™, a multivesicular liposome); Alkermes (ProLease™, a PLGA microsphere). As used herein, hyaluronan is intended to include hyaluronan, hyaluronic acid, salts thereof (such as sodium hyaluronate), esters, ethers, enzymatic derivatives and cross-linked gels of hyaluronic acid, and chemically modified derivatives of hyaluronic acid (such as hylan). Exemplary forms of hyaluronan are disclosed in Peyron and Balazs (1974), *Path. Biol.,* 22(8):731–736; Isdale et al. (1991), *J. Drug Dev.,* 4 (2) :93–99; Larsen et al. (1993), Journal of Biomedical Materials Research, 27:1129–1134; Namiki, et al. (1982), International Journal of Clinical Pharmacology, Therapy and Toxicology, 20(11):501–507; Meyer et al. (1995), Journal of Controlled Release, 35:67–72; Kikuchi et al. (1996), Osteoarthritis and Cartilage, 4:99–110; Sakakibara et al. (1994), Clinical Orthopaedics and Related Research, 299:282–292; Meyers and Brandt (1995), 22(9):1732–1739; Laurent et al. (1995), Acta Orthop Scand, 66(266):116–120; Cascone et al. (1995), Biomaterials, 16(7):569–574; Yerashalmi et al. (1994), Archives of Biochemistry and Biophysics, 313(2):267–273; Bernatchez et al. (1993), Journal of Biomedical Materials Research, 27(5):677–681; Tan et al. (1990), Australian Journal of Biotechnology, 4(1):38–43; Gombotz and Pettit (1995), Bioconjugate Chem., 6:332–351; U.S. Pat. Nos. 4,582,865, 4,605,691, 4,636,524, 4,713,448, 4,716,154, 4,716,224, 4,772,419, 4,851,521, 4,957,774, 4,863,907, 5,128,326, 5,202,431, 5,336,767, 5,356,883; European Patent Application Nos. 0 507 604 A2 and 0 718 312 A2; and WO 96/05845, the disclosures of which are hereby incorporated by reference. Specific hyaluronan compositions are available from the following suppliers: BioMatrix, Inc. Ridgefield, N.J. (Synvisc™, a 90:10 mixture of a hylan fluid and hylan gel); Fidia S.p.A., Abano Terme, Italy (Hyalgan™, the sodium salt of a rooster comb-derived hyaluronic acid (~500,000 to ~700,000 MW)); Kaken Pharmaceutical Co., Ltd., Tokyo, Japan (Art z™, a 1% solution of a rooster-comb derived hyaluronic acid, ~700,000 MW); Pharmacia AB, Stockholm, Sweden (Healon™, a rooster-comb derived hyaluronic acid, ~4×10$^6$ MW); Genzyme Corporation, Cambridge, Mass. (Surgicoat™, a recombinant hyaluronic acid); Pronova Biopolymer, Inc. Portsmouth, N.H. (Hyaluronic Acid FCH, a high molecular weight (e.g., ~1.5–2.2×10$^6$ MW) hyaluronic acid prepared from cultures of Streptococcus zooepidemicus; Sodium Hyaluronate MV, ~1.0–1.6×10$^6$ MW and Sodium Hyaluronate LV, ~1.5–2.2× 10$^6$ MW); Calbiochem-Novabiochem AB, Lautelfingen, Switzerland (Hyaluronic Acid, sodium salt (1997 company catalog number 385908) prepared from Streptococcus sp.); Intergen Company, Purchase, N.Y. (a rooster-comb derived hyaluronic acid, >1×10$^6$ MW); Diosynth Inc., Chicago, Ill.; Amerchol Corp., Edison, N.J. and Kyowa Hakko Kogyo Co., Ltd., Tokyo, Japan.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Kits included within the scope of this invention are single and multi-chambered pre-filled syringes; exemplary pre-filled syringes (e.g., liquid syringes, and lyosyringes such as Lyo-Ject®, a dual-chamber pre-filled lyosyringe) are available from Vetter GmbH, Ravensburg, Germany.

Uses

Truncated sTNFR products may be useful as research reagents and as therapeutic and diagnostic agents. Thus the truncated sTNFRs may be used in in vitro and/or in vivo diagnostic assays to quantify the amount of native sTNFR-I or sTNFR-II in a tissue or organ sample or to determine and/or isolate cells which express TNF (Scallon et al. (1995), supra). In assays of tissues or organs there will be less radioactivity from $^{125}$I-truncated sTNFRs binding to TNF, as compared to a standardized binding curve of $^{125}$I-truncated sTNFRs, due to unlabeled native sTNFR-I or sTNFR-I binding to TNF. Similarly, the use of $^{125}$I-truncated sTNFRs may be used to detect the presence of TNF in various cell types.

This invention also contemplates the use of truncated sTNFR products in the generation of antibodies and the resultant antibodies (specifically including those which also bind to native sTNFR-I or sTNFR-II). Antibodies can be developed which bind to truncated sTNFRs, such as to epitopes within the $R_1$-[$Cys^{19}$–$Cys^{103}$]-$R_2$ amino acid sequence or within the $R_4$-[$Cys^{32}$–$Cys^{115}$]-$R^5$ amino acid sequence. One of ordinary skill in the art can use well-known published procedures to obtain monoclonal and polyclonal antibodies, or recombinant antibodies, which specifically recognize and bind to the various proteins encoded by the amino acid sequences of the present invention. Such antibodies may then be used to purify and characterize the full-length, mature 30 kDa TNF inhibitor and full-length, mature 40 kDa TNF inhibitor.

The present invention also relates to methods for the treatment of certain diseases and medical conditions (many of which can be characterized as inflammatory diseases) that are mediated by TNF. A disease or medical condition is considered to be a "TNF-mediated disease" if the spontaneous or experimental disease is associated with elevated levels of TNF in bodily fluids or in tissues adjacent to the focus of the disease or indication within the body. TNF-mediated diseases may also be recognized by the following two conditions: (1) pathological findings associated with a disease can be mimicked experimentally in animals by the administration of TNF and (2) the pathology induced in experimental animal models of the disease can be inhibited or abolished by treatment with agents which inhibit the action of TNF. Many TNF-mediated diseases satisfy two of these three conditions, and others will satisfy all three conditions. A non-exclusive list of TNF-mediated diseases, as well as the related sequela and symptoms associated therewith, that each may be treated according to the methods of the present invention are adult respiratory distress syndrome; cachexia/anorexia; cancer (e.g., leukemias); chronic fatigue syndrome; graft versus host rejection; hyperalgesia; inflammatory bowel disease; neuroinflammatory diseases; ischemic/reperfusion injury, including cerebral ischemia (brain injury as a result of trauma, epilepsy, hemorrhage or stroke, each of which may lead to neurodegeneration); diabetes (e.g., juvenile onset Type 1 diabetes mellitus); multiple sclerosis; ocular diseases; pain; pancreatitis; pulmonary fibrosis; rheumatic diseases (e.g., rheumatoid arthritis, osteoarthritis, juvenile (rheumatoid) arthritis, seronegative polyarthritis, ankylosing spondylitis, Reiter's syndrome and reactive arthritis, psoriatic arthritis, enteropathic arthritis, polymyositis, dermatomyositis, scleroderma, systemic sclerosis, vasculitis, cerebral vasculitis, Sjögren's syndrome, rheumatic fever, polychondritis and polymyalgia rheumatica and giant cell arteritis); septic shock; side effects from radiation therapy; systemic lupus erythematous; temporal mandibular joint disease; thyroiditis and tissue transplantation.

The truncated sTNFR products each may be administered to a patient in therapeutically effective amounts for the treatment of TNF-mediated diseases, as defined above, including such as rheumatic diseases (e.g., lyme disease, juvenile (rheumatoid) arthritis, osteoarthritis, psoriatic arthritis, rheumatoid arthritis and staphylococcal-induced ("septic") arthritis). The term "patient" is intended to encompass animals (e.g., cats, dogs and horses) as well as humans.

A truncated sTNFR product may be administered via topical, enteral or parenteral administration including, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, intraventricular and intrasternal injection and infusion. A truncated sTNFR product may also be administered via oral administration or be administered through mucus membranes, that is, intranasally, sublingually, buccally or rectally for systemic delivery.

It is preferred that truncated sTNFR products be administered via intra-articular, subcutaneous, intramuscular or intravenous injection. Additionally, truncated sTNFR product may be administered by a continuous infusion (e.g., constant or intermittent implanted or external infusion flow-modulating devices) so as to continuously provide the desired level of truncated sTNFR product in the blood for the duration of the administration. This is preferably accomplished by means of continuous infusion via, e.g., mini-pump such as osmotic mini-pump. In these ways, one can be assured that the amount of drug is maintained at the desired level and one can take blood samples and monitor the amount of drug in the bloodstream. Various pumps are commercially available, from suppliers such as MiniMed Inc, Sylmar, Calif. (e.g., MT507) and Alza Corp., Palo Alto, Calif. (e.g., Alzet osmotic pump, model 2MLI).

It is also contemplated that other modes of continuous or near-continuous dosing may be practiced. For example, chemical derivatization may result in sustained release forms of the protein which have the effect of continuous presence in the blood stream, in predictable amounts based on a determined dosage regimen.

Modes of using the truncated sTNFR products for the treatment of TNF-mediated diseases, including inflammatory conditions of a joint (e.g., osteoarthritis, psoriatic arthritis and rheumatoid arthritis), are set forth in European Patent Application 567566, the teachings of which are hereby incorporated by reference. By way of example but not limitation, in one specific embodiment truncated sTNFR products may be administered intra-articularly for the treatment of rheumatoid arthritis and osteoarthritis. By way of example but not limitation in another specific embodiment, truncated sTNFR products may be administered subcutaneously or intramuscularly for the treatment of rheumatoid arthritis, inflammatory bowel disease, cachexia/anorexia or multiple sclerosis. By way of example but not limitation, in a still further specific embodiment truncated sTNFR products may be administered intravenously for the treatment of brain injury as a result of trauma, epilepsy, hemorrhage or stroke; or administered intraventricularly for the treatment of brain injury as a result of trauma. A preferred mode for the treatment of arthritis includes: (1) a single intra-articular injection of a truncated sTNFR product given periodically as needed to prevent or remedy the flare-up of arthritis and (2) periodic subcutaneous injections of a truncated sTNFR product. The initiation of treatment for septic shock should begin as soon as possible after septicemia or the chance of septicemia is diagnosed. For example, treatment may be begun immediately following surgery or an accident or any other event that may carry the risk of initiating septic shock. Preferred modes for the treatment of adult respiratory distress syndrome include: (1) single or multiple intratracheal administrations of a truncated sTNFR product and (2) bolus or continuous intravenous infusion of a truncated sTNFR product.

In another embodiment, cell therapy, e.g., implantation of cells producing a truncated sTNFR, is also contemplated. This embodiment of the present invention may include implanting into patients cells which are capable of synthesizing and secreting a biologically-active form of a truncated sTNFR. Such cells producing a truncated sTNFR may be cells which do not normally produce a truncated sTNFR but which have been modified to produce a truncated sTNFR, or which may be cells whose ability to produce a truncated sTNFR have been augmented by transformation with a polynucleotide suitable for the expression and secretion of a truncated sTNFR. In order to minimize a potential immunological reaction in patients by administering a truncated sTNFR of a foreign species, it is preferred that the cells be of the same species as the patient (e.g., human) or that the cells be encapsulated with material that provides a barrier against immune recognition, or that cells be placed into an immunologically privileged anatomical location, such as in the testis, eye or central nervous system.

Human or non-human animal cells may be implanted in patients in biocompatible, semi-permeable polymeric enclosures or membranes to allow release of a truncated sTNFR, but to prevent destruction of the cells by the patient's immune system or by other detrimental factors from the surrounding tissue. Alternatively, the patient's own cells, transformed ex vivo to produce a truncated sTNFR, may be implanted directly into the patient without such encapsulation. The methodology for the membrane encapsulation of living cells is familiar to those of ordinary skill in the art, and the preparation of the encapsulated cells and their implantation in patients may be accomplished.

In yet another embodiment, in vivo gene therapy is also envisioned, wherein a nucleic acid sequence encoding a truncated sTNFR is introduced directly into a patient. For example, a nucleic acid sequence encoding a truncated sTNFR is introduced into target cells via local injection of a nucleic acid construct, with or without an appropriate delivery vector, such as an adeno-associated virus vector. Alternative viral vectors include but are not limited to retrovirus, adenovirus, herpes simplex virus and papilloma virus vectors. Physical transfer may be achieved in vivo by local injection of the desired nucleic acid construct or other appropriate delivery vector containing the desired nucleic acid sequence, liposome-mediated transfer, direct injection (naked DNA), receptor-mediated transfer (ligand-DNA complex) or microparticle bombardment (gene gun).

Exemplary cell and gene therapy techniques are disclosed in U.S. Pat. No. 4,892,538; U.S. Pat. No. 5,011,472; U.S. Pat. No. 5,106,627; DE 4219626, WO 94/20517 and 96/22793, the disclosures of which are hereby incorporated by reference.

Regardless of the manner of administration, the treatment of a TNF-mediated disease requires a dose or total dose regimen of a truncated sTNFR effective to reduce or alleviate symptoms of the disease. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information ad assays disclosed herein. The dosage can also be determined through the use of known assays for determining dosages used in conjunction with appropriate dose-response data. The specific dose is calculated according to the approximate body weight or body surface area of the patient.

The frequency of dosing depends on the pharmacokinetic parameters of the truncated sTNFR in the formulation used.

The truncated sTNFR may be administered once, or in cases of severe and prolonged disorders, administered daily in less frequent doses or administered with an initial bolus dose followed by a continuous dose or sustained delivery. When administered parenterally, parenteral unit doses, for example, may each be up to 10 mg, generally up to 15 mg and more generally up to 20 mg. When administered into an articular cavity, the pharmaceutical composition is preferably administered as a single injection from, for example, a 3 to 10 ml syringe containing a dose, for example, of between about 5 mg/ml to 10 mg/ml truncated sTNFR dissolved in isotonic phosphate buffered saline. The preparation may be administered into an articular cavity at a frequency, for example, of once every 7 to 10 days. In such a manner, the administration is continuously conducted, for example, 4 to 5 times while varying the dose if necessary.

In some cases, truncated sTNFR products may be administered as an adjunct to other therapy and also with other pharmaceutical formulations suitable for the indication being treated. A truncated sTNFR product and any of one or more traditional or new anti-inflammatory drugs may be administered separately or in combination.

Truncated sTNFR products (e.g., $R_1$-[Cys$^{19}$–Cys$^{103}$]-$R_2$ proteins) and any of one or more additional anti-inflammatory drugs may be administered separately or in combination. Information regarding the following compounds can be found in The Merck Manual of Diagnosis and Therapy, Sixteenth Edition, Merck, Sharp & Dohme Research Laboratories, Merck & Co., Rahway, N.J. (1992) and in Pharmaprojects, PJB Publications Ltd.

Present treatment of TNF-mediated diseases, as defined above, including acute and chronic inflammation such as rheumatic diseases (e.g., lyme disease, juvenile (rheumatoid) arthritis, osteoarthritis, psoriatic arthritis, rheumatoid arthritis and staphylococcal-induced ("septic") arthritis) includes first line drugs for control of pain and inflammation classified as non-steroidal, anti-inflammatory drugs (NSAIDs). Secondary treatments include corticosteroids, slow acting antirheumatic drugs (SAARDs) or disease modifying (DM) drugs.

In a specific embodiment, the present invention is directed to the use of a truncated sTNFR product (e.g., $R_1$-[Cys$^{19}$–Cys$^{103}$]-$R_2$ protein) and any of one or more NSAIDs for the treatment of TNF-mediated diseases, as defined above, including acute and chronic inflammation such as rheumatic diseases (e.g., lyme disease, juvenile (rheumatoid) arthritis, osteoarthritis, psoriatic arthritis, rheumatoid arthritis and staphylococcal-induced ("septic") arthritis); and graft versus host disease. NSAIDs owe their anti-inflammatory action, at least in part, to the inhibition of prostaglandin synthesis (Goodman and Gilman in "The Pharmacological Basis of Therapeutics," MacMillan, 7th Edition (1985)). NSAIDs can be characterized into nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones.

In a specific embodiment, the present invention is directed to the use of a truncated sTNFR product (e.g., $R_1$-[Cys$^{19}$–Cys$^{103}$]-$R_2$ protein) in combination (pretreatment, post-treatment or concurrent treatment) with any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate and sulfasalazine. Structurally related salicylic acid derivatives having similar analgesic and anti-inflammatory properties are also intended to be encompassed by this group.

In a specific embodiment, the present invention is directed to the use of a truncated sTNFR product (e.g., $R_1$-[Cys$^{19}$–Cys$^{103}$]-$R_2$ protein) in combination (pretreatment, post-treatment or concurrent treatment) with any of one or more propionic acid derivatives, prodrug esters or pharmaceutically acceptable salts thereof. The propionic acid derivatives, prodrug esters and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In a specific embodiment, the present invention is directed to the use of a truncated sTNFR product (e.g., $R_1$-[Cys$^{19}$–Cys$^{103}$]-$R_2$ protein) in combination (pretreatment, post-treatment or concurrent treatment) with any of one or more acetic acid derivatives, prodrug esters or pharmaceutically acceptable salts thereof. The acetic acid derivatives, prodrug esters and pharmaceutically acceptable salts thereof comprise: acemetacin, alclofenac, amfenac, bufexamac, cinmetacin, clopirac, delmetacin, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, zidometacin and zomepirac. Structurally related acetic acid derivatives having similar analgesic and anti-inflammatory properties are also intended to be encompassed by this group.

In a specific embodiment, the present invention is directed to the use of a truncated sTNFR product (e.g., $R_1$-[Cys$^{19}$–Cys$^{103}$]-$R_2$ protein) in combination (pretreatment, post-treatment or concurrent treatment) with any of one or more fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefanamic acid, niflumic acid, talniflumate, terofenamate, tolfenamic acid and ufenamate. Structurally related fenamic acid derivatives having similar analgesic and anti-inflammatory properties are also intended to be encompassed by this group.

In a specific embodiment, the present invention is directed to the use of a truncated sTNFR product (e.g., $R_1$-[Cys$^{19}$–Cys$^{103}$]-$R_2$ protein) in combination (pretreatment, post-treatment or concurrent treatment) with any of one or more carboxylic acid derivatives, prodrug esters or pharmaceutically acceptable salts thereof. The carboxylic acid derivatives, prodrug esters and pharmaceutically acceptable salts thereof which can be used comprise: clidanac, diflunisal, flufenisal, inoridine, ketorolac and tinoridine.

Structurally related carboxylic acid derivatives having similar analgesic and anti-inflammatory properties are also intended to be encompassed by this group.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more butyric acid derivatives, prodrug esters or pharmaceutically acceptable salts thereof. The butyric acid derivatives, prodrug esters and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more oxicams, prodrug esters or pharmaceutically acceptable salts thereof. The oxicams, prodrug esters and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more pyrazoles, prodrug esters or pharmaceutically acceptable salts thereof. The pyrazoles, prodrug esters and pharmaceutically acceptable salts thereof which may be used comprise: difenamizole and epirizole. Structurally related pyrazoles having similar analgesic and anti-inflammatory properties are also intended to be encompassed by this group.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more pyrazolones, prodrug esters or pharmaceutically acceptable salts thereof. The pyrazolones, prodrug esters and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more of the following NSAIDs: ε-acetamidocaproic acid, S-adenosylmethionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprolm, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the above NSAIDs are also intended to be encompassed by this group.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more corticosteroids, prodrug esters or pharmaceutically acceptable salts thereof for the treatment of TNF-mediated diseases, as defined above, including acute and chronic inflammation such as rheumatic diseases (e.g., lyme disease, juvenile (rheumatoid) arthritis, osteoarthritis, psoriatic arthritis, rheumatoid arthritis and staphylococcal-induced ("septic") arthritis); and multiple sclerosis. Corticosteroids, prodrug esters and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more slow-acting antirheumatic drugs (SAARDs) or disease modifying antirheumatic drugs (DMARDS), prodrug esters or pharmaceutically acceptable salts thereof for the treatment of TNF-mediated diseases, as defined above, including acute and chronic inflammation such as rheumatic diseases (e.g., lyme disease, juvenile (rheumatoid) arthritis, osteoarthritis, psoriatic arthritis, rheumatoid arthritis and staphylococcal-induced ("septic") arthritis); and multiple sclerosis. SAARDs or DMARDS, prodrug esters and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more COX2 inhibitors, their prodrug esters or pharmaceutically acceptable salts thereof for the treatment of TNF-mediated diseases, as defined above, including acute and chronic inflammation. Examples of COX2 inhibitors, prodrug esters or pharmaceutically acceptable salts thereof include, for example, celecoxib. Structurally related COX2 inhibitors having similar analgesic and anti-inflammatory properties are also intended to be encompassed by this group.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more antimicrobials, prodrug esters or pharmaceutically acceptable salts thereof for the treatment of TNF-mediated diseases, as defined above, including acute and chronic inflammation. Antimicrobials include, for example, ampicillin, amoxycillin, aureomicin, bacitracin, ceftazidime, ceftriaxone, cefotaxime, cephachlor, cephalexin, cephradine, ciprofloxacin, clavulanic acid, cloxacillin, dicloxacillan, erythromycin, flucloxacillan, gentamicin, gramicidin, methicillan, neomycin, oxacillan, penicillin and vancomycin. Structurally related antimicrobials having similar analgesic and anti-inflammatory properties are also intended to be encompassed by this group.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more of the following compounds for the treatment of TNF-mediated diseases, as defined above, including acute and chronic inflammation: granulocyte colony stimulating factor; thalidomide; BN 50730; tenidap; E 5531; tiapafant PCA 4248; nimesulide; panavir; rolipram; RP 73401; peptide T; MDL 201,449A; (1R,3S)-Cis-1-[9-(2,6-diaminopurinyl)]-3-hydroxy-4-cyclopentene hydrochloride; (1R,3R)-trans-1-[9-(2,6-diamino)purine]-3-acetoxycyclopentane; (1R,3R)-trans-1-[9-adenyl)-3-azidocyclopentane hydrochloride and (1R,3R)-trans-1-[6-hydroxy-purin-9-yl)-3-azidocyclopentane.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with one or more additional TNF inhibitors for the treatment of TNF-mediated diseases, as defined above, including acute and chronic inflammation. TNF inhibitors include compounds and proteins which block in vivo synthesis or extracellular release of TNF, including the following compounds.

Additional TNF inhibitors include anti-TNF antibodies (e.g., MAK 195F Fab antibody (Holler et al. (1993), 1st International Symposium on Cytokines in Bone Marrow Transplantation, 147; CDP 571 anti-TNF monoclonal antibody (Rankin et al. (1995), *British Journal of Rheumatology*, 34:334–342, the disclosure of which is hereby incorporated by reference); BAY X 1351 murine anti-tumor necrosis factor monoclonal antibody (Kieft et al. (1995), 7th European Congress of Clinical Microbiology and Infectious Diseases, 9, the disclosure of which is hereby incorporated by reference); CenTNF cA2 anti-TNF monoclonal antibody (Elliott et al. (1994), *Lancet*, 344:1125–1127 and Elliott et al. (1994), *Lancet*, 344:1105–1110, the disclosures of which are hereby incorporated by reference).

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with the soluble recombinant human Fas antigen or recombinant versions thereof (WO 96/20206 and Mountz et al., *J. Immunology*, 155:4829–4837; and EP 510 691), the disclosures of which are hereby incorporated by reference. WO 96/20206 discloses secreted human Fas antigen (native and recombinant, including an Ig fusion protein), methods for isolating the genes responsible for coding the soluble recombinant human Fas antigen, methods for cloning the gene in suitable vectors and cell types, and methods for expressing the gene to produce the inhibitors. EP 510 691 teaches DNAs coding for human Fas antigen, including soluble Fas antigen, vectors expressing for said DNAs and transformants transfected with the vector. When administered parenterally, doses of a Fas antigen fusion protein each are generally from 1 micrograms/kg to 100 micrograms/kg.

In a specific embodiment, the present invention is directed to the use of a truncated sTNFR product (e.g., $R_1$-[$Cys^{19}$–$Cys^{103}$]-$R_2$ protein) in combination (pretreatment, post-treatment or concurrent treatment) with any of one or more interleukin-1 inhibitors for the treatment of TNF-mediated diseases, as defined above, including acute and chronic inflammation such as rheumatic diseases (e.g., lyme disease, juvenile (rheumatoid) arthritis, osteoarthritis, psoriatic arthritis, rheumatoid arthritis and staphylococcal-induced ("septic") arthritis); brain injury as a result of trauma, epilepsy, hemorrhage or stroke; and multiple sclerosis. Classes of interleukin-1 inhibitors include interleukin-1 receptor antagonists (any compound capable of specifically preventing activation of cellular receptors to IL-1) such as IL-1ra, as described below; anti-IL-1 receptor monoclonal antibodies (e.g., EP 623674, the disclosure of which is hereby incorporated by reference); IL-1 binding proteins such as soluble IL-1 receptors (e.g., U.S. Pat. No. 5,492,888, U.S. Pat. No. 5,488,032, U.S. Pat. No. 5,464,937, U.S. Pat. No. 5,319,071 and U.S. Pat. No. 5,180,812, the disclosures of which are hereby incorporated by reference); anti-IL-1 monoclonal antibodies (e.g., WO 9501997, WO 9402627, WO 9006371, U.S. Pat. No. 4,935,343, EP 364778, EP 267611 and EP 220063, the disclosures of which are hereby incorporated by reference); IL-1 receptor accessory proteins, e.g., WO 96/23067 (the disclosure of which is hereby incorporated by reference) and other compounds and proteins which block in vivo synthesis or extracellular release of IL-1.

Interleukin-1 receptor antagonist (IL-1ra) is a human protein that acts as a natural inhibitor of interleukin-1. Preferred receptor antagonists, as well as methods of making and methods of using thereof, are described in U.S. Pat. No. 5,075,222 (referred to herein as the '222 patent); WO 91/08285; WO 91/17184; AU 9173636; WO 92/16221; WO93/21946; PCT International Application No. US97/02131, which teaches a pharmaceutical composition comprising (a) an effective amount of controlled release polymer (e.g., hyaluronic acid) and (b) an effective amount of an IL-1ra; WO 94/06457; WO 94/21275; FR 2706772; WO 94/21235; DE 4219626, WO 94/20517; and WO 96/22793, the disclosures of which are incorporated herein by reference. The proteins include glycosylated as well as non-glycosylated IL-1 receptor antagonists.

Specifically, three preferred forms of IL-1ra (IL-1raα, IL-1raβ and IL-1rax), each being derived from the same DNA coding sequence, are disclosed and described in U.S. Pat. No. 5,075,222 by Hannum et al., entitled "Interleukin-1 Inhibitors." This U.S. Patent, referred to herein as the '222 patent, is specifically incorporated herein by reference. All three of these interleukin-1 inhibitors possess similar functional and immunological activities. Methods for producing IL-1 inhibitors, particularly IL-1ras, are also disclosed in the '222 patent. One disclosed method involves isolating the inhibitors from human monocytes (where they are naturally produced). A second disclosed method involves isolating the gene responsible for coding the IL-1ras, cloning the gene in suitable vectors and cell types, expressing the gene to produce the IL-1ras and harvesting the IL-1ras. The latter method, which is exemplary of recombinant DNA methods in general, is a preferred method of the present invention. In a specific embodiment, an IL-1ra contains an N-terminal methionyl group as a consequence of expression in *E. coli*. The present invention also includes modified IL-1ras. The modified IL-1ras include, for example, muteins of such inhibitors in which a cysteine residue is substituted for an amino acid at one or more sites in the amino acid sequence of a naturally-occurring inhibitor. Such muteins may then be site-selectively reacted with functionalized polyethylene glycol (PEG) units or other sulfhydryl-containing polyethers to create IL-1ra PEG species. PCT Publication No. WO 92/16221 discloses a number of modified IL-1ra species and methods of making such PEG modified inhibitors.

An additional class of interleukin-1 inhibitors includes compounds capable of specifically preventing activation of cellular receptors to IL-1. Such compounds include IL-1 binding proteins, such as soluble receptors and monoclonal antibodies. Such compounds also include monoclonal antibodies to the receptors.

A further class of interleukin-1 inhibitors includes compounds and proteins which block in vivo synthesis and/or extracellular release of IL-1. Such compounds include agents which affect transcription of IL-1 genes or processing of IL-1 preproteins.

The above is by way of example and does not preclude other treatments to be used concurrently with these anti-inflammatory compounds that are known by those skilled in the art or that could be arrived at by those skilled in the art using the guidelines set forth in this specification.

It is especially advantageous to formulate compositions of the additional anti-inflammatory compounds in dosage unit form for ease of administration and uniformity of dosage. "Dosage unit form" as used herein refers to physically discrete units suited as unitary dosages for the mammalian subjects to be treated, each unit containing a predetermined quantity of additional anti-inflammatory compounds calculated to produce the desired therapeutic effect in association with the required pharmaceutical carrier. As used herein, "pharmaceutically acceptable carrier" includes any and all solvents, dispersion media, coating, antibacterial and antifungal agents, isotonic and absorption delaying agents and the like which are compatible with the active ingredient and with the mode of administration and other ingredients of the formulation and not deleterious to the recipient. The use of such media and agents is well known in the art (see for example, *Remington's Pharmaceutical Sciences,* 18th Ed. (1990), Mack Publishing Co., Easton, Pa. 18042, pages 1435–1712, the disclosure of which is hereby incorporated by reference). Supplementary active ingredients can also be incorporated into the compositions.

For oral therapeutic administration, the additional anti-inflammatory compound may be incorporated with excipients and used in the form of ingestible tablets, buccal tablets, troches, capsules, elixers, suspensions, syrups, wafers and the like, or it may be incorporated directly with the food in the diet. The tablets, troches, pills, capsules and the like may also contain the following: a binder such as gum tragacanth, acacia, corn starch or gelatin; excipients such as dicalcium phosphate; a disintegrating agent such as corn starch, alginic acid and the like; a lubricant such as magnesium stearate; a sweetening agent such as sucrose, lactose or saccharin; or a flavoring agent such as peppermint, oil of wintergreen or cherry or orange flavoring. When the dosage unit form is a capsule, it may contain, in addition to material of the above type, a liquid carrier. Various other materials may be present as a coating or to otherwise modify the physical form of the dosage unit. For instance, tablets, pills or capsules may be coated with shellac, sugar or both. Of course, any material used in preparing any dosage unit form should be pharmaceutically pure and substantially non-toxic in the amounts employed. In addition, the additional anti-inflammatory compound may be incorporated into a sustained-release preparation and formulation. The amount of the additional anti-inflammatory compound in such a therapeutically useful composition is such that a suitable dosage will be obtained.

For parenteral therapeutic administration, each additional anti-inflammatory compound may be incorporated with a sterile injectable solution. The sterile injectable solution may be prepared by incorporating the additional anti-inflammatory compound in the required amount in an appropriate pharmaceutically acceptable carrier, with various other ingredients enumerated below (required), followed by filtered sterilization. In the case of dispersions, each may be prepared by incorporating the additional anti-inflammatory compound into a sterile vehicle which contains the basic dispersion medium and the required other ingredients from those enumerated above. In the case of sterile injectable solutions, each may be prepared by incorporating a powder of the additional anti-inflammatory compound and, optionally, any additional desired ingredient from a previously sterile-filtered solution thereof, wherein the powder is prepared by any suitable technique (e.g., vacuum drying and freeze drying).

The specific dose of the additional anti-inflammatory compound is calculated according to the approximate body weight or surface area of the patient. Other factors in determining the appropriate dosage can include the acute or chronic inflammatory disease or condition to be treated or prevented, the severity of the disease, the route of administration, and the age, sex and medical condition of the patient. Further refinement of the calculations necessary to determine the appropriate dosage for treatment involving each of the above-mentioned formulations is routinely made by those skilled in the art. Dosages can also be determined through the use of known assays for determining dosages used in conjunction with appropriate dose-response data.

Thus, for example, it is within the scope of the invention that doses of the additional anti-inflammatory compounds selected for treating a particular acute or chronic inflammatory disease such as rheumatic diseases (e.g., lyme disease, juvenile (rheumatoid) arthritis, osteoarthritis, psoriatic arthritis, rheumatoid arthritis and staphylococcal-induced ("septic") arthritis) can be varied to achieve a desired therapeutic effect. Where one of the additional anti-inflammatory compounds has side effects, it can be given to patients during alternate treatment periods of combination therapy. For example, chronic methotrexate treatment is associated with gastrointestinal, hepatic, bone marrow and pulmonary toxicity (Sandoval et al. (1995), *British Journal of Rheumatology*, 34:49–56, the disclosure of which is hereby incorporated by reference).

Tests for monitoring the improvement of a disease can include specific tests directed, for example, to the determination of systemic response to inflammation, which include the erythrocyte sedimentation rate (ESR) and acute phase reactants (APR). Observations are made of the swelling, etc. of the afflicted body parts. Improvement in stiffness, and grip (where applicable), and reduction in pain of the patient is also observed. If the patient's condition is stable, he is re-treated at the same dosage weekly and is evaluated weekly. Provided the patient's condition is stable, the treatment may be continued. After six months of treatment, anatomical changes of the skeleton are determined by radiologic imaging, for example by X-radiography.

At the end of each period, the patient is again evaluated. Comparison of the pre-treatment and post-treatment radiological assessment, ESR and APR indicates the efficacy of the treatments. According to the efficacy of the treatments and the patient's condition, the dosage may be increased or maintained constant for the duration of treatment.

Preferably, the present invention is directed to a method with, optionally, one of the following combinations to treat or prevent an acute or chronic inflammatory disease and condition, as defined above, such as rheumatic diseases (e.g., lyme disease, juvenile (rheumatoid) arthritis, osteoarthritis, psoriatic arthritis, rheumatoid arthritis and staphylococcal-induced ("septic") arthritis): a truncated sTNFR product (e.g., $R_1$-[$Cys^{19}$–$Cys^{103}$]-$R_2$ protein) and methotrexate; a truncated sTNFR product (e.g., $R_1$-[$Cys^{19}$–$Cys^{103}$]-$R_2$ protein), methotrexate and an IL-1 inhibitor, preferably IL-1ra; a truncated sTNFR product (e.g., $R_1$-[$Cys^{19}$–$Cys^{103}$]-$R_2$ protein) and any one or more of methotrexate, an immunosuppressant (e.g., cyclosporin), ciprofloxacin, the Fas antigen and an IL-1 inhibitor, preferably IL-1ra; a truncated sTNFR product (e.g., $R_1$-[$Cys^{19}$–$Cys^{103}$]-$R_2$ (protein) and methotrexate and an immunosuppressant (e.g., cyclosporin); a truncated sTNFR product (e.g., $R_1$-[$Cys^{19}$–$Cys^{103}$]-$R_2$ protein) and methotrexate and ciprofloxacin; and a truncated sTNFR product (e.g., $R_1$-[$Cys^{19}$–$Cys^{103}$]-$R_2$ protein) and methotrexate and an IL-1 inhibitor, preferably IL-1ra; a truncated sTNFR product (e.g., $R_1$-[$Cys^{19}$–$Cys^{103}$]-$R_2$ protein) and any one or more of methotrexate, sulphasazine and hydroxychloroquine; a truncated sTNFR product (e.g., $R_1$-[$Cys^{19}$–$Cys^{103}$]-$R_2$ protein), methotrexate and hydroxychloroquine; and a truncated sTNFR product (e.g., $R_1$-[$Cys^{19}$–$Cys^{103}$]-$R_2$ protein), methotrexate and sulphasazine.

In a specific preferred embodiment, the method comprises the administration (e.g., intra-articular, subcutaneous or intramuscular) of a truncated sTNFR product (e.g., $R_1$-[$Cys^{19}$–$Cys^{103}$]-$R_2$ protein, optionally formulated in a sustained release formulation (e.g., hyaluronan).) optionally in combination (pretreatment, post-treatment or concurrent treatment) with methotrexate and/or an IL-1 inhibitor (e.g., IL-1ra) and/or the soluble recombinant human Fas antigen to treat rheumatic diseases, as defined above (e.g., lyme disease, juvenile (rheumatoid) arthritis, osteoarthritis, psoriatic arthritis, rheumatoid arthritis and staphylococcal-induced ("septic") and the symptoms associated therewith.

In a specific preferred embodiment, the method comprises the administration (e.g., intravenous or intraventricular) of a truncated sTNFR product (e.g., $R_1$-[$Cys^{19}$–$Cys^{103}$]-$R_2$ protein, optionally formulated in a sustained release formulation (e.g., hyaluronan)) optionally in combination (pretreatment, post-treatment or concurrent treatment) with tissue plasminogen activator and/or an IL-1 inhibitor (e.g., IL-1ra) to treat brain injury as a result of trauma, epilepsy, hemorrhage or stroke, each of which may lead to neurodegeneration.

In a specific preferred embodiment, the method comprises the administration (e.g., subcutaneous or intramuscular) of a truncated sTNFR product (e.g., $R_1$-[$Cys^{19}$–$Cys^{103}$]-$R_2$ protein, optionally formulated in a sustained release formulation (e.g., hyaluronan)) optionally in combination (pretreatment, post-treatment or concurrent treatment) with one or more of a corticosteroid, cyclosporin, FK-506, or an interferon (e.g., alpha interferon, beta interferon, gamma interferon or consensus interferon) and/or IL-1ra to treat multiple sclerosis.

In a specific preferred embodiment, the method comprises the administration (e.g., subcutaneous or intramuscular) of a truncated sTNFR product (e.g., $R_1$-[$Cys^{19}$–$Cys^{103}$]-$R_2$ protein, optionally formulated in a sustained release formulation (e.g., hyaluronan)) optionally in combination (pretreatment, post-treatment or concurrent treatment) with G-CSF and/or IL-1ra to treat inflammatory bowel disease.

In a specific preferred embodiment, the method comprises the administration (e.g., subcutaneous or intramuscular) of a truncated sTNFR product (e.g., $R_1$-[$Cys^{19}$–$Cys^{103}$]-$R_2$ protein, optionally formulated in a sustained release formulation (e.g., hyaluronan)) optionally in combination (pretreatment, post-treatment or concurrent treatment) with leptin, Marinol™ or Megace™ to treat cachexia/anorexia.

In a specific preferred embodiment, the method comprises the administration (e.g., subcutaneous, intraventricular or intrathecal) of a truncated sTNFR product (e.g., $R_1$-[$Cys^{19}$–$Cys^{103}$]-$R_2$ protein, optionally formulated in a sustained release formulation (e.g., hyaluronan)) optionally in combination (pretreatment, post-treatment or concurrent treatment) with an NSAID (e.g., indomethacin) and/or an IL-1 inhibitor (e.g. IL-1ra) to treat Alzheimer's disease.

In a specific preferred embodiment, the method comprises the administration (e.g., subcutaneous, intraventricular or intrathecal) of a truncated sTNFR product (e.g., $R_1$-[$Cys^{19}$–$Cys^{103}$]-$R_2$ protein, optionally formulated in a sustained release formulation (e.g., hyaluronan)) optionally in combination (pretreatment, post-treatment or concurrent treatment) with a soluble recombinant human Fas antigen to treat cancer (e.g., leukemias); diabetes (e.g., juvenile onset Type 1 diabetes mellitus); graft versus host rejection; hepatitis; ischemic/reperfusion injury, including cerebral ischemia (brain injury as a result of trauma, epilepsy, hemorrhage or stroke, each of which may lead to neurodegeneration); neuroinflammatory diseases; rheumatic diseases, as defined above (e.g., lyme disease, juvenile (rheumatoid) arthritis, osteoarthritis, psoriatic arthritis, rheumatoid arthritis and staphylococcal-induced ("septic") and tissue transplantation.

Other aspects and advantages of the present invention will be understood upon consideration of the following illustrative examples.

EXAMPLES

Standard methods for many of the procedures described in the following examples, or suitable alternative procedures, are provided in widely recognized manuals of molecular biology such as, for example, Sambrook et al. (1989), supra and Ausubel et al. (1990), supra. For the reader's convenience, "mL" refers to milliliters, "L" refers to liters.

Example I

The following example teaches the production of various forms of truncated, recombinant soluble TNFR-I: $NH_2$-MDSVCPQGKYIHPQNNSIC-[$Cys^{19}$–$Cys^{103}$]-FC—COOH (sTNFR-I 2.6D/C105); $NH_2$-MDSVCPQGKYIHPQNNSIC-[$Cys^{19}$–$Cys^{103}$]-FNCSL-COOH (sTNFR-I 2.6D/C106); $NH_2$-MDSVCPQGKYIHPQNNSIC-[$Cys^{19}$–$Cys^{103}$]-FN—COOH (sTNFR-I 2.6D/N105); $NH_2$-MYIHPQNNSIC-[$Cys^{19}$–$Cys^{103}$]-FNCSL-COOH (sTNFR-I 2.3D/d8); $NH_2$-M-[$Cys^{19}$–$Cys^{103}$]-FNCSL-COOH (sTNFR-I 2.3D/d18) and $NH_2$-MSIS-[$Cys^{19}$–$Cys^{103}$]-FNCSL-COOH (sTNFR-I 2.3D/d15).

A. Preparation of DNA 1. sTNFR-I 2.6D/C106

PCR amplification of sTNFR-I 2.6D/C106 is carried out using as a template a cloned cDNA derived from the clone lambda-gt107ctnfbp (EP 422339) and the following PCR primers:

```
5' OLIGO#1: (SEQ ID NO:68)
5'-GGTTAGCCATATGGACAGCGTTTGCCCCCAA-3'

3' OLIGO#2: (SEQ ID NO:69)
5'-CCCAAGCTTTTACAGAGAGCAATTGAAGCACTG-3'
```

OLIGO#1 and OLIGO#2 encode NdeI and HindIII and anneal to the 5' and 3' end of the truncated gene, respectively. PCR amplification is run for 25 cycles; each cycle consisting of 30 seconds at 94° C. for denaturation, 15 seconds at 55° C. for annealing, and 1 minute at 72° C. for elongation [Model 2400 thermocycler (Perkin-Elmer Cetus, Norwalk, Conn.)]. The PCR product is purified using a QIAquick™ PCR Purification Kit (QIAGEN, Chatsworth, Calif.) according to the manufacturer's instructions. The purified PCR product is cut with NdeI and HindIII then gel purified using the QIAquick™ Gel Extraction Kit (QIAGEN, Chatsworth, Calif.) according to the manufacturer's instructions. The gel isolated PCR product is ligated into pAMG11 (WO 95/26746) and transformed into FM15 E. coli cells (ATCC 55765).

2. sTNFR-I 2.6D/C105

PCR amplification of sTNFR-I 2.6D/C105 is carried out using the sTNFR-I 2.6D/C106 plasmid DNA as a template and the following PCR primers:

```
OLIGO#3: (SEQ ID NO:70)
5'-ACTCGA GGATCCGCGGATAAATAAGTAACGATCCGGTCCA-3'
```

```
OLIGO#4: (SEQ ID NO:71)
5'-CAGGTCGGATCCTATCAGCAGAAGCACTGGAAAAGGTTTTC-3'
```

OLIGO#3 and OLIGO#4 encode BamHI and mutation N(105)C followed by a stop codon. The OLIGOS are designed to extend completely around the template for incorporation of the new BamHI site for ligation. PCR amplification is run for 35 cycles; 10 cycles, each cycle consisting of 10 seconds at 92° C. for denaturation, 30 seconds at 55° C. for annealing, and 4 minutes at 68° C. for elongation followed by 25 cycles, each cycle consisting of 10 seconds at 92° C. for denaturation, 30 seconds at 55° C. for annealing, and 4 minutes+20 seconds at 68° C. for elongation [Model 2400 thermocycler (Perkin-Elmer Cetus, Norwalk, Conn.)]. The PCR product is gel purified using the QIAquick™ Gel Extraction Kit (QIAGEN, Chatsworth, Calif.) according to the manufacturer's instructions, cut with BamHI, phenol/chloroform extracted and ethanol precipitated. It is then resuspended, ligated into pAMG11, and transformed into FM15 E. coli cells.

3. sTNFR-I 2.6D/N105

PCR amplification of sTNFR-I 2.6D/N105 is carried out using the sTNFR-I 2.6D/C106 plasmid DNA as a template and the following PCR primers:

```
5' OLIGO#5: (SEQ ID NO:72)
5'-GGTTAGCCATATGGACAGCGTTTGCCCCCAA-3'

3' OLIGO#6: (SEQ ID NO:73)
5'-CGCGGATCCCTATTAATTGAAGCACTGGAAAAGG-3'
```

OLIGO#5 and OLIGO#6 encode NdeI and BamHI and anneal to the 5' and 3' end of the truncated gene, respectively. PCR amplification is run for 30 cycles; each cycle consisting of 45 seconds at 95° C. for denaturation, one minute at 65° C. for annealing, and two minutes at 72° C. for elongation [Model 2400 thermocycler (Perkin-Elmer Cetus, Norwalk, Conn.)].

The PCR product is purified using the Wizard™ DNA Clean-Up System (Promega, Madison, Wis.) according to the manufacturer's instructions. The purified PCR product is cut with NdeI and BamHI, phenol/chloroform extracted and ethanol precipitated. It is then resuspended, ligated into pAMG11 and transformed into FM15 E. coli cells.

Based upon the description of the present invention, those of ordinary skill in the art will appreciate that a variety of materials and methods may readily be used or adapted for suitable expression in a host cell (e.g., E. coli and other bacteria).

4. sTNFR 2.3D/d18; sTNFR-I 2.3D/d8 and sTNFR-I 2.3D/d15

PCR amplification of sTNFR-I 2.3D/d18; sTNFR-I 2.3D/d8 and sTNFR-I 2.3D/d15 are each carried out using 2.6D/C106 plasmid DNA as a template and the following PCR primers:

```
sTNFR-I 2.3D/d8 PCR Primers:
5' OLIGO#7:                             (SEQ ID NO:74)
5'-CCCCATATGTATATCCACCCTCAAAATAAT-3'

3' OLIGO#8:                             (SEQ ID NO:75)
5'-CCCAAGCTTTTACAGAGAGCAATTGAAGCACTG-3' sTNFR-I 2.3D/d15 PCR Primers
5' OLIGO#9:                             (SEQ ID NO:76)
5'-CCCCATATGTCGATTAGCTGTACCAAGTGCCACAAAGG-3'
```

-continued

```
3' OLIGO#10:                                (SEQ ID NO:77)
5'-CCCAAGCTTTTACAGAGAGCAATTGAAGCACTG-3' sTNFR-I 2.3D/d18 PCR Primers
5' OLIGO#11:                                (SEQ ID NO:78)
5'-CCCCATATGTGTACCAAGTGCCACAAAGGA-3'

3' OLIGO#12:                                (SEQ ID NO:79)
5'-CCCAAGCTTTTACAGAGAGCAATTGAAGCACTG-3'
```

OLIGO#7, OLIGO#9 and OLIGO#11 each encode NdeI and OLIGO#8, OLIGO#10 and OLIGO#12 each encode HindIII. PCR amplifications are run for 25 cycles; each cycle consisting of 45 seconds at 95° C. for denaturation, 1 minute at 65° C. for annealing, and 2 minutes at 72° C. for elongation [Model 2400 thermocycler (Perkin-Elmer Cetus, Norwalk, Conn.)]. The PCR products are purified using the Wizard™ DNA Clean-Up System (Promega, Madison, Wis.) according to the manufacturer's instructions. The purified PCR products are cut with NdeI and HindIII, phenol/chloroform extracted and ethanol precipitated. They are resuspended, ligated into pAMG11, and transformed into FM15 E. coli cells.

B. Production in E. coli:

Initially, one small freshly cultured inocula of the desired recombinant E. coli clone harboring the desired construct for sTNFR-I 2.6D/N105, sTNFR-I 2.6D/C105 sTNFR-I 2.6D/C106, sTNFR 2.3D/d18, sTNFR-I 2.3D/d8 and sTNFR-I 2.3D/d15 is started by transferring the entire contents of a frozen glycerol stock seed ampule (ca. 1.5 mL) into a 2 L flask containing 500 mL of Luria broth. The culture is incubated in a gyratory shaker at 37° C. operating at 350 rpm. The density of the culture is determined by measuring absorbance at 660 nm ($OD_{660}$). The seed culture is grown to a density of $\geq 2.0$ $OD_{660}$, at which time 125 mL is aseptically transferred to the 15 L production fermentor containing 10 L of sterile growth medium.

The batch medium and fermentation conditions for the production fermentation are the complex medium fermentation conditions as described by Sniff (1993), "A Chemically-Defined Medium for the Overproduction of a Recombinant Protein in E. coli," thesis, Colorado State University. Generally, the reference teaches the use of a complex medium containing casein hydrolysate, salts, glycerin and antifoam, which are sterilized in the fermentor. After the tank is cooled to below 40° C., filter sterilized trace minerals and thiamine hydrochloride are added.

When the medium temperature is stable at 37° C., the medium is inoculated with the seed culture. Culture growth is monitored by measuring $OD_{660}$. The culture is maintained at a pH of 6.0 by the automatic addition of 5 M sodium hydroxide and 5 M hydrochloric acid. When the $OD_{660}$ is between 9.5 and 10.5, the culture is induced by the aseptic addition of sterile isopropyl β-D thiogalactopyranoside (IPTG) to a final concentration of 0.50 mM. The culture is harvested upon cessation of growth.

The culture medium and growth conditions are as described by Sniff (1993), supra, with the following exceptions: ammonium sulfate (2.0 g/L) and L-Cysteine hydrochloride monohydrate (1.0 g/L) are added to the medium; tetracycline hydrochloride is omitted from the medium; the pH is maintained at 6.0 with sodium hydroxide and hydrochloric acid, rather than at 7.0 with only sodium hydroxide; the growth temperature is increased to 37° C.; the inducer concentration has been increased from 0.15 mM to 0.50 mM IPTG; and the harvest criteria is based on cessation of growth rather than time after induction.

At the completion of the fermentation, the cells are harvested in centrifugation in 500 mL bottles. The cells are pelleted by centrifugation at 10,000 rpm for 30 minutes. The recovered cell paste is diluted to 15% solids in a breaking buffer composed of 50 mM Tris and 5 mM EDTA at pH 8.0. The suspended cells are then lysed by passing the solution through a homogenizer (APV Gaulin, Inc., Everett, Mass.) operating at 8000 psi pressure three times. The homogenate is then centrifuged at 10,000 rpm for 30 minutes to recover the inclusion bodies (IBs). The IBs are washed by resuspending in breaking buffer and centrifuging the solution a third time at 10,000 rpm for 30 minutes. The IBs are resuspended in deionized water (1:1 ratio) and centrifuged a final time at 10,000 rpm for 30 minutes for the second wash. The recovered, washed inclusion bodies for each protein are ready for solubilization, refold and purification. Each run yields approximately 200–250 g of IBs.

In an alternative embodiment, the truncated sTNFR-1 may be fermented as follows:

Initially, a small freshly cultured inoculum of the desired recombinant E. coli clone harboring the desired construct for sTNFR-I 2.6D/N105 or sTNFR-I 2.6D/C106 is started by transferring the entire contents of a frozen glycerol stock seed ampule (ca. 1.5 mL) into a 2 L flask containing 500 mL of 10 g/L BBL yeast extract, pH 7.0. The culture is incubated in a gyratory shaker at 33° C. operating at 300 rpm. The density of the culture is determined by measuring absorbance at 600 nm ($OD_{600}$). The seed culture is grown to a density of $\geq 2.0$ $OD_{600}$, at which time it is aseptically transferred (80 mL) to the 15 L production fermentor containing 7 L of sterile growth medium.

The production fermentation employs a fed-batch process. The batch medium is a complex medium containing yeast extract, salts, and antifoam, which are sterilized in the fermentor. After the tank is cooled to below 40° C., filter sterilized trace minerals, glucose, magnesium sulfate, and hexametaphosphate are added. Two feeds are employed, the first being a carbon containing feed (glucose/magnesium sulfate) and the second a nitrogen feed containing yeast extract.

When the batch medium temperature is stable at 33° C., the medium is inoculated with the seed culture. Culture growth is monitored by measuring $OD_{600}$. The culture is maintained at a pH of 7.0 by the automatic addition of ammonium hydroxide and 48.7% citric acid. When the $OD_{600}$ is between 8.0 and 12.0, feed I is initiated using an exponential feed rate. When the $OD_{600}$ is between 30 and 40, feed 2 is initiated using a constant feed rate. When the $OD_{600}$ reached 67–83, the culture is induced by the aseptic addition of sterile autoinducer (homoserine lactone) to a final concentration of 0.6 mg/L. Both feed I and II rates are changed to a constant rate at induction. The culture is harvested at 16±2 hrs post induction.

At the completion of the fermentation, the cells are harvested in centrifugation in 500 mL bottles. The cells are pelleted by centrifugation at 10,000 rpm for 30 minutes. The recovered cell paste is diluted to 15% solids in a breaking buffer composed of 50 mM Tris and 5 mM EDTA at pH 8.0. The suspended cells are then lysed by passing the solution through a homogenizer (APV Gaulin, Inc., Everett, Mass.) operating at 8000 psi pressure three times. The homogenate is then centrifuged at 10,000 rpm for 30 minutes to recover the inclusion bodies (IBs). The IBs are washed by resuspending in breaking buffer and centrifuging the solution a third time at 10,000 rpm for 30 minutes. The IBs are resuspended in deionized water (1:1 ratio) and centrifuged a final time at 10,000 rpm for 30 minutes for the second wash.

The recovered, washed inclusion bodies are ready for solubilization, refold and purification.

C. Solubilization/Refold

The washed IBs from each entire 10 L fermentation are solubilized in 800 mL of solubilization buffer (50 mM Tris, 8 M Urea, 160 mM cysteine pH9.5). The pH of the solubilization mixture is adjusted to 9.5 with 10N NaOH and allowed to stir at room temperature for 2–3 hours. Each run yielded approximately 200–250 g of IBs.

Each solubilization mixture is diluted 1:20 into cold Renaturation Buffer (50 mM Tris, 1.1M Urea). Each final volume is about 16 L. Thereafter each mixture is adjusted to pH 9.7 with 6N HCl, and slowly stirred at 4° C. for 2–3 days.

The pH of each mixture is then adjusted to 5.0 with glacial acetic acid and 6N HCl. In each mixture a precipitate is formed which is removed by centrifugation at 10,000×g on a Beckman Model J2-HS centrifuge. Each material is then filtered through a 5μm and a 0.22μm filter.

D. Purification

The refold materials are ready for column purification on an IX-1 SP-Sepharose Big Bead™ column (Pharmacia Biotech, Inc., Piscataway, N.J.).

IX-1 SP-Sepharose Big Bead™ column (4.4 cm×20 cm)

| Buffer A | Buffer B |
|---|---|
| 25 mM Acetate<br>50 mM NaCl<br>pH 5.0 | 25 mM Acetate<br>375 mM NaCl<br>pH 5.0 |

A column is equilibrated with 4–5 column volumes Buffer A prior to separate loadings of each refold material. The refold materials are separately loaded onto the column for purification. For each loading, the column is loaded with no more than twelve grams of protein per liter of resin. For each loading, the column is then washed with 3–4 column volumes of Buffer A (until U.V. returned to baseline). For each loading, protein is eluted off the column using a linear eight column volume increasing salt gradient running from 50–375 mM NaCl. The entire protein peak for each loading is collected into one pool. The collection of each protein peak is started when the U.V. absorbance rose to about 20% of peak maximum. Pooling is stopped when the earlier of either the U.V. absorbance reached about 50% of peak maximum or the absorbance stops declining.

Flowrate—7.5 cv/hr for the Equilibration, wash 15 cv/hr for the load 6 cv/hr for the elution Each column purification is run at 4° C.

Each IX-1 pool is ready for purification on a Toyo Pearl™ Butyl 650M HIC column (Toso Haas, Philadelphia, Pa.).

300 mL-Toyo Pearl Butyl™ 650M column (4.4 cm×20 cm)

| Buffer A | Dilution Buffer | Buffer B |
|---|---|---|
| 20 mM NaPO$_4$<br>1.8M NaCl, pH 6.0 | 40 mM Na NaPO$_4$ | Milli Q H$_2$O<br>4M NaCl pH 6.0 |

The column is equilibrated with 4–5 column volumes of Buffer A prior to separate loadings of each IX-1 pool material. Each IX-1 pool is diluted 1:1 with Dilution Buffer and the pH adjusted to 6.0. For each loading, the diluted IX-1 pool is loaded onto a column. For each loading, the column is loaded with no more than ten grams of protein per liter of resin. For each loading, the column is washed with 3 column volumes of buffer. For each loading, protein is eluted off the column with a linear eight column volume decreasing salt gradient running from 1.8M NaCl to H$_2$O. The collection of each protein peak is started when the U.V. absorbance rose to about 15–20% of peak maximum. Pooling is stopped when the earlier of either the U.V. absorbance reached about 50% of peak maximum or the absorbance stops declining.

Flowrate—6 cv/hr for the equilibration, load and wash 3 cv/hr for the elution

Each column purification is run at room temperature.

Each HIC pool is ready for concentration/ diafiltration.

Concentration/Diafiltration (C/D)

A 1 sq ft PLCC™ regenerated cellulose 5,000 M.W. cutoff membrane (Milli-Pore, Bedford, Mass.) is used for the C/D step for each HIC pool. Each HIC pool is concentrated down to around 200 mL and then diafiltrated against 6–7 volumes of 20 mM NaPO$_4$ pH6.0 until the conductivity is <4 mm hour.

Each concentration/diafiltration step is done at room temperature.

Each C/D pool is then ready for purification on an IX-2–365 mL SP-Sepharose HP™ column (Pharmacia Biotech, Inc., Piscataway, N.J.).

IX-2–365 mL SP-Sepharose HP™ column (5 cm×18.5 cm)

| Equilibration Buffer | Buffer A | Buffer B |
|---|---|---|
| 20 mM Na NaPO$_4$<br>pH 6.0 | 20 mM NaPO$_4$<br>pH 6.3 50 mM NaCl | 20 mM NaPO$_4$<br>pH 6.8 |

The column is equilibrated with 4 column volumes Equilibration Buffer prior to separate loadings of each C/D pool. Each C/D pool is loaded onto the column using no more then eight grams of protein per liter of resin. For each loading, the column is washed with 3 column volumes Equilibration Buffer followed by 3 column volumes Buffer A. For each loading, protein is eluted off the column with a linear eight column volume gradient consisting of a pH gradient from 6.3–6.8 and a salt gradient running from 0–50 mM NaCl (Buffer B). Pooling is started at 1.0 O.D. up the front side of the peak and stopped at 50% of the peak max on the back side.

In an alternative embodiment, the truncated sTNFR-1 may be solubilized, re-folded and purified as follows:

C.1 Solubilization/Refold

The washed IBs are solubilized with 8M urea, 60 mM Tris, 100 mM cysteine to give a final concentration of 6.5 M urea, 50 mM Tris and 80 mM cysteine, pH 9.4 and 5–10 mg/mL truncated sTNFR-1. (The latter is based on a quantitation of the amount of truncated sTNFR-1 in washed IBs on a g/L basis.) The material is allowed to stir at room temperature for 90 minutes and is then refolded by diluting 1:10 into cold (4–8° C.) 0.85M urea, 50 mM Tris, pH 9.8 (pH measurement taken at 4–8° C.).

The refold solution is allowed to stir for 24–72 hours at 4–8° C. At the end of this time, glacial acetic acid is added (~20 mM) and the pH is adjusted to 5.0. The precipitate that forms is removed by centrifugation and the supernatant saved for loading the first column.

D.1 Purification

The clarified acid precipitation pool is loaded onto an SP-Sepharose Big Bead™ column (Pharmacia Biotech, Inc., Piscataway, N.J.) that has been equilibrated with 20 mM sodium acetate, 75 mM NaCl, pH 5.0. The column is loaded with no more than 15 g truncated sTNFR-1 per L bed volume. After loading the column is washed with 3 column volumes of 20 mM sodium acetate, 75 mM NaCl, pH 5.0 and eluted with a linear 9 column gradient from 75 mM to 450 mM NaCl in 20 mM sodium acetate, pH 5.0. The entire SP-Sepharose Big Bead™ column (SP-BB) step is run at 4–8° C.

The SP-BB pool is diluted 1:1 with 2M NaCl, 60 mM acetate, pH 4.5 and the pH adjusted to 4.5 if necessary. The diluted SP-BB pool is loaded on to a Toyopearl™ Butyl 650M column (Toso Haas, Philadelphia, Pa.) that had been equilibrated with 1M NaCl, 30 mM acetate, pH 4.5. The column is loaded with ~10–13 grams of truncated sTNFR-1 per liter bed volume. After loading, the column is washed with 3 column volumes of 1M NaCl, 30 mM acetate, pH 4.5 and eluted with a linear 8 column volume gradient of 1M -0M NaCl in 30 mM acetate, pH 4.5.

The purified truncated sTNFR-1 fractions from the Butyl 650M column are pooled, diluted 1:5 with water and loaded onto an SP-Sepharose High Performance™ column (SP-HP) (Pharmacia Biotech, Inc., Piscataway, N.J.) that has been equilibrated with 30 mM acetate, pH 4.5 (loading no more than ~15 g/L bed volume). The column is then washed with 3 column volumes of 30 mM acetate, pH 4.5 and eluted with a linear 12 column volume gradient going from 100 mM to 400 mM NaCl in 30 mM acetate, pH 4.5. The purified truncated sTNFR-1 fractions are pooled and adjusted to pH 5.0 with NaOH.

C. PEGylation

1. Preparation of sTNFR-I 2.6D/N105-t-BuPEG(33 kDa).

To a cooled (4° C.), stirred solution of sTNFR-2.6D/N105 (3.5 mg/ml) in 50 mM sodium acetate, pH 4, is added a 3-fold molar excess of t-BuPEG (mono-t-butoxy-polyethylene glycol, average MW=33 kDa, Shearwater Polymers, Inc.). NaCNBH$_3$ is added to a final concentration of 20 mM, and the reaction mixture is stirred at 7° C. for 18–24 hours.

The extent of the protein modification during the course of the reaction is monitored by SEC HPLC using a TSKG3000sw$_{XL}$ column (Toso Haas, Montgomeryville, Pa.) eluting with 0.1 M sodium phosphate buffer pH 6.9, 0.5M NaCl, and 10% ethanol at 0.7 ml/min (Toso Haas, Montgomeryville, Pa.).

The pH of the reaction mixture is adjusted to ca. 3.5 with 1M HCl, and the reaction mixture is diluted with water to a final protein concentration of 1.5 mg/ml.

sTNFR-I 2.6D/N105-t-BuPEG(33 kDa) is separated from the excess of t-BuPEG and other reaction by-products by using a SP Sepharose HP 16/10™ ion-exchange chromatography (Pharmacia Biotech, Inc., Piscataway, N.J.).

The reaction mixture is loaded onto the column and the unreacted t-BuPEG is eluted with 3 column volumes of the starting Buffer A (20 mM sodium acetate, pH 4.0). The sTNFR-I 2.6D/N105-t-BuPEG(33 kDa) is eluted using a linear 20 column volume gradient from 0–30% Buffer B (1M NaCl in 20 mM acetate, pH 4.0. The eluent is monitored at 280 nm. Each fraction containing sTNFR-I 2.6D/N105-t-BuPEG(33 kDa) is analyzed by SDS-PAGE using 4–20% precast gradient gels (Novex, San Diego, Calif.). Based on SDS-PAGE analysis results, fractions are pooled, concentrated, and sterile filtered. Each final pool of purified sTNFR-I 2.6D/N105-t-BuPEG(33 kDa) is again analyzed by SDS-PAGE and SEC HPLC. This protein is formulated in 10 mM sodium phosphate, pH 6.5 and 20 mM NaCl.

2. Preparation of sTNFR-I 2.6D/N105–33kDa (MePEG)

To a cooled (7° C.), stirred solution of sTNFR-2.6D/N105 (4 mg/ml) is added 10% acetic acid until the pH is 5.0. To this solution is added 15 mM NaCNBH$_3$ and a 2-fold molar excess of t-butoxy PEG (t-butoxy polyethylene glycol, average MW=33 kDa, Shearwater Polymers, Inc.). The reaction mixture is stirred briefly at the same temperature and then allowed to incubate for ~18 hours.

After 18 hours protein concentration in the reaction mixture is adjusted to pH 3.0 with citric acid.

sTNFR-I 2.6D/N105-MePEG(33 kDa) is separated from the excess of MePEG and other reaction by-products by ion exchange chromatography using an SP Sepharose HP™ column (Pharmacia Biotech, Inc., Piscataway, N.J.).

The reaction mixture is loaded (no more than 8mg/ml of resin) onto the column and the unreacted MePEG is eluted with 3 column volumes of the starting buffer A (20 mM sodium citrate, pH 3.0). The sTNFR-I 2.6D/N105-MePEG (33 kDa) is eluted using a linear 16 column volume gradient from 0.1–0.5 M NaCl in 20 mM citrate, pH 3.0. The eluent is monitored at 280 nm. Each fraction containing sTNFR-I 2.6D/N105-MePEG(33 kDa) is analyzed by SDS-PAGE using 4–20% precast gradient gels (Novex, San Diego, Calif.). Based on SDS-PAGE analysis results, fractions are pooled, concentrated, and sterile filtered. Each final pool of purified sTNFR-I 2.6D/N105-MePEG(33 kDa) is again analyzed by SDS-PAGE. The purified sTNFR-I 2.6D/N105-MePEG(33 kDa) is concentrated to 5–20 mg/mL and formulated in either PBS, pH 6.5 (10 mM sodium phosphate, 35–100 mM NaCl) or 20 mM acetate, 100 mM NaCl, pH 5.0.

3. Preparation of sTNFR-I 2.6D/N105-MePEG(20 kDa)

The procedures of step A for the preparation of sTNFR-I 2.6D/N105-MePEG(33 kDa), are substantially repeated with the exception that MePEG (mono-methoxy-polyethylene glycol, average MW=20 kDa, Shearwater Polymers, Inc.) is substituted for the MePEG (mono-methoxy-polyethylene glycol, average MW=33 kDa, Shearwater Polymers, Inc.). This protein is formulated in 10 mM sodium phosphate, pH 6.5 and 20 mM NaCl.

4. Preparation of Additional Conjugates.

Additional conjugates of sTNFR-2.6D/N105 are prepared substantially as sTNFR-I 2.6D/N105-MePEG(33 kDa), with the exception that the following types of PEG aldehydes (Shearwater Polymers, Inc.) are used:

linear monofunctional-MW 5 kDa, 6 kDa, and 57 kDa;
branched monofunctional-MW 10 kDa, 20 kDa and 40kDa;
linear difunctional-MW 8kDa and 20kDa;
branched trifunctional-MW 10 kDa.

These proteins are formulated in 10 mM sodium phosphate, pH 6.5 and 20 mM NaCl.

5. Alternative Pegylation Method

In an alternative embodiment, the truncated sTNFR-1 molecules may be pegylated and purified by the following techniques:

The SP-HP eluate (3–5 mg/mL adjusted to pH 5.0) is reacted with 2 moles of polyethylene glycol (e.g., MePEG or t-BuPEG) per mole of sTNFR-I 2.6D/N105 (~5 grams of t-BuPEG per gram of sTNFR-I 2.6D/N105). After the dissolution of the polyethylene glycol, 10–20 mM sodium cyanoborohydride is added and the solution is allowed to incubate overnight at 7–15° C. At the end of the pegylation reaction (~18 hours) the reaction is quenched by adding 10 mM glycine.

The pegylation mixture is diluted with 4 volumes of 50 mM acetate, pH 4.0, adjusted to pH 4.0 if necessary, and loaded onto a SP-HP column that has been equilibrated with 50 mM acetate, pH 4.0. The column is loaded to no more than ~8 grams of sTNFR-2.6D/N105 per Liter bed volume.

After loading, the column is washed with 3 column volumes of Equilibration Buffer and eluted with a linear 0–0.3M NaCl gradient in 50 mM acetate, pH 4.0. The sTNFR-2.6D/N105-30 kDa monopegylated fractions are collected, adjusted to pH 5.0, concentrated and diafiltered into an isotonic formulation buffer. All purification steps are carried out at room temperature. The protein is formulated in either PBS, pH 6.5 (10 mM sodium phosphate, 35–100 mM NaCl) or 20 mM acetate, 100 mM NaCl, pH 5.0.

6. Preparation of sTNFR-I 2.6D/C105 dumbbell and sTNFR-I 2.6D/C106 dumbbell.

Sulfone activated polyethylene glycol (prepared and purified substantially in accordance with U.S. patent application Ser. No. 08/473,809, filed Jun. 7, 1995 and U.S. patent application Ser. No. 08/611,918, filed Mar. 6, 1996) [PEG-20,000-bis-vinyl sulfone], are used to dimerize proteins substantially in accordance with the method described in PCT Publication No. WO 95/34326, except for the reduction and reaction conditions. The proteins are reduced prior to the attachment of the polyethylene glycol with 4 mole DTT per one mole of protein at 5–6° C., pH 7.6. All reactions are performed in the presence of 30% glycerol. The dimerized proteins are termed sTNFR-I 2.6D/C105 db and sTNFR-I 2.6D/C106 db. Each protein is formulated in either PBS, pH 6.5 (10 mM sodium phosphate, 35–100 mM NaCl) or 20 mM acetate, 100 mM NaCl, pH 5.0.

7. Preparation of Comparative sTNFR-I Molecules (i). sTNFR-I 4D/N105 is prepared as described in EP 422339. sTNFR-I 4D/N105-t-BuPEG(33 kda) is prepared by pegylating sTNFR-I 4D/N105 substantially in accordance with the procedures set forth above for the pegylation of sTNFR-I 2.6D/N105-t-BuPEG (33 kDa). sTNFR-I 4D/N105-t-MePEG(33 kda) is prepared by pegylating sTNFR-I 4D/N105 substantially in accordance with the procedures set forth above for the pegylation of sTNFR-I 2.6D/N105-MePEG (33 kDa). sTNFR-I 4D/C105 and sTNFR-I 4D/C105 db are prepared as described in PCT Publication No. WO 95/34326. This protein is formulated in 10 mM sodium phosphate, pH 6.5 and 20 mM NaCl.

(ii). sTNFR-I 4D/C105-33 kDa(MePEG) is prepared by pegylating 4D/C105 substantially in accordance with the procedures set forth above for the pegylation of sTNFR-I 2.6D/C105-33 kDa(MePEG) with the exception that the reaction occurs at pH 7.5 with 1.3 moles of DTT per mole of sTNFR-I for ~5–6 hours, followed by removal of the DTT on an SP-Sepharose™ FF column and PEGylation with 1.5–3 moles of PEG per mole of protein for at least 15 hours at room temp. This protein is formulated in either PBS, pH 6.5 (10 mM sodium phosphate, 35–100 mM NaCl) or 20 mM acetate, 100 mM NaCl, pH 5.0.

(iii). sTNFR-I 3D/N105 (a truncation of the c-terminus 34 amino acids of sTNFR-I 4D/N105) is prepared as follows. PCR amplification is carried out using sTNFR-I 4D/N105 as the template and OLIGO#13 and OLIGO#14 which encode NdeI and HindII, respectively, and anneal to the 5' and 3' ends of the truncated gene, respectively. PCR amplifications are run for 25 cycles; each cycle consisting of 30 seconds at 94° C. for denaturation, 15 seconds at 60° C. for annealing, and 1 minute at 72° C. for elongation [Model 2400 thermocycler (Perkin-Elmer Cetus, Norwalk, Conn.)]. The PCR product is purified using a QIAquick™ PCR Purification Kit (QIAGEN, Chatsworth, Calif.). The purified PCR product is cut with NdeI and HindIII then gel purified using the QIAquick™ Gel Extraction Kit (QIAGEN, Chatsworth, Calif.). The gel isolated PCR product is ligated into pAMG11 and transformed into FM15 E. coli cells.

5' OLIGO#13: (SEQ ID NO:80)
5'-GGTTAGCCATATGGACAGCGTTTGCCCCCAA-3'

3' OLIGO#14: (SEQ ID NO:81)
5'-CCCAAGCTTTTAGGTGCACACGGTGTTCTGTTT-3'

This protein is formulated in 10 mM sodium phosphate, pH 6.5 and 20 mM NaCl.

(iv). sTNFR-I 3D/C105 (a truncation of the c-terminus 34 amino acids of sTNFR-I 4D/C105) is prepared substantially as sTNFR-I 3D/N105, with the exception that the template is sTNFR-I 4D/C105. sTNFR-I 3D/C105 is formulated in either PBS, pH 6.5 (10 mM sodium phosphate, 35–100 mM NaCl) or 20 mM acetate, 100 mM NaCl, pH 5.0.

(v). sTNFR-I 3D/C105 db is prepared substantially as sTNFR-I 4D/C105 db, with the exception that sTNFR-I 3D/C105 is used as the starting material instead of sTNFR-I 4D/C105. sTNFR-I 3D/C105 db is formulated in either PBS, pH 6.5 (10 mM sodium phosphate, 35–100 mM NaCl) or 20 mM acetate, 100 mM NaCl, pH 5.0.

Example II

Various forms of truncated, recombinant soluble TNFR-I are assessed for their ability to inhibit TNF activity.

A. WEHI Cytotoxicity Assay

The WEHI assay is an in vitro cell proliferation assay (Edwards et al. (1.991), *Endocrinology.* 128:989–996). The cell lines are sensitive to TNF-α (i.e., TNF-α is cytotoxic). In the presence of a TNF-α inhibitor, the cells are protected from the cytotoxic effect and thus are able to proliferate.

Protocol

TNF-sensitive WEHI 164 clone 13 cells (ATCC, Rockville, Md.) are suspended at a concentration of $20 \times 10^4$ cells/mL in RPMI (Gibco, Grand Island, N.Y.) medium supplemented with 5% Fetal Calf Serum (Hyclone, Ogden, Utah) and penicillin 50U/mL:streptomycin 50 mg/mL. One hundred microliters of this cell suspension are placed in each well of flat-bottomed 96-cell microtiter plates, and the cells are allowed to adhere for 4–6 hours at 37° C. in 5% $CO_2$. To each well 10 μL of a 0.0060 mg/mL actinomycin-D (Sigma Chemical Co., St. Louis, Mo.) is added. Ten microliters of recombinant human TNFα at 50 ng/ml (5 ng/ml final concentration) is added to each well. Serially diluted 2-fold concentrations of the various sTNFR forms (sTNFR-I 2.6D/C106, sTNFR-I 4D/C105 and sTNFR-I 4D/C105 db) are diluted PBS and then added to duplicate wells (10 μL/well) containing adherent WEHI 164 cells after the addition of recombinant human TNF-α. WEHI-164 clone 13 cells are incubated for 18 hours at 37° C. in 5% $CO_2$. After incubation, 10 mL of a 2 mg/mL solution of the organic dye MTT tetrazolium (3-[4,5-dimethylthiozol-2-yl]2,5-diphenyl tetrazolium bromide; Sigma Chemical Co., St. Louis, Mo.) is added, and cells are incubated for an additional 4–6 hours. Cells are solubilized by addition of 50 μL DMF/SDS solution (20% SDS and 50% N,N dimethylformamide, pH 4.7). The DMF/SDS solution is pipetted up and down several times until all MTT crystals are dissolved, and cells are incubated for an additional 2–22 hours. The absorbances (abs) are read on a Vmax reader at 570. The percent specific cytotoxicity is calculated from optical densities using the formula: % specific cytotoxicity=100% X [abs(cells+medium)−abs(cells+sample)]/abs(cells+medium)−abs(cells+TX−100)]. The number of units of TNF in each sample is determined using the percent specific cytotoxicities of the murine standards, as described previously. The WEHI assay results are compiled below in Table 2:

TABLE 2

In vitro activity in the WEHI assay.

| Compound | IC50 (ng/mL) |
|---|---|
| sTNFR-1 2.6D/C106 | 208 |
| s.TNFR-1 4D/C105 | 238 |
| sTNFR-1 4D/C105 db | N/A |

Based on the results of the WEHI assay, there are no significant differences between the sTNFR-I 2.6D/C106 and the sTNFR-I 4D/C105 in terms of in vitro bioefficacy.

B. L929 Cytotoxicity Assay

The L929 cytotoxicity assay is an in vitro cell proliferation assay (Parmely et al. (1993), *J. Immunol.*, 151:389–396) which also assesses the cytotoxicity of TNF-α-sensitive killing. The cell lines are sensitive to TNF-α (i.e., TNF-α is cytotoxic). In the presence of a soluble TNF-α inhibitor, the cells are protected from the cytotoxic effect and thus are able to proliferate.

Protocol

The L929 cell line is obtained from the American Type Culture Collection (Catalog number CCL 1, NCTC clone 929, clone of strain L, connective tissue, mouse). The medium used for propagation is RPMI Medium 1640 supplemented with 10% FBS+1% L-Glutamine Solution +1% Penicillin-Streptomycin Solution.

96-well microtiter plates (Corning) are used in the assay and only the inner 60 wells are utilized. The standard and test sample are tested in triplicate on the same plate.

The TNFα used in the assay is from R&D Systems (Minneapolis, Minn.). The final concentration of TNFα used in the assay is 1 ng/mL in all assay wells.

The assay diluent is L929 growth medium, 10 ng/mL of TNFα, and 10 µg/mL of Actinomycin D (Sigma Chemical Co., St. Louis, Mo.).

The plates are harvested using an XTT/MEN Solution (1.5 mg/mL XTT+75 mM MEN).

On day 1, cells are plates on assay plates. A cell suspension is prepared by trypsinizing and resuspending cells at $3.33 \times 10^4$ cells/mL. 180 mL of this cell suspension is plated into each of the inner 60 wells of the assay plates. 200 mL of growth medium is dispensed into the outer 36 wells to help avoid evaporation artifacts in the assay. The plates are allowed to sit at room temperature, covered with foil and free from drafts, for approximately 1 hour. Assay plates are placed in a 37±2° C. high humidity 5±1% $CO_2$ incubator. Plates are incubated for approximately 20–22 hours prior to addition of sTNFR-I serial dilutions.

On day 2, sTNFR-I 4D/N105 standard is prepared and test samples: Dilute sTNFR-I 4D/N105 standard and test samples to a concentration of approximately 2.0 mg/mL, (or another appropriate concentration). Make serial dilutions of this concentration to create a 10-point dilution curve ranging from approximately $1.0 \times 10^6$ ng/mL to $1.0 \times 10^{-3}$ ng/mL, including a 0 ng/mL (Assay Diluent only) point. If other concentrations are appropriate, they may be used. Add 1000 µL of each dilution in triplicate on each assay plate. Incubate the plates in a 37° C.±2° C. high humidity 5±1% $CO_2$ incubator for 20±1 hours after transfer of serial dilution aliquots to the assay plates.

On day 3, 50 µL/well of the XTT/MEN Solution is added to inner 60 wells of assay plates. Plates are incubated in a 37° C.±2° C. high humidity 5±1% $CO_2$ incubator (Falcon, New York, N.Y.) for 24±0.5 hours.

On day 4, the optical density (O.D.) of the assay plates is read at 450 nm minus 650 nm on an ELISA plate reader (SpectraMAX, Beckman Instruments, Inc., Fullerton, Calif.). If values of 4.000 OD are obtained for wells in a plate at these wavelengths, the plate should be reread at 490 nm minus 650 nm immediately, and the 490 nm minus 650 nm data should be used for calculation.

A standard dose-response curve vs log is prepared using a four parameter logistic curve fit. Calculate The original concentrations of unknown samples are calculated from the standard curve and calculate the $ED_{50}$ for the standard and the correlation coefficient for the standard curve fit.

Results

The L929 Cytotoxicity Assay results are compiled below in Table 3:

TABLE 3

In vitro activity in the L929 Cytotoxicity assay.

| Compound | Concentration (mg/mL) | $ED_{50}$ (ng/mL) |
|---|---|---|
| sTNFR-I 4D/C105 db | 7.8 | 1.0 ± 0.1 |
| sTNFR-I 2.6D/C105 db | 2.6 | 1.1 ± 0.0 |
| sTNFR-I 2.6D/C106 db | 2.2 | 1.0 ± 0.1 |
| sTNFR-I 4D/N105-t-BuPEG (33 kDa) | 2.0 | 229.2 ± 8 |
| sTNFR-I 4D/C105-t-BuPEG (33 kDa) | 1.1 | 325.5 ± 147 |
| sTNFR-I 2.6D/C105-t-BuPEG (33 kDa) | 1.7 | 210.2 ± 9 |
| Internal Std: | | |
| sTNFR-I 4D/C105 | 3.5 | 314.8 ± 188.1 |

The data indicate that the sTNFR-I 4D/C105 db and the sTNFR-I 2.6D/C105 db and sTNFR-I 2.6D/C106 db are active and have comparable dose responses when compared to the standard. The data also indicate that the sTNFR-I sTNFR-I 4D/N105-t-BuPEG(33 kda) and sTNFR-I 2.6D/C105-t-BuPEG(33 kda) are nearly 2 logs lower in activity, but are active in this assay, nonetheless, when compared to the sTNFR-I 4D/C105 db.

| Run #2: | | |
|---|---|---|
| sTNFR-I 3D/C105 db | 0.2 | 2.27 ± 0.3 |
| sTNFR-I 3D/C105 db | 0.2 | 2.0* |
| sTNFR-I 3D/C105 db | 1.9 | 1.8* |
| sTNFR-I 3D/N105 | 2.4 | 413.3* |
| Internal Std: | | |
| sTNFR-I 4D/C105 | 3.5 | 115.9 ± 42.1 |

* Single data point

These data indicate that the sTNFR-I 3D/C105 db is active and the $ED_{50}$ values are in the range of the sTNFR-I 4D/C105 db (Run #1), the sTNFR-I 2.6D/C105 db (Run #1), and the sTNFR-I 2.6D/C106 db (Run #1). The data also indicate that the sTNFR-I 3D/N105 is less active than the sTNFR-I 4D/C105 internal standard.

C. Streptococcal cell wall induced reactivation model

The Streptococcal cell wall induced reactivation model of arthritis in rats assays is accomplished using known protocols (Esser et al. (1985), *Arthritis And Rheumatism*, 28:1402–1411 and Makarov et al. (1996), *Proc. Natl. Acad. Sci. USA*, 93:402–406).

Protocol

Female Lewis rats (Charles River Laboratories, Inc., Wilmington, Mass.), each weighing 175 to 185 grams, are injected intra-articularly into the right ankle joint with a sterile suspension of streptococcal cell wall products containing peptidoglycan-polysaccharide (SCW) (Lee Laboratory, Grayson, Ga.) at a dose of 1.5 mg/10 mg per joint. Saline is injected into the contralateral joint to provide a control. The intra-articular injection of SCW causes an acute arthritis of relatively short duration with swelling of the joint peaking at one to two days post injection. After a period of twenty days, during which the acute inflammatory reaction resolved, SCW is again administered by intravenous injection at a dose of 200 mg/200 mL per rat. The second dose of SCW is sufficient to reactivate inflammation in the ankle joint previously injected with SCW and has little effect on the saline-injected ankle. To assess the extent of inflammation during the 72-hour period following the intravenous injection of SCW, the dimensions of the ankle joint are measured by ankle caliper measurements of the hind ankle at 0, 24, 36, 48, and 72 hours after reactivation of the arthritis and then contralateral hind limb harvest for histology (e.g., inflammation, pannus formation, cartilage damage and bone damage).

Results

The effects of the sTNFR-I 2.6D/C106 db when administered are tested on the development of joint swelling during the reactivation of the arthritis. The inhibitors and vehicle are each administered in a single intravenous injection 24 hours pre-reactivation with the SCW.

sTNFR-I 2.6D/C106 db demonstrates statistically significant efficacy in reducing joint swelling, by analysis of variance (ANOVA) Fisher's post-hoc test (Statview®) at all four doses on days two and three post-reactivation and at all but one dose (1.5 mg/kg) on day one. This reduction in swelling is comparable to the positive control of sTNFR-I 4D/C105 db given at a dose of 0.5 mg/kg daily (i.e.; 8.8 nM) starting at one day pre-reactivation to three days post-reactivation. The sTNFRs also show significant efficacy when the amount of swelling is considered over the three days as a whole. Area under the curve (AUC) display a dose-response relationship at all doses (see FIG. 9, wherein the sTNFR-I 2.6D/C106 db is designated "sTNFR-I 2.6D" and the sTNFR-I 4D/C105 db is designated "sTNFR-I 4D").

The sTNFR-I 2.6D/N105-t-BuPEG(33 kDa) show a significant reduction in ankle width and histological indexes when compared to the disease control group in the model.

D. D-galactosamine/Lipopolysaccharide model

The D-galactosamine (D-GalNH$_2$)/Lipopoly-saccharide (LPS) model (Parmely et al. (1993), supra), is an in vivo, highly TNF-α-dependent animal model of lethality. Additionally, MRL-lpr/lpr autoimmune mice have been shown to be extremely sensitive to LPS- or SEB-induced TNF-α(Mountz et al. (1995), *J. Immunol.*, 155:4829–4837).

Protocol

After overnight fasting, 6–8 week old female MRL-lpr/lpr mice (Jackson Laboratory, Bar Harbor, Me.) receive an I.P. challenge with the following pharmacological reagents: 25 mg of D-GalNH$_2$ (Sigma Chemical Co., St. Louis, Mo.) suspended in Hank's Balanced Salt Solution (Gibco Laboratories, Inc., Grand Island, N.Y.) (50 mg/mL); and lipopolysaccharide (LPS) from *E. coli* Serotype 0127:B8 (Sigma Chemical Co., St. Louis, Mo.) in sterile, endotoxin-free phosphate buffered saline (PBS) (25 mg/mouse) or SEB (Toxin Technologies, Sarasota, Fla.) in normal saline (50 mg/mouse). The various forms of sTNFR are given in serial 2-fold dilutions (mg/kg dosages) to obtain ED$_{50}$ curves generated with statistical software for the MacIntosh (Statview®, Mountain View, Calif.). Lethality is followed through +48 h after challenge.

Results

As shown below in Table 4, when the sTNFR-I 2.6D/C106 db is administered as described above, 1 hour pre-LPS/DGalNH$_2$ challenge, the ED$_{50}$ (i.e., the dose of sTNFR-I 2.6D/C106 db required for 50% protection) at 48 hours is ~50 µg/kg (N=8 individual mice). In comparison to the sTNFR-I 4D/C105 db, there are no significant (P>0.05) differences in the ability of this form to prevent lethality (ED$_{50}$=~50 µg/kg; N=8 individual mice).

TABLE 4

Comparison of sTNFR and Optimized Truncated sTNFR forms in LPS/D-GaINH$_2$ Model

| Agent | ED$_{100}$ | ED$_{50}$ |
|---|---|---|
| sTNFR-I 4D/C105 db | ~100 µg/kg | ~50 µg/kg |
| sTNFR-I 2.6D/C106 db | ~100 µg/kg | ~50 µg/kg |
| sTNFR-I 2.6D/N105-t-BuPEG (33 kDa) | ~2 mg/kg | ~400 µg/kg |
| sTNFR-I 2.6D/N105-MePEG (20 kda) | ~800–1000 µg/kg | ~1 mg/kg |
| sTNFR-I 2.6D/N105-MePEG (20 kda branched) | 2 mg/kg | ~1–1.5 mg/kg |
| sTNFR-I 2.6D/N105-MePEG (40 kda branched) | 1.5 mg/kg | ~1 mg/kg |

The data indicate that sTNFR-I 2.6D/C106 db has equivalent activity as compared to sTNFR-I 4D/C105 db, but that sTNFR-I 2.6D/N105-t-BuPEG(33 kDa) is less active in this model with an ED$_{50}$ of ~400 µg/kg (n=5 individual mice). Additionally, the activity of the sTNFR-I 2.6D/N105-MePEG (20 kDa branched) and 2.6D/N105-MePEG (40 kDa branched) are less active in this model.

E. Adjuvant Induced Arthritis Model

Rheumatoid arthritis induced in rats by adjuvant bears many resemblances to human rheumatoid arthritis. The purpose of this experiment is to demonstrate that systemic administration of truncated sTNFRs has a mitigating effect on the pathogenesis of adjuvant-induced arthritis in mice.

Protocol

Male Lewis rats (5–7/group) (Charles River Laboratories, Inc., Wilmington, Mass.) weighing at least 200 g are cannulated with SQ catheters and allowed to recover for several days. They are then placed in infusion cages and acclimated for a week prior to initiating saline infusion.

On day-0, all rats are injected with 100 µl of Freunds Complete Adjuvant (Sigma Chemical Co., St. Louis, Mo.) to which a synthetic adjuvant, N,N-dioctyldecyldecyl-N', N-bis(2-hydroxy-ethyl) propanediamine, 50 mg/ml, is added. On day 8, different groups of rats are administered by continuous SQ infusion of sTNFR-I 4D/C105 and sTNFR-I 2.6D/N105.

The results are set forth in Table 5.

TABLE 5

Adjuvant induced arthritis

| Compound | Dose (mg/kg/hr) | AUC % (% Inh.) | Paw Wt. (% Inh.) | Inflam. (% Inh.) | Bone Res. Histopathology (% Inh.) |
|---|---|---|---|---|---|
| Study #1 | | | | | |
| sTNFR-I 4D/C105 | 5 | 61 | 46 | 37 | 89 |
| | 1 | 49 | 45 | 26 | 855 |
| | 0.2 | 33 | 40 | 14 | 34 |
| sTNFR-I 2.6D/N105 | 1 | 55 | 53 | 33 | 51 |
| Study #2 | | | | | |
| sTNFR-I 2.6D/N105 | 5 | 42 | ND | 19 | 67 |
| | 1 | 38 | ND | 13 | 49 |

TABLE 5-continued

Adjuvant induced arthritis

| Compound | Dose (mg/kg/ hr) | AUC % (% Inh.) | Paw Wt. (% Inh.) | Inflam. (% Inh.) | Bone Res. Histopathology (% Inh.) |
|---|---|---|---|---|---|
| Study #3 | | | | | |
| sTNFR-I 2.6D/N105-MePEG (20 kda) | 9 | 50 | 40 | 13 | 27 |
| | 3 | 35 | 34 | 9 | 22 |
| | 1 | 36 | 30 | 0 | 0 |
| sTNFR-I 2.6D/N105-MePEG (33 kDa) | 9 | 43 | 37 | | |
| | 3 | 38 | 33 | | |
| | 1 | 24 | 20 | | |

Surprisingly the sTNFR-I 2.6D/N105–t-BuPEG(33 kDa) and sTNFR-I 4D/C105 db are of comparable anti-arthritic activity in adjuvant arthritis in Lewis rats, although the sTNFR-I 4D/C105 db is more potent in the WEHI-164 and L929 in vitro cytotoxicity assays, as well as the LPS/GalN model.

F. Collagen induced arthritis model

Type II collagen-induced arthritis in rats bears many resemblances to human rheumatoid arthritis. The purpose of this experiment is to demonstrate that systemic administration of truncated sTNFRs has a mitigating effect on the pathogenesis of type II collagen-induced arthritis in rats and mice.

Rat Protocol

Female Lewis rats (Charles River Laboratories, Inc., Wilmington, Mass.), had SQ cannulas implanted and they are acclimated to tethering for continuous infusion. Subsequently they are immunized with bovine type II collagen in Freunds incomplete adjuvant. On days 13, 14 or 15 post immunization, animals with established arthritis are randomly subdivided into groups of eight animals each. The experimental groups are infused with vehicle or various doses of sTNFR-I as described in Table 6 for 7 days. Paw inflammation is assessed by daily caliper measurement of ankle joints. On day 7, the animals are euthanized and paws collected for weight determination as an index of inflammation. Ankle and knee joints are collected for histopathologic evaluation of arthritis parameters.

The results are set forth in Table 6A.

TABLE 6A

Collagen induced arthritis

| Compound | Dose | AUC % (% Inh.) | Paw Wt. (% Inh.) | Inflam. (% Inh.) | Bone Res. Histopathology (% Inh.) |
|---|---|---|---|---|---|
| STUDY #1 | (mg/kg/ hr) | | | | |
| sTNFR-I 4D/C105 | 5 | 65 | 81 | ND | ND |
| | 1 | 35 | 34 | ND | ND |
| | 0.2 | 19 | 22 | ND | ND |
| sTNFR-I 2.6D/N105 | 1 | 39 | 41 | ND | ND |
| STUDY #2 | (mg/kg/ day) | | | | |
| sTNFR-I 2.6D/N105-MePEG (33 kDa) | 3 | 50 | 60 | 76 | 46 |

TABLE 6A-continued

Collagen induced arthritis

| Compound | Dose | AUC % (% Inh.) | Paw Wt. (% Inh.) | Inflam. (% Inh.) | Bone Res. Histopathology (% Inh.) |
|---|---|---|---|---|---|
| sTNFR-I 4D/N105-MePEG (33 kDa) | 3 | 47 | 50 | ND | ND |
| STUDY #3 | | | | | |
| sTNFR-I 2.6D/N105-MePEG (33 kDa) | 9 | 25 | 44 | ND | ND |
| sTNFR-I 2.6D/N105-MePEG (33 kDa) | 3 | 25 | 37 | ND | ND |
| sTNFR-I 2.6D/N105-MePEG (20 kDa) | 9 | 35 | 52 | ND | ND |
| sTNFR-I 2.6D/N105-MePEG (20 kDa) | 3 | 35 | 37 | ND | ND |

Interestingly, the rat established collagen model all the treatment groups are nearly the same in efficacy (e.g.; curve shape, percent (%) inhibition of area under the curve (AUC), ranging from 30–59%, and paw weight inhibition ranging from 40–64%. No treatment group is statistically different than any other in this model of arthritis.

Mouse Protocol

Male DBA/1 (Jackson Laboratories, Inc., Bar Harbor, Me.), are immunized with bovine type II collagen (Sigma Chemical Co., St. Louis, Mo.) in Freunds incomplete adjuvant. On days 24, 25 and 26 post-immunization, animals with established arthritis are randomly subdivided into groups of eight animals each. The experimental groups are administered twice daily by the IP route either saline or sTNFR-I 2.6D/N105-MePEG(33 kDa), for 3 consecutive days (days +27, +28, +29). Paw inflammation is assessed by daily caliper measurement of ankle joints. On day +34, the animals are euthanized and paws collected for weight determination as an index of inflammation. Ankle and knee joints are collected for histopathologic evaluation of arthritic parameters.

The results are set forth in Table 6B.

TABLE 6B

Collagen induced arthritis

| Compound | Dose (mg/kg 2D) | AUC% (% Inh.) | Total Histopathology (% Inh.) |
|---|---|---|---|
| STUDY #1 | | | |
| sTNFR-I 4D/C105 db | 3 | 49 | 39 |
| sTNFR-I 4D/N105-t-BuPEG (33 kDa) | 3 | 63 | 55 |
| STUDY #2 | | | |
| sTNFR-I 2.6D/N105-MePEG (33 kDa) | 9 | 73 | ND |
| sTNFR-I 2.6D/N105-MePEG (33 kDa) | 3 | 75 | ND |

G. Continuous Infusion Rat Model of LPS-induced TNF-α Production sTNFR-I 2.6D/C105 db and sTNFR-I 2.6D/C106 db, sTNFR-I 2.6D/N105 and sTNFR-I 4D/N105 are IV jugular implanted with Alzet™ mini-pumps (Alza Corp., Palo Alto, Calif.), according to the manufacturer's instructions, for 48-hour continuous infusion (1 mg/kg). Serum TNF-α levels, measured by an ELISA (Genzyme, Cambridge, Mass.) are significantly decreased compared to controls +2 hours post a high dose LPS challenge.

Example III

Immunogenicity Studies

Various forms of truncated, recombinant soluble TNFR-I are assessed for immunogenicity in several animal models.

A. Rodents sTNFR-I 2.6D/N105-t-BuPEG(33 kDa) and sTNFR-I 4D/C105 db (control) are subcutaneously administered (4 mg/kg) on days 1 and 5 of the experiments to female Sprague Dawley rats (Charles Rivers Labs, Wilmington, Mass.) (n=6–8/group). Retro-orbital blood samples are collected weekly to day 21 post-initial administration, Samples are evaluated for IgM and IgG antibody production.

TABLE 7

Rodent Immunogenicity

| time [days] GROUP + ANIMAL# | 0.01 TITER IgM | 7 TITER IgM | 14 TITER IgM | 21 TITER IgM |
|---|---|---|---|---|
| sTNFR-I 2.6D/N105- 33 kda PEG | | | | |
| 1 | NEG | 0 | 0 | 0 |
| 2 | NEG | 0 | 0 | 0 |
| 3 | NEG | 0 | 0 | 0 |
| 4 | NEG | 0 | 0 | 0 |
| 6 | NEG | 0 | 0 | 0 |
| sTNFR-I 2.6D/N105- t-BuPEG (33 kDa) | 0 | 0.00 | 0.00 | 0.00 |
| SEM | 0 | 0.00 | 0.00 | 0.00 |
| control | | | | |
| 7 | 0 | 0 | 50 | 0 |
| 8 | 0 | 0 | 50 | 0 |
| 3 | 0 | 0 | 100 | 0 |
| 9 | 0 | 0 | 0 | 0 |
| 10 | 0 | 0 | 100 | 50 |
| 11 | 0 | 0 | 100 | 0 |
| 12 | 0 | 0 | 100 | 0 |
| 13 | 0 | 0 | 0 | 0 |
| control | 0 | 0 | 62.5 | 6.3 |
| SEM | 0 | 0 | 15.7 | 6.3 |

| time [days] GROUP + ANIMAL# | 0.01 TITER IgG | 7 TITER IgG | 14 TITER IgG | 21 TITER IgG |
|---|---|---|---|---|
| sTNFR-I 2.6D/N105- t-BuPEG (33 kDa) | | | | |
| 1 | NEG | NEG | 0 | 0 |
| 2 | NEG | NEG | 0 | 0 |
| 3 | NEG | NEG | 0 | 0 |
| 4 | NEG | NEG | 0 | 0 |
| 6 | NEG | NEG | 0 | 0 |
| sTNFR-I 2.6D/N105- t-BuPEG (33 kDa) | 0.00 | 0.00 | 0.00 | 0.00 |
| SEM | 0.00 | 0.00 | 0.00 | 0.00 |
| control | | | | |
| 7 | NEG | NEG | 0 | 200 |
| 8 | NEG | NEG | 0 | 200 |
| 9 | NEG | NEG | 0 | 0 |
| 10 | NEG | NEG | 0 | |
| 11 | NEG | NEG | 200 | 400 |
| 12 | NEG | NEG | 0 | 200 |
| 13 | NEG | NEG | 200 | 800 |
| 14 | NEG | NEG | 0 | 50 |
| control | 0 | 0 | 50 | 231.3 |
| SEM | 0 | 0 | 32.7 | 94.0 |

As seen in the Table 7, sTNFR-I 4D/C105 db administered subcutaneously (SC) on days $^{+}1$ and $^{+}5$, records the higher rat anti- sTNFR-I IgG antibody titers through $^{+}21$ days than the sTNFR-I 2.6D/N105-t-BuPEG(33 kDa) has very weak, if any, antibody titers. Similar trends in immunogenicity are also observed in rats developing rat anti- sTNFR-I IgM antibodies through $^{+}21$ days. sTNFR-I 2.6D/N105-t-BuPEG(33 kDa) do not generate rat anti- sTNFR-I IgM antibodies through $^{+}21$ days.

B. *Papio anubis*

The objective of Part 1, Phase A of the study is to determine the pharmacokinetics and immunogenicity of either the sTNFR-I 4D/C105 db (0.2 mg/kg bodyweight [BW]), sTNFR-I 3D/C105 db (0.2 mg/kg BW), or sTNFR-I 2.6D/C105 db (0.2 mg/kg BW), respectively, when administered IV twice to the healthy baboon, 21 days apart.

The Part 1 study is divided in two phases. Part 1, Phase A is aimed at determining pharmacokinetics and immunogenicity of the different sTNF-RI constructs in the healthy baboon in response to two injections. Twelve baboons are subdivided into three groups. While anesthetized, each group receives 0.2 mg/kg BW of either the sTNFR-I 4D/C105 db, sTNFR-I 3D/C105 db, or sTNFR-I 2.6D/C105 db. Three baboons are studied each session. Animals are followed for 21 days and then receive a second identical IV injection of protein and are studied for an additional 21 days. Pharmacokinetics and immunogenicity are determined at intervals thereafter.

Part 1, Phase B of the study is aimed at evaluating efficacy of these preparations in a well established model of TNFα-mediated lethality (Espat et al., *J. Surg. Res.*, 59:153–158, 1995). Lethal *E. coli* bacteremia is induced in 16 animals in groups of four, by administration of $5–10\times10^{10}$ cfu/kg of live *E. coli*. A placebo group is compared to baboons pretreated IV with either a sTNFR-I 4D/C105 db (0.2 mg/kg bodyweight [BW]), sTNFR-I 3D/C105 db (0.2 mg/kg BW), or sTNFR-I 2.6D/C105 db administered at 1 mg/kg BW.

In both phases of the Part 1 study, Young adult male and female baboons *Papio anubis* (6–11 kg) (Biomedical Research Foundation, San Antonio, Tex.) are fasted overnight. The animals are anesthetized with ketamine (10 mg/kg i.m.) and the cephalic vein is percutaneously cannulated. Anesthesia is maintained by the initial administration of up to 35 mg/kg sodium pentobarbital followed by repeated injection of 3–5 mg/kg/hr of sodium pentobarbital. The upper airway is secured by placement of a cuffed endotracheal tube, and the animals maintain spontaneous respiration. A catheter is placed percutaneously into the femoral artery which permits repeated systemic arterial blood sampling as well as continuous monitoring of heart rate and mean arterial blood pressure via a Datascope 2000 anesthesia monitor (Datascope, San Antonio, Tex.) cardiac monitor. Arterial blood samples are collected at intervals, anti-coagulated with EDTA or heparin, and cooled on ice immediately after drawing. The plasma fraction is separated by centrifugation at 4° C., and stored at −70° C. until assayed. Core temperature is monitored via a rectal probe. An indwelling urinary Foley-type catheter is placed to allow urine collection and to monitor urine output and creatinine clearance. Hemodynamic parameters are monitored every fifteen minutes. All animals receive 0.9% sodium chloride (4 ml/kg) as maintenance i.v. fluid. In the phase B studies, animals receive additional fluid (10 ml/kg every 15 min), if two of the following physiologic criteria are met: 1) mean arterial pressure dropped by more than 30%; 2) heart rate increase by more than 30%, and 3) urine output drop to <1 ml/kg/hr. After baseline blood sampling and a waiting period of at least an hour to allow equilibration infusion of proteins is started.

In the Part 1 Phase A set of studies, recombinant proteins are infused via the cephalic vein and animals are observed for a period of eight hours after which time all catheters are removed and the animals are returned to their cages for 21 days. At 24 and 48 hours and on days 3,5, 8, 11, 16, and 21, the animals are briefly anesthetized with IM ketamine (10 mg/kg) and venous blood samples obtained. On day 21, the animals are re-anesthetized, received a second injection of the protein, and the entire procedure conducted on day zero is repeated for an additional 21 days, at which time the animals are euthanized.

In the Part 1 Phase B studies, one hour prior to the infusion of E. coli, four animals are randomly assigned to receive either placebo or one of the previously mentioned constructs. Animals are observed for a period of eight hours after which time all catheters are removed, the animals are returned to their cages and subsequent survival to the lethal; bacteremia is observed. Animals in excessive discomfort are euthanized. Excessive discomfort is defined by the IACUC as: 1) failure to maintain the sitting or upright position over the previous 12 hours, 2) failure to take food or water within the previous 12 hours, 3) uncontrollable bleeding from catheter sites, or 4) unresponsiveness to external stimuli. Venous blood samples are obtained at −1, 0, 0.5, 1, 1.5, 2, 2.5, 3, 4, 5, 6, 7, 8, 24 hr, 48 hr, and on days 3,5,8,11,16, and 21. At 21 days, surviving animals are euthanized.

The presence of Papio antibodies to the administered recombinant proteins are determined by sandwich ELISA. Very briefly, the sTNFR-1 constructs are coated onto ELISA plates (1 µg/ml) and diluted baboon (1:50 to 1:100,000) plasma (100 µL) are added. After the samples are washed, an horse radish peroxidase (HRP) conjugated protein A is added (0.5 µg/ml), and the assays are visualized with TMB.

Results (Part I)

Plasma half-lives differed significantly among the three constructs. The disappearance curves are determined using a model-independent method and the apparent half-lives are generally evaluated between 8 and 172 hours. In naive animals, the plasma half-life is longest in baboons treated with the 4.0 domain construct (29 hrs) and declines sequentially in baboons treated with the sTNFR-I 3D/C105 db (24.7 hrs) and sTNFR-I 2.6D/C105 db (21.5 hrs). The difference, although statistically significant, is only 26%.

Figure 11:
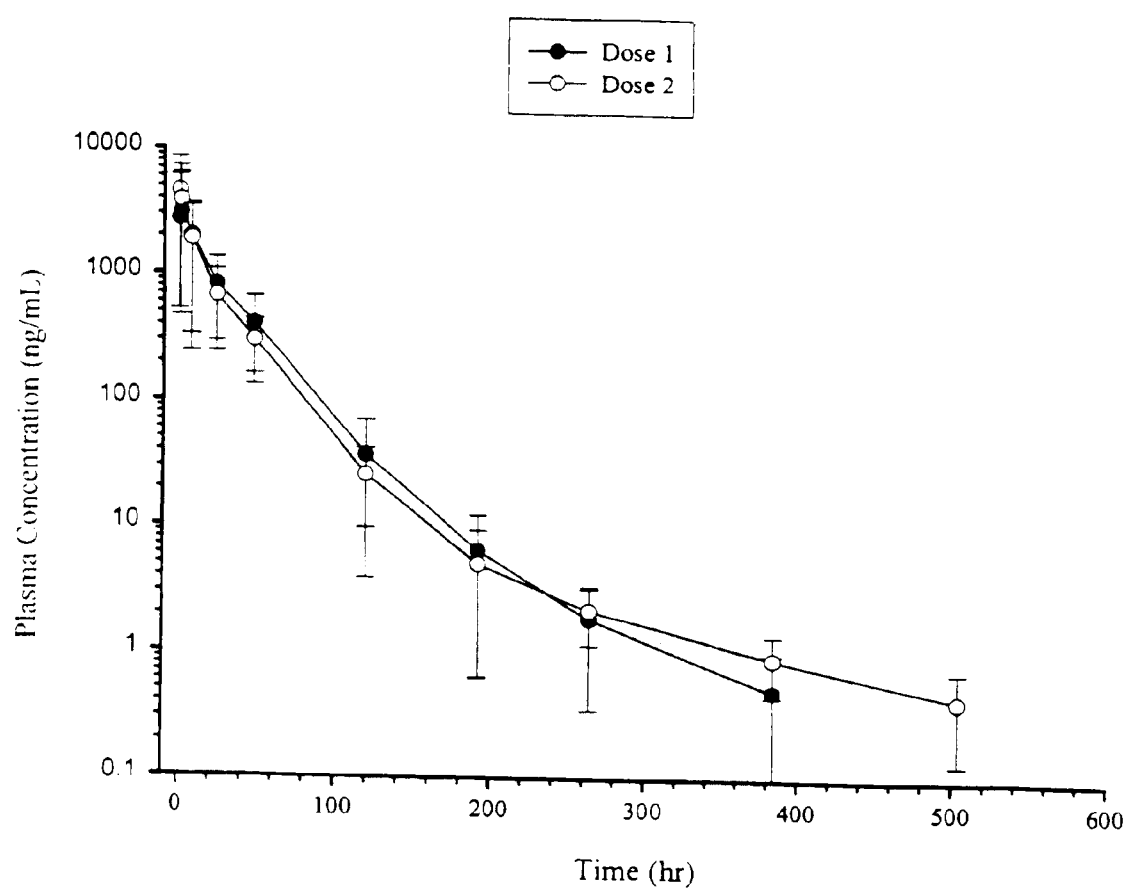
FIG. 11 depicts the plasma profiles of sTNFR-I 3D/C105 db in healthy baboons following two minute intravenous infusion of 0.2 mg/kg, as described in Example III.
Figure 12:
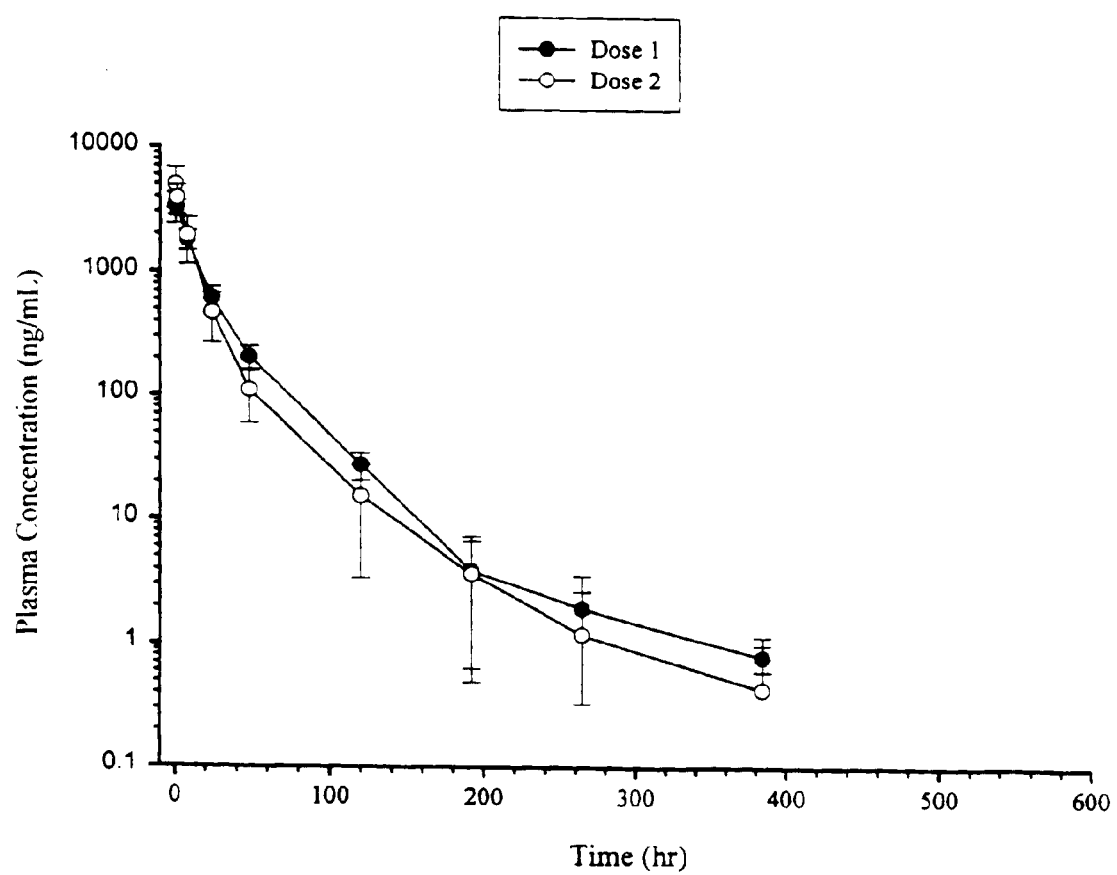
FIG. 12 depicts the plasma profiles of sTNFR-I 2.6D/C105 db in healthy baboons following two minute intravenous infusion of 0.2 mg/kg, as described in Example III.

Unexpectedly, following the second administration of the proteins to the respective baboons, the plasma half-lives tend to be much shorter, indicating a more rapid clearance. This decrease in half-life is most pronounced in baboons receiving sTNFR-I 4D/C105 db where it is shortened by 48% (p<0.01) [FIG. 10]. The reductions in half-life are intermediate in the baboons treated with the sTNFR-I 3D/C105 db (31%) [FIG. 11] and least in the animals given the sTNFR-I 2.6D/C105 db (14%) [FIG. 12]. The reductions in half-life are not statistically different in baboons treated with the sTNFR-I 2.6D/C105 db.

All the preparations are immunogenic in the baboon. However, the frequency of immunogenicity is greatest in the baboons treated with the sTNFR-I 4D/C105 db, intermediate in animals treated with the sTNFR-I 3D/C105 db, and lowest in animals given the sTNFR-I 2.6D/C105 db (Table 8).

TABLE 8

Peak Antibody Responses[1]

|  | First 21 Days | | Second 21 Days | |
| --- | --- | --- | --- | --- |
|  | median | 25%–75% | median | 25%–75% |
| sTNFR-I 4D/C105db (n = 4) | 3.20 | 3.20 3.20 | 3.95 | 3.50 4.40 |
| sTNFR-I 3D/C105db (n = 4) | 1.60 | 0.00 3.65 | 3.50 | 1.30 4.75 |
| sTNFR-I 2.6D/C105db (n = 4) | 0.00* | 0.00 1.75 | 1.45 | 0.00 3.50 |

[1]logarithmic scale (inverse dilution of plasma necessary to produce half-maximal absorbance on a sandwich ELISA; see Experimental Methods)
*p = 0.056, by Kruskal-Wallis two-way ANOVA (log transformed values failed tests of normality)

Antibody responses generally develop around the eighth day following administration of the constructs and are present through the 21 day study period. Furthermore, antibody responses tend to become stronger during the response to the second injection of the protein constructs.

All four of the baboons receiving the sTNFR-I 4D/C105 db develop antibodies, two of four of the animals receiving the sTNFR-I 3D/C105 db develop antibodies and one of the four baboons receiving the sTNFR-I 2.6D/C105 db develop antibodies. By Kruskall-Wallis ANOVA, the magnitude of the antibody response (log transformed) is significantly different among the three groups as a function of time (p<0.05). Post-hoc analysis suggests that the significant difference in antibody responses is principally between animals receiving the sTNFR-I 4D/C105 db and sTNFR-I 2.6D/C105 db with intermediate (and nonsignificant) responses from the animals treated with sTNFR-I 3D/C105 db.

Figure 13:
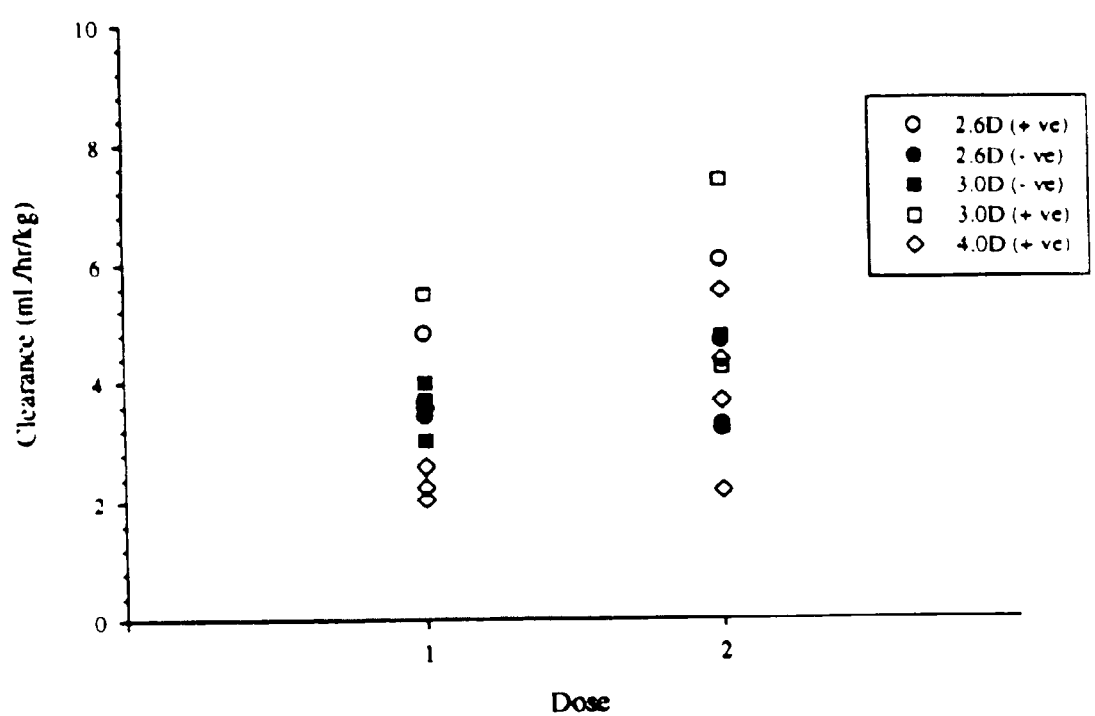
FIG. 13 depicts realtionship between dose and clearance of different dimeric sTNFR-I contructs, as described in Example III.

A correlative relationship between the development of antibodies and the change in clearance between the two 21 day studies (p<0.01) is observed. Not unexpectedly, in those animals that develop a strong antibody response after the first administration of the construct, the protein is cleared more rapidly after the second administration. A change in clearance between the first and second injections is compared between animals that developed an antibody response (n=7) and those that did not (n=5) [FIG. 13].

The antibodies that are detected in the plasma of the baboons are evaluated in a selected number of animals for direct cytotoxicity in the ME-180 cell line and neutralizing capacity in an L-929 assay. No cytotoxicity nor neutralization is seen with antibodies generated to any of the three constructs.

In the Phase I Part A baboon study, animals that develop the strongest antibody responses also have the most rapid increase in the clearance of the constructs following their second administration. Thus, such findings suggest that antibody responses may reduce the biological half-life and thus, therapeutic efficacy of the constructs, and dose adjustments may be required. However, there does not appear to be any adverse clinical response to the presence of the antibodies when the constructs are administered a second time. Thus, therapeutic efforts to modify such constructs to reduce immunogenicity, without significantly affecting half-life or efficacy, are aimed primarily at reducing the need for increasing dose adjustments, rather than the risk of adverse reactions.

Part 1 Phase B Results

Finally, in the naive baboon, all three constructs are nearly equally effective in preventing cytokine mediated injury after *E. coli* bacteremia when administered at a dose of 1.0 mg/kg BW. One of 4 Placebo-treated baboons survive; 4 of 4 sTNFR-I 4D/C105 db- and sTNFR-I 3D/C105 db-treated baboons survive; and 3 of 4 sTNFR-I 2.6D/C105 db-treated baboons survive, respectively. All three constructs prevent TNFα bioactivity and provide excess neutralizing capacity.

Part II

The specific aim of the Part II study in baboons is to determine whether repeated exposure (i.e. 3 separate injections) of animals to various sTNF-RI constructs results in further immunogenicity and decreased half-lives. Additionally, this study is designed to compare the immunogenicity and pharmacokinetics of several STNF-RI constructs, including the sTNFR-I 2.6D/C105 db and sTNFR-I 4D/C105 db, and the sTNFR-I 2.6D/N105-t-BuPEG(33 kDa) and sTNFR-I 4D/N105-t-BuPEG(33 kDa). Finally, this study is designed to evaluate the clinical significance of the antibody response and alter clearance on the subsequent response to a TNFα-mediated injury challenge (*E. coli* bacteremia).

On days 0, 21 and 42, baboons are administered I.V. 0.2 mg/kg of the various constructs (sTNFR-I4D/C105 db, sTNFR-I 2.6D/C105 db, sTNFR-I 2.6D/N105-t-BuPEG(33 kDa), or sTNFR-I 4D/N105-t-BuPEG(33 kDa), respectively). On day $^+$63, baboons receive 2.0 mg/kg BW of their respective constructs. On day $^+$65 (i.e.; 48 hrs later), baboons are challenged with a lethal dose of *E. Coli* as outlined in Part I above. The major findings Part II are as follows:

Results (Part II)

In general, sTNFR-I 4D/N105-t-BuPEG(33 kDa) and sTNFR-I 2.6D/N105-t-BuPEG(33 kDa) have longer half-life's than TNFR-I 4D/C105 db and sTNFR-I 2.6D/C105 db in the naive baboon, irrespective of the number of domains. half-lives range from 30–35 hours for the monopegylated sTNFR-I forms in comparison to 10–20 hours for the dimeric pegylated forms. Additionally, sTNFR-I 4D/N105-t-BuPEG(33 kDa) and TNFR-I 4D/C105 db have longer half-lives than 2.6D/N105-t-BuPEG(33 kDa) and sTNFR-I 2.6D/C105 db in the naive animal.

sTNFR-I 4D/C105 db and sTNFR-I 2.6D/C105 db are also immunogenic, with a modest trend towards reduced immunogenicity with sTNFR-I 2.6D/C105 db. However, only TNFR-I 4D/C105 db exhibits reduced clearance with repeated administrations. sTNFR-I 4D/N105-t-BuPEG(33 kDa) and 2.6D/N105-t-BuPEG(33 kDa) are neither antigenic, nor do their clearance rates change significantly with repeated administration.

Serum obtained from each baboon (N=3) treated with the different- compounds on days $^+$21, day $^+$42, and day $^+$61 are assessed in vitro for immunoreactivity (by a sandwich capture ELISA) to other constructs by using the different constructs as the capture antigen. For example, serum obtained from baboons administered the 2.6D/N105-t-BuPEG(33 kDa) on day $^+$21 (Table 9) do not "react" to either the sTNFR-I 4D/C105 db, sTNFR-I 4D/N105 when these compounds are used on the ELISA plate as the capture antigen.

TABLE 9

Baboon Antibody Response
$I_gG$ (≥ 1:400 titer) Day 21

| Animal given: n = 3 | sTNFR-I 2.6D/C105 db | sTNFR-I 2.6D/N105-t-BuPEG (33 kDa) | sTNFR-I 4D/N105-t-BuPEG (33 kDa) | sTNFR-I 4D/C105-t-BuPEG (33 kDa) | sTNFR-I 4D/C105 db | sTNFR-I 4D/N105 |
|---|---|---|---|---|---|---|
| sTNFR-I 2.6D/N105-t-BuPEG (33 kDa) | | 3/3 neg | | | 3/3 neg | 3/3 neg |
| sTNFR-I 2.6D/C105 db | 3/3 neg | | | | 3/3 neg | 3/3 neg |
| sTNFR-I 4D/N105-t-BuPEG (33 kDa) | | | 3/3 neg | | 3/3 neg | 3/3 neg |
| sTNFR-I 4D/C105-t-BuPEG (33 kDa) | | | | | | |
| sTNFR-I 4D/C105 db | | | | | 1/3 react (400) | 3/3 neg |

A positive reaction is an antibody response of >1:400 titre. Data from day $^+$42 and $^+$61 are shown in Tables 10 and 11. Importantly, there is a positive reaction in vitro with serum obtained from 1 baboon previously treated with the 2.6D/N105-t-BuPEG(33 kDa) when tested against the sTNFR-I 4D/C105 db capture antigen (Table 11).

TABLE 10

Baboon Antibody Response
$I_gG$ (≥ 1:400 titer) Day 42

| Animal given: n = 3 | sTNFR-I 2.6D/C105 db | sTNFR-I 2.6D/N105-t-BuPEG (33 kDa) | sTNFR-I 4D/N105-t-BuPEG (33 kDa) | sTNFR-I 4D/C105-t-BuPEG (33 kDa) | sTNFR-I 4D/C105 db | sTNFR-I 4D/N105 |
|---|---|---|---|---|---|---|
| sTNFR-I 2.6D/N105-t-BuPEG (33 kDa) | | 3/3 neg | | | 3/3 neg | 3/3 neg |

TABLE 10-continued

Baboon Antibody Response
I_gG (≥ 1:400 titer) Day 42

| Animal given: n = 3 | sTNFR-I 2.6D/C105 db | sTNFR-I 2.6D/N105-t-BuPEG (33 kDa) | sTNFR-I 4D/N105-t-BuPEG (33 kDa) | sTNFR-I 4D/C105-t-BuPEG (33 kDa) | sTNFR-I 4D/C105 db | sTNFR-I 4D/N105 |
|---|---|---|---|---|---|---|
| sTNFR-I 2.6D/C105 db | 1/3 react (1600) | | | | 3/3 neg | 3/3 neg |
| sTNFR-I 4D/N105-t-BuPEG (33 kDa) | | | 3/3 neg | | 3/3 neg | 3/3 neg |
| sTNFR-I 4D/C105-t-BuPEG (33 kDa) | | | | | | |
| sTNFR-I 4D/C105 db | | | | | 2/3 react (3200) | 2/3 react (800) |

TABLE 11

Baboon Antibody Response
I_gG (≥ 1:400 titer) Day 61

| Animal given: n = 3 | sTNFR-I 2.6D/C105 db | sTNFR-I 2.6D/N105-t-BuPEG (33 kDa) | sTNFR-I 4D/N105-t-BuPEG (33 kDa) | sTNFR-I 4D/C105-t-BuPEG (33 kDa) | sTNFR-I 4D/C105 db | sTNFR-I 4D/N105 |
|---|---|---|---|---|---|---|
| sTNFR-I 2.6D/N105-t-BuPEG (33 kDa) | | 3/3 neg | | | 1/3 react (1600) | 3/3 neg |
| sTNFR-I 2.6D/C105 db | 2/3 react (204800) | | | | 1/3 react (1600) | 1/3 react (3200) |
| sTNFR-I 4D/N105-t-BuPEG (33 kDa) | | | 3/3 neg | | 1/3 react (6400) | 1/3 react (6400) |
| sTNFR-I 4D/C105-t-BuPEG (33 kDa) | | | | | | |
| sTNFR-I 4D/C105 db | | | | | 1/3 react (6400) | 3/3 react (12800) |

In the baboon previously exposed to the constructs three times, efficacy to a TNFα-mediated injury response is greatest in the (1) sTNFR-I 4D/C105 db, (2) sTNFR-I 2.6D/C105 db, (3) sTNFR-I 4D/N105-t-BuPEG(33 kDa) and (4) 2.6D/N105-t-BuPEG(33 kDa) (as determined by survival, multi-system organ failure (MSOF), serum IL-6 and WBC responses). The "caveat" is that this study did not consider differences in the TNF neutralizing capacity of the different constructs.

C. Chimpanzee

The objective of this study is to assess the immunogenicity of the different sTNF-RI forms which are repeatedly injected by the I.V. route in chimpanzees over a 1 month period. The sTNF-RI forms tested in this study are: the sTNFR-I 2.6D/C105 db, sTNFR-I 4D/C105 db, sTNFR-I 4D/C105-t-BuPEG(33 kDa), sTNFR-I 2.6D/N105-t-BuPEG (33 kDa), and sTNFR-I 4D/N105-t-BuPEG(33 kDa). There are a total of 3 Chimpanzees per treatment group.

The dose regimen/parameters of this study are as follows: Each Chimpanzee receives the test article as an intravenous bolus injection at 0.1 mg/kg, twice weekly on Mondays and Fridays for 4 weeks (8 doses total). The dose volume is variable depending on the concentration of the supplied test article. A 5 mL serum sample is obtained from each animal on Day 0 prior to treatment. Additional serum samples are obtained just prior to drug administration on days 7, 14, 21, and 28.

The chimpanzee immunogenicity raw data are shown in Table 12.

TABLE 12

| | DAY 0 (Pre-dose) | Day 7 (2 doses) | Day 14 (4 doses) | Day 21 (6 doses) | Day 28 (8 doses) |
|---|---|---|---|---|---|
| | Antibody Results IgG Titer (number of chimps) | | | | |
| sTNFR-I 2.6D/C106 db | | | 100 (1) | 400 (1)<br>1600 (1)<br>3200 (1) | 800 (1)<br>3200 (2) |
| sTNFR-I 4D/C105 db | | | 3200 (1) | 400 (1)<br>1600 (1) | 800 (2)<br>12800 (1) |
| sTNFR-I 4D/N105-t-BuPEG (33 kDa) | | | | | |
| sTNFR-I 2.6D/N105-t-BuPEG (33 kDa) | | | | | |

TABLE 12-continued Antibody Results I_gG
Titer (number of chimps)

| | DAY 0 (Pre-dose) | Day 7 (2 doses) | Day 14 (4 doses) | Day 21 (6 doses) | Day 28 (8 doses) |
|---|---|---|---|---|---|
| sTNFR-I 4D/N105-t-BuPEG (33 kDa) | | | | 200 (1) * 1600 (1) | 100 (1) * 400 (1) |

* Note:
Titers observed using sTNFR-I 4D/C105 db as capture antigen.

By day $^+28$, all animals (N=3) treated with either the sTNFR-I 4D/C105 db or sTNFR-I 2.6D/C105 db record a positive reaction (measured by ELISA), with the highest titre observed-as 1:12,800 or 1:3200, respectively (Table 12) (Note: In this part of the experiment, all "immunizing" antigens are used as the corresponding capture antigens immobilized on the ELISA plate). One animal treated with sTNFR-I 4D/N105-t-BuPEG(33 kDa) has a positive antibody reaction on days $^+21$ and $^+28$ (Table 12). Importantly, no animals treated with either the sTNFR-I 4D/C105-t-BuPEG(33 kDa) or sTNFR-I 2.6D/N105-t-BuPEG(33 kDa) are observed to have developed anti-sTNFR-I antibodies throughout the experiment (Table 12).

As described in the baboon experimental section above, serum obtained from each chimpanzee (N=3) treated with the different sTNF-RI forms on days $^+28$ are assessed in vitro for immunoreactivity (by ELISA) to other constructs by using STNF-RI forms as the capture antigen. A positive reaction is an antibody response of >1:400 titre. Importantly, serum obtained from chimpanzees administered the sTNFR-I 2.6D/N105-t-BuPEG(33 kDa) do not "react" to either the sTNFR-I 4D/C105 db, sTNFR-I 4D/N105 when these compounds are used on the ELISA plate as the capture antigen (Table 13)

footpad of the left hind limb with 0.1 mL of an emulsion containing myelin basic protein (MBP) in complete Freunds adjuvant dissolved in phosphate buffered saline (PBS) with an equal volume of complete Freunds adjuvant (CFA) containing 5 mg/ml of *Mycobacterium tuberculosis* H37Ra (Difco Lab MI). Control rats receive 0.1 ml of the PBS/CFA emulsion with no MBP in the footpad of the left hind limb.

Evaluation of clinical disease is based on a conventional 0–5 scoring system. The spectrum of rating is: 0, normal; 0.5, partial loss of tail tone; 1, complete loss of tail tone, 2, dragging of one hind limb; 3 paralysis of both hind limbs; 4, morbid; and 5, death. All injections of sTNFR-I constructs or vehicle are administered at 1 mg/kg S.C. every other day starting on day 9 post immunization. All animals are terminated on day 21. Results are expressed in two forms, clinical severity score as a function of time, and the integrated clinical score for each rat over the entire course of the disease is calculated as the area under the curve of daily clinical score versus time. The values of the treated groups for integrated clinical scoring are compared statistically against those of the control group using the Mann-Whitney test.

Vehicle treated animals have an onset of disease around day 10, the disease peaked on day 16 and then declined. sTNFR-I 4D/C106 db attenuates the clinical symptoms by approximately 73%, when compared to vehicle treated ani-

TABLE 13

Chimpanzee Antibody Results
I_gG (≥ 1:400 titer)

| Animal given: n = 3 | sTNFR-I 2.6D/C105 db | sTNFR-I 2.6D/N105-t-BuPEG (33 kDa) | sTNFR-I 4D/N105-t-BuPEG (33 kDa) | sTNFR-I 4D/C105-t-BuPEG (33 kDa) | sTNFR-I 4D/C105 db | sTNFR-I 4D/N105 |
|---|---|---|---|---|---|---|
| sTNFR-I 2.6D/N105-t-BuPEG (33 kDa) | | 3/3 neg | | | 3/3 neg | 3/3 neg |
| sTNFR-I 2.6D/C105 db | 3/3 react (3200) | | | | 2/3 react (3200) | 1/3 react (400) |
| sTNFR-I 4D/N105-t-BuPEG (33 kDa) | | | 3/3 neg | | 2/3 react (1600) | 2/3 react (3200) |
| sTNFR-I 4D/C105-t-BuPEG (33 kDa) | | | | 3/3 neg | 1/3 react (400) | 3/3 neg |
| sTNFR-I 4D/C105 db | | | | | 3/3 react (12800) | 3/3 react (6400) |

This is also observed with animals treated with either the sTNFR-I 4D/C105 db, sTNFR-I 4D/C105-t-BuPEG(33 kDa), or sTNFR-I 4D/N105-t-BuPEG(33 kDa) (Table 13).

Example IV

EAE is an acute or chronic relapsing inflammatory demyelinating disease of the CNS resulting from sensitization of genetically susceptible animals with neuroantigens such as myelin basic protein (MBP). EAE is an art-accepted and often used animal model for acute human MS.

Female Lewis rats (Jackson Laboratories, Bar Harbor, Me.) are anesthetized and immunized on Day 0 in the mals. The sTNFR-I 4D/C105-t-BuPEG(33 kDa) also attenuate the clinical symptoms by approximately 85%. The sTNFR-I 4D/C105-t-BuPEG(33 kda) and sTNFR-I 2.6DN105-t-BuPEG(33 kDa) are equally potent in attenuating the clinical symptoms (64 and 57%, respectively).

In conclusion, it appears that truncated sTNFRs are effective in mediating some of the clinical sequelae in this animal model of MS.

While the present invention has been described above both generally and in terms of preferred embodiments, it is understood that other variations and modifications will occur to those skilled in the art in light of the description above.

What is claimed is:

1. A truncated sTNFR polypeptide comprising:
amino acid residues 1-110, 1-109, 1-108, 1-107, 1-106, 1-105, 1-104, 1-103, 2-110, 2-109, 2-108, 2-107, 2-106, 2-105, 2-104, 2-103, 3-110, 3-109, 3-108, 3-107, 3-106, 3-105, 3-104, 3-103, 4-110, 4-109, 4-108, 4-107, 4-106, 4-105, 4-104, 4-103, 5-110, 5-109, 5-108, 5-107, 5-106, 5-105, 5-104, 5-103, 6-110, 6-109, 6-108, 6-107, 6-106, 6-105, 6-104, 6-103, 7-110, 7-109, 7-108, 7-107, 7-106, 7-105, 7-104, 7-103, 8-110, 8-109, 8-108, 8-107, 8-106, 8-105, 8-104, 8-103, 9-110, 9-109, 9-108, 9-107, 9-106, 9-105, 9-104, 9-103, 10-110, 10-109, 10-108, 10-107, 10-106, 10-105, 10-104, 10-103, 11-110, 11-109, 11-108, 11-107, 11-106, 11-105, 11-104, 11-103, 12-110, 12-109, 12-108, 12-107, 12-106, 12-105, 12-104, 12-103, 13-110, 13-109, 13-108, 13-107, 13-106, 13-105, 13-104, 13-103, 14-110, 14-109, 14-108, 14-107, 14-106, 14-105, 14-104, 14-103, 15-110, 15-109, 15-108, 15-107, 15-106, 15-105, 15-104, 15-103, 16-110, 16-109, 16-108, 16-107, 16-106, 16-105, 16-104, 16-103, 17-110, 17-109, 17-108, 17-107, 17-106, 17-105, 17-104, 17-103, 18-110, 18-109, 18-108, 18-107, 18-106, 18-105, 18-104, 18-103, 19-110, 19-109, 19-108, 19-107, 19-106, 19-105, 19-104, or 19-103 of SEQ ID NO: 2; provided however, that when the truncated sTNFR polypeptide comprises amino acid residues 1-110, 2-110, 3-110, 4-110, 5-110, 6-110, 7-110, 8-110, 9-110, 10-110, 11-110, 12-110, 13-110, 14-110, 15-110, 16-110, 17-110, 18-110, or 19-110 of SEQ ID NO: 2, the polypeptide does not further comprise amino acid residues 111-161 of SEQ ID NO: 2 or a portion thereof; and optionally further comprising an amino-terminal methionine.

2. An isolated truncated sTNFR polypeptide comprising the amino acid sequence as set forth in SEQ ID NO: 4, SEQ ID NO: 6, SEQ ID NO: 8, SEQ ID NO: 12, SEQ ID NO: 10, or SEQ ID NO: 14. provide however, that the truncated sTNFR polypeptide does not comprise amino acid residues 111–161 of SEQ ID NO: 2 or a portion thereof.

3. The polypeptide of either claim 1 or 2, wherein said amino acid sequence is nonglycosylated.

4. The polypeptide of either claim 1 or 2, wherein said amino acid sequence is glycosylated.

5. The polypeptide of either claim 1 or 2, wherein the protein is conjugated to a water soluble polymer.

6. The polypeptide of claim 5, wherein the water soluble polymer is polyethylene glycol.

7. A polyvalent truncated sTNFR molecule comprising at least one polypeptide of either claim 1 or 2.

8. A pharmaceutical composition comprising the polyvalent truncated sTNFR molecule of claim 7 in association with a pharmaceutically acceptable vehicle.

9. A method of preparing a pharmaceutical composition wherein a therapeutically effective amount of the polyvalent truncated sTNFR molecule of claim 7 is mixed with one or more pharmaceutically acceptable vehicles.

10. A kit for preparing an aqueous protein formulation comprising a first container having the polyvalent truncated sTNFR molecule of claim 7 and a second container having a physiologically acceptable solvent.

11. A polyvalent molecule having the formula $R_1$—X—$R_2$, wherein:
   X comprises a linker, wherein said linker is a water soluble polymer; and
   $R_1$ and $R_2$ are biologically-active molecules covalently bonded to said water soluble polymer, wherein at least one of $R_1$ and $R_2$ is a polypeptide of either claim 1 or 2.

12. The polyvalent molecule of claim 11, wherein the water soluble polymer is polyethylene glycol.

13. The polyvalent molecule of claim 12, wherein $R_1$ and $R_2$ are polypeptides comprising:
   (a) the amino acid sequence as set forth in SEQ ID NO: 4; or
   (b) the amino acid sequence as set forth in SEQ ID NO: 6.

14. A truncated sTNFR polypeptide which is the recombinant expression product of a prokaryotic or eukaryotic host cell containing an exogenous polynucleotide encoding the polypeptide of either claim 1 or 2.

15. A pharmaceutical composition comprising the polypeptide of either claim 1 or 2 in association with a pharmaceutically acceptable vehicle.

16. A pharmaceutical composition comprising:
   A) a polypeptide produced by a process comprising the steps of growing a prokaryotic or eukaryotic host cell containing a polynucleotide encoding the polypeptide of either claim 1 or 2 in a suitable nutrient medium and isolating the polypeptide from the host cell or nutrient medium; and
   B) a pharmaceutically acceptable vehicle.

17. A pharmaceutical composition comprising:
   A) a polypeptide produced by a process comprising the steps of:
      (a) culturing a prokaryotic or eukaryotic host cell containing a polynucleotide encoding the polypeptide of either claim 1 or 2;
      (b) maintaining the host cell under conditions allowing the expression of the polypeptide by the host cell; and
      (c) isolating the polypeptide expressed by the host cell; and
   B) a pharmaceutically acceptable vehicle.

18. A method of preparing a pharmaceutical composition wherein a therapeutically effective amount of the polypeptide of either claim 1 or 2 is mixed with one or more pharmaceutically acceptable vehicles.

19. A kit for preparing an aqueous protein formulation comprising a first container having the polypeptide of either claim 1 or 2 and a second container having a physiologically acceptable solvent.

20. The polypeptide of either claim 1 or 2, wherein the protein is fused to a heterologous amino acid sequence.

21. The polypeptide of claim 20, wherein the heterologous amino acid sequence is an IgG constant domain or fragment thereof.

22. A truncated sTNFR polypeptide which is the recombinant expression product of a prokaryotic or eukaryotic host cell containing an exogenous polynucleotide comprising a nucleotide sequence:
   (a) as set forth in SEQ ID No: 3;
   (b) as set forth in SEQ ID NO: 5;
   (c) as set forth in SEQ ID NO: 7;
   (d) as set for thin SEQ ID NO: 11;
   (e) as set forth in SEQ ID NO: 9;
   (f) as set forth in SEQ ID No: 13;
   (g) that is a degenerate sequence of the nucleotide sequence of any of (a)–(f); or
   (h) encoding a polypeptide that is at least 90 percent identical to the polypeptide encoded by the nucleotide sequence of any of (a)–(g);
   provided however, that the polypeptide does not comprise amino acid residues 111–161 of SEQ ID NO: 2 or a portion thereof;
   and optionally further comprising a nucleotide sequence encoding an amino-terminal methionine.

23. A truncated sTNFR polypeptide which is the recombinant expression product of a prokaryotic or eukaryote host cell containing an exogenous polynucleotide comprising a nucleotide sequence as set forth in SEQ ID NO: 3, SEQ ID NO: 5, SEQ ID NO: 7, SEQ ID NO: 11, SEQ ID NO: 9, or SEQ ID NO: 13, or a TNF inhibitory fragment thereof;
   provided however, that the truncated sTNFR polypeptide does not comprise amino acid residues 111–161 of SEQ ID NO: 2 or a portion thereof.

24. A pharmaceutical composition comprising:
   A) a polypeptide produced by a process comprising growing a prokaryotic or eukaryotic host cell containing a polynucleotide comprising a nucleotide sequence:
      (a) as set forth in SEQ ID NO: 3;
      (b) as set forth in SEQ ID NO: 5;
      (c) as set forth in SEQ ID NO; 7;
      (d) as set forth in SEQ ID NO: 11;
      (e) as set forth in SEQ ID NO: 9;
      (f) as set forth in SEQ ID NO: 13;
      (g) that is a degenerate sequence of the nucleotide sequence of any of (a)–(f); or
      (h) encoding a polypeptide that is at least 90 percent identical to the polypeptide encoded by the nucleotide sequence of any of (a)–(g);
      provided however, that the polypeptide does not comprise amino acid residues 111–161 of SEQ ID NO: 2 or a portion thereof;
      and optionally further comprising a nucleotide sequence encoding an amino-terminal methionine; in a suitable nutrient medium and isolating the polypeptide from the host cell or nutrient medium; and
   B) a pharmaceutically acceptable vehicle.

25. A pharmaceutical composition comprising:
   A) a polypeptide produced by a process comprising growing a prokaryotic or eukaryotic host cell containing a polynucleotide comprising a nucleotide sequence as set forth in SEQ ID NO: 3, SEQ ID NO: 5, SEQ ID NO: 7, SEQ ID NO: 11, SEQ ID NO: 9, or SEQ ID NO: 13, or a TNF inhibitory fragment thereof, wherein the polypeptide does not comprise amino acid residues 111–161 of SEQ ID NO: 2 or a portion thereof in a suitable nutrient medium and isolating the polypeptide from the host cell or nutrient medium; and B) a pharmaceutically acceptable vehicle.

26. A pharmaceutical composition comprising:

A) a polypeptide produced by a process comprising:
   (a) culturing a prokaryotic or eukaryotic host cell containing a polynucleotide comprising a nucleotide sequence:
      (i) as set forth in SEQ ID NO: 3;
      (ii) as set forth in SEQ ID NO: 5;
      (iii) as set forth in SEQ ID NO: 7;
      (iv) as set forth in SEQ ID NO: 11;
      (v) as set forth in SEQ ID NO: 9;
      (vi) as set forth in SEQ ID NO: 13;
      (vii) that is a sequence of the nucleotide sequence of any of (i)–(vi); or
      (viii) encoding a polypeptide that is at least 90 percent identical to the polypeptide encoded by the nucleotide sequence of any of (i)–(vii);
      provided however, that the polypeptide does not comprise amino acid residues 111–161 of SEQ ID NO: 2 or a portion thereof;
      and optionally further comprising a nucleotide sequence encoding an amino-terminal methionine;
   (b) maintaining the host cell under conditions allowing the expression of the polypeptide by the host cell; and
   (c) isolating the polypeptide expressed by the host cell; and B) a pharmaceutically acceptable vehicle.

27. A pharmaceutical composition comprising:

A) a polypeptide produced by a process comprising:
   (a) culturing a prokaryotic or eukaryotic host cell containing a polynucleotide comprising a nucleotide sequence as set forth in SEQ ID NO: 3, SEQ ID NO: 5, SEQ ID NO: 7, SEQ ID NO: 11, SEQ ID NO: 9, or SEQ ID NO: 13, or a TNF inhibitory fragment thereof, wherein the polypeptide does not comprise amino acid residues 111–161 of SEQ ID NO: 2 or a portion thereof, in a suitable nutrient medium;
   (b) maintaining the host cell under conditions allowing the expression of the polypeptide by the host cell; and
   (c) isolating the polypeptide expressed by the host cell; and B) a pharmaceutically acceptable vehicle.

\* \* \* \* \*